United States Patent
Popelka et al.

(10) Patent No.: US 10,933,213 B2
(45) Date of Patent: Mar. 2, 2021

(54) DEVICE AND METHOD FOR HEARING THRESHOLD-ADAPTED ACOUSTIC STIMULATION

(71) Applicants: THE BOARD OF TRUSTEES OF THE LELAND STANFORD JUNIOR UNIVERSITY, Stanford, CA (US); FORSCHUNGSZENTRUM JULICH GMBH, Julich (DE)

(72) Inventors: Gerald R. Popelka, Stanford, CA (US); Peter Alexander Tass, Stanford, CA (US)

(73) Assignees: THE BOARD OF TRUSTEES OF THE LELAND STANFORD JUNIOR UNIVERSITY, Stanford, CA (US); FORSCHUNGSZENTRUM JÜLICH GMBH, Jülich (DE)

( * ) Notice: Subject to any disclaimer, the term of this patent is extended or adjusted under 35 U.S.C. 154(b) by 255 days.

(21) Appl. No.: 16/324,113

(22) PCT Filed: Jul. 20, 2017

(86) PCT No.: PCT/US2017/043151
§ 371 (c)(1),
(2) Date: Feb. 7, 2019

(87) PCT Pub. No.: WO2018/031215
PCT Pub. Date: Feb. 15, 2018

(65) Prior Publication Data
US 2019/0201657 A1    Jul. 4, 2019

(30) Foreign Application Priority Data

Aug. 12, 2016  (DE) .................. 10 2016 009 874.0

(51) Int. Cl.
*A61M 21/00* (2006.01)
*A61N 1/36* (2006.01)
(Continued)

(52) U.S. Cl.
CPC ............. *A61M 21/00* (2013.01); *A61B 5/128* (2013.01); *A61N 1/36* (2013.01); *A61N 1/36038* (2017.08);
(Continued)

(58) Field of Classification Search
CPC ..... A61M 21/00; A61N 1/36; A61N 1/36038; A61B 5/128; H04R 25/75
See application file for complete search history.

(56) References Cited

U.S. PATENT DOCUMENTS

| 4,222,393 A | 9/1980 | Hocks |
| 7,376,563 B2 | 5/2008 | Leysieffer et al. |

(Continued)

FOREIGN PATENT DOCUMENTS

| EP | 2 103 288 A2 | 9/2009 |
| WO | WO-2005/053533 A1 | 6/2005 |
| WO | WO-2016-004970 A1 | 1/2016 |

OTHER PUBLICATIONS

Extended European Search Report on EP Application No. 17839995.2 dated Jan. 31, 2020, 10 pages.
(Continued)

*Primary Examiner* — John P Lacyk
(74) *Attorney, Agent, or Firm* — Foley & Lardner LLP

(57) ABSTRACT

A device for stimulation of a patient with acoustic stimulation signals includes a stimulation unit for generating acoustic stimulation signals and a control unit for controlling the stimulation unit. The control unit is configured so that it determines a bandwidth of an auditory filter with a frequency of a predetermined tone as a center frequency,
(Continued)

wherein this bandwidth is a reference bandwidth. The control unit determines a frequency of a first acoustic therapy signal such that a measure of coverage between the reference bandwidth around the frequency of the predetermined tone and a first bandwidth of an auditory filter with the frequency of the first acoustic therapy signal as a center frequency assumes a predetermined first value, and controls the stimulation unit such that the stimulation unit generates the first acoustic therapy signal.

29 Claims, 28 Drawing Sheets

(51) Int. Cl.
    *H04R 25/00*     (2006.01)
    *A61B 5/12*     (2006.01)
    *A61F 11/00*     (2006.01)
    *A61B 5/0476*     (2006.01)

(52) U.S. Cl.
    CPC ............ *H04R 25/75* (2013.01); *A61B 5/0476* (2013.01); *A61B 5/125* (2013.01); *A61F 11/00* (2013.01); *A61M 2021/0027* (2013.01); *A61M 2205/3317* (2013.01); *A61M 2230/10* (2013.01)

(56) References Cited

U.S. PATENT DOCUMENTS

| | | |
|---|---|---|
| 2002/0177877 A1 | 11/2002 | Choy |
| 2016/0151629 A1 | 6/2016 | Chalupper et al. |
| 2016/0175557 A1 | 6/2016 | Tass |

OTHER PUBLICATIONS

Extended European Search Report on EP Application No. 17839995.2 dated Jan. 23, 2020, 10 pages.
Foreign Search Report on EP 17839995.2 dated Feb. 18, 2020, 1 page.
International Preliminary Report on Patentability issued in PCT Application No. PCT/US2017/043151 dated Feb. 12, 2019, 9 pages.
Tass et al., "Counteracting tinnitus by acoustic coordinated reset neuromodulation", restorative neurology and neuroscience, vol. 30, Jan. 1, 2012, pp. 137-159.
International Search Report and Written Opinion (ISA/KR) for International Application No. PCT/US2017/043151, dated Nov. 2, 2017, 13 pages.

ed with four CR tones in the same fixed pattern relative to the tinnitus frequency $f_T$. All four CR tones with
DEVICE AND METHOD FOR HEARING THRESHOLD-ADAPTED ACOUSTIC STIMULATION

CROSS-REFERENCE TO RELATED APPLICATION

This application is a national stage entry of International Application No. PCT/US2017/043151, filed Jul. 20, 2017, which claims the benefit of German Patent Application No. 10 2016 009 874.0, filed Aug. 12, 2016, the contents of which are incorporated herein by reference in their entirety.

TECHNICAL FIELD

The present disclosure relates to a device and a method for hearing threshold-adapted acoustic stimulation.

BACKGROUND

Subjective tinnitus is the perception of a sound or noise without a physical sound and/or noise source. Subjective tinnitus occurs in the patient's brain and can be perceived just by the patient. A distinction is made between tonal tinnitus, namely perception of a tone, in comparison with atonal tinnitus, namely perception of a sound.

In patients who suffer from tinnitus, nerve cell ensembles in specific regions of the brain are pathologically active, e.g., excessively synchronously active. In this case, a large number of neurons are forming action potentials synchronously. The neurons involved fire excessively synchronously. In a healthy person, however, the neurons in these regions of the brain will fire in a qualitatively different manner, for example, in an uncorrelated manner.

For treatment of tonal tinnitus, the acoustic "coordinated reset" (CR) stimulation has been developed, counteracting pathologically synchronous neural activity in a targeted manner. In the past, the dominant frequency $f_T$ used for this purpose, namely the level of the tone or the pitch of the tinnitus tone perceived by the patient, is determined audiologically, in particular by balancing of tone levels, namely pitch matching (cf. documents D13 and D22 cited in the bibliography at the end of the specification). All patients are stimulated with four CR tones in the same fixed pattern relative to the tinnitus frequency $f_T$. All four CR tones with the frequencies $f_{CR1}$, $f_{CR2}$, $f_{CR3}$ and $f_{CR4}$ have a fixed frequency ratio in all patients in comparison with the tinnitus frequency $f_T$ and they cover barely one octave, wherein $f_{CR1}=77\%*f_T$ and $f_{CR4}=140\%*f_T$ (cf. documents D9 and D22). The CR tones are administered with a loudness just barely above the hearing threshold, typically up to 5 dB above the hearing threshold. The sole patient-specific parameter in this treatment is the tinnitus frequency $f_T$, which is measured audiologically.

The width of audiological filters measured on the frequency axis increases with an increase in hearing impairment (cf. document D18). This filter width corresponds to the range in the primary auditory cortex, for example, which is activated, e.g., stimulated, by a tone. To stimulate specific regions of the central auditory system in the most well-defined and controlled possible manner, the hearing threshold-dependent change in the auditory filters should also be taken into account in determining the CR therapy tones. If this is not done, then the acoustic stimulation with CR tones using fixed frequency ratios in comparison with $f_T$ can lead to suboptimal effects or may even be completely ineffective.

CR stimulation typically involves stimulation of neural subpopulations that are sufficiently separate but are not too far apart. Accordingly, the frequency differences, namely the pitch intervals between the individual CR therapy tones, can be neither too large nor too small, and the optimum intervals between the respective therapy tones depend on the respective hearing thresholds.

In the case of multiple dominant tinnitus tones, these can be treated successfully. In this case, what was said above also applies here in the same way: in the treatment of all dominant tinnitus tones, the CR therapy tones are each to be adapted to the hearing threshold in order to achieve the best possible therapeutic effects.

SUMMARY

In the past, four CR tones have been used according to a rigid frequency scheme. Embodiments of this disclosure make it possible (i) to personalize the intervals of the CR tones by adapting them to the hearing threshold of the respective patient, and (ii) to perform stimulation with the optimum number of CR tones.

Some embodiments of this disclosure are based on the object of providing a device and a method for acoustic stimulation, with which patients suffering from tinnitus or some other disease characterized by pathological synchronous neural activity can be treated in comparison with traditional devices and methods.

The statement of object on which some embodiments of this disclosure are based is achieved by the features of the independent claims. Advantageous refinements and embodiments of this disclosure are defined in the dependent claims.

BRIEF DESCRIPTION OF THE DRAWINGS

Embodiments of this disclosure are explained in greater detail below in example embodiments with reference to the drawings, in which.

3

Figure 11:
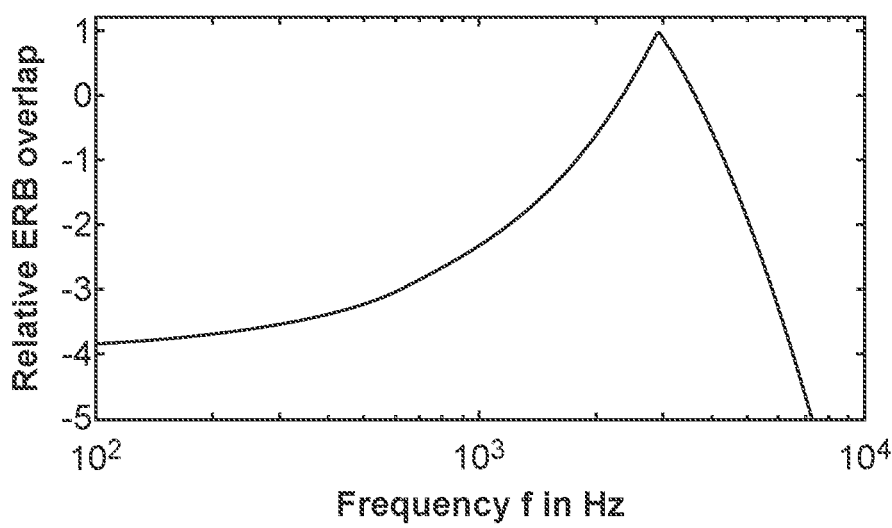
Figure 12:
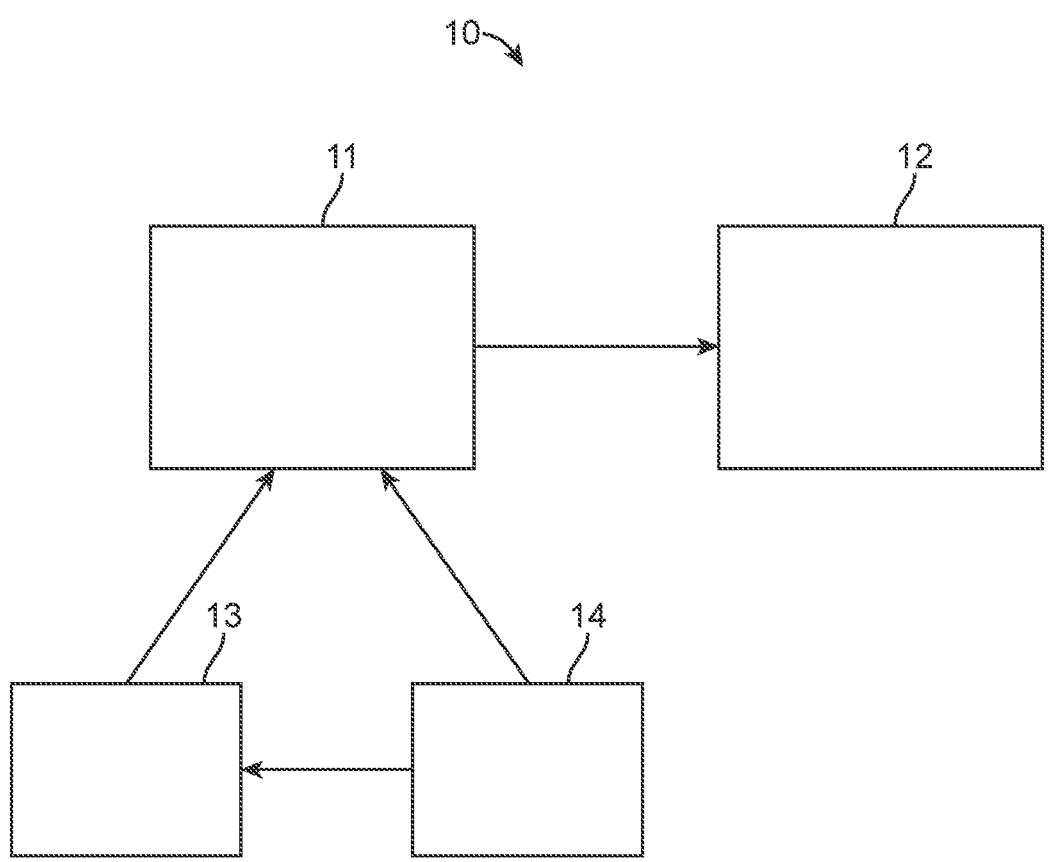
Figure 13:
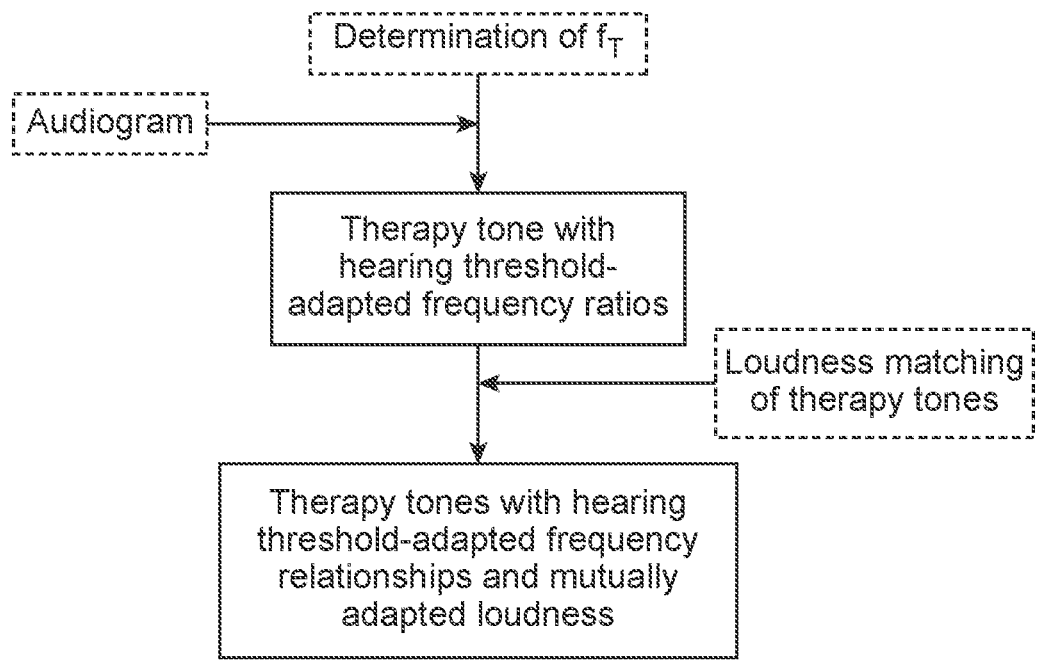
Figure 14:
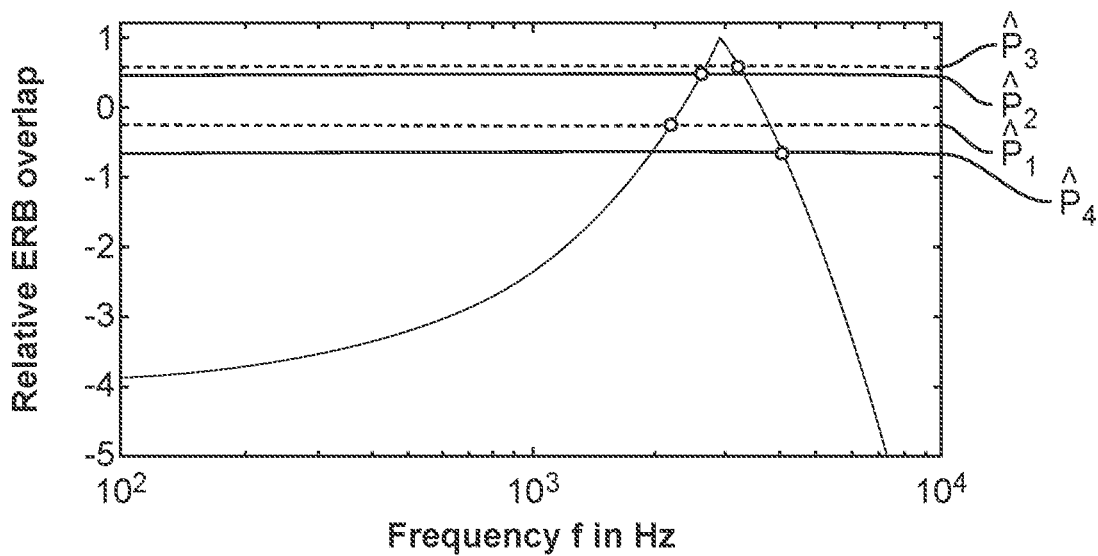
Figure 15:
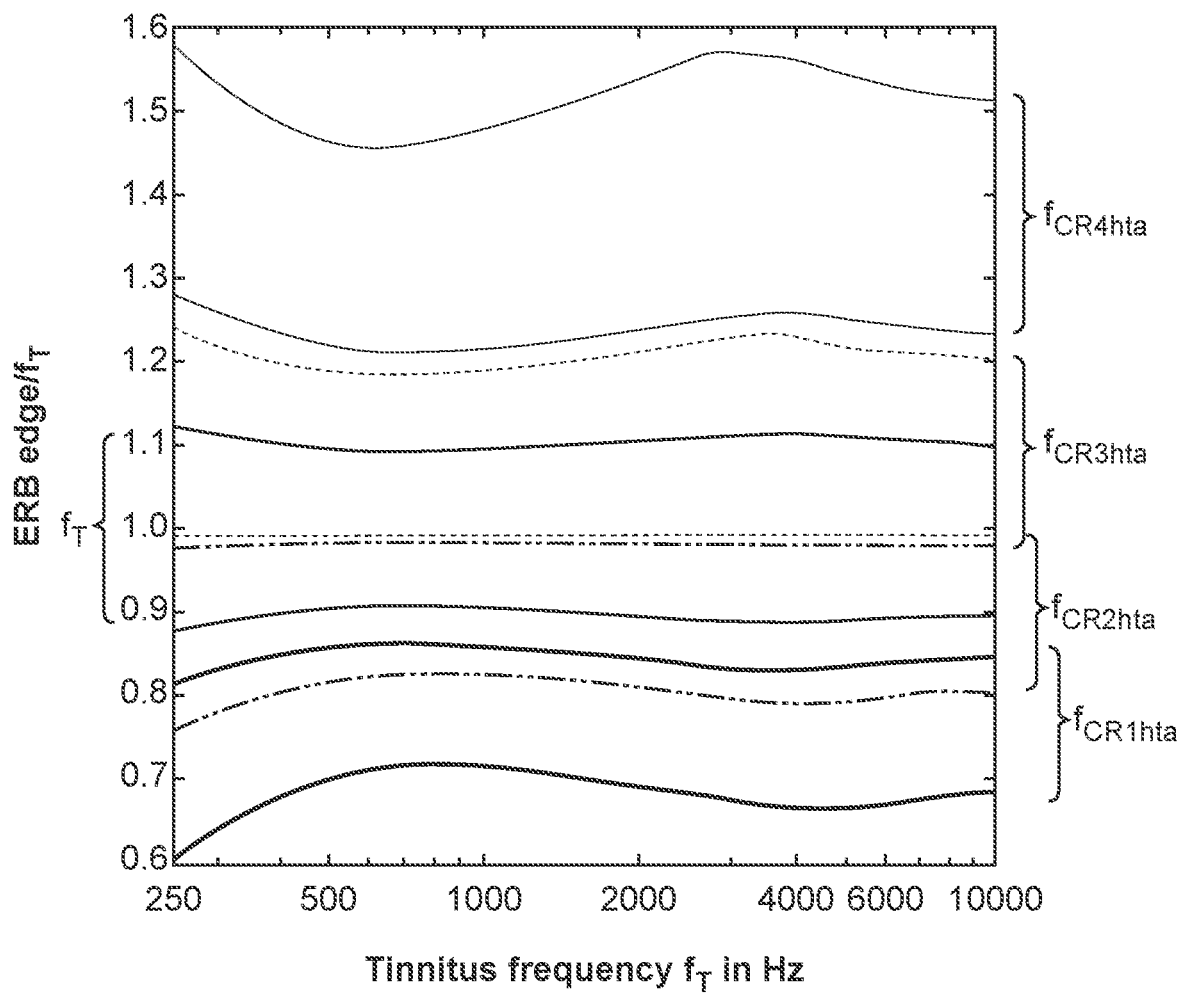
Figure 16:
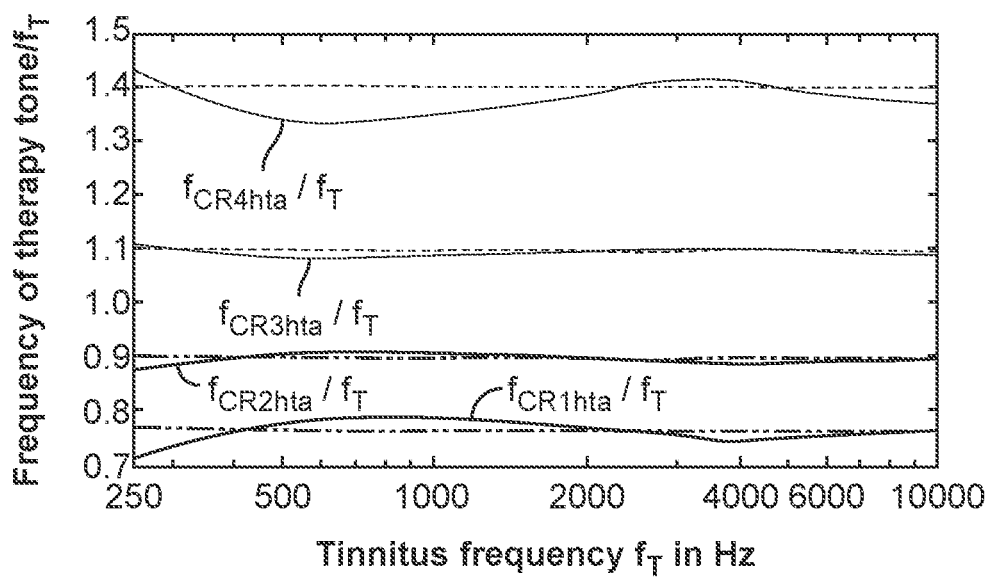
Figure 17:
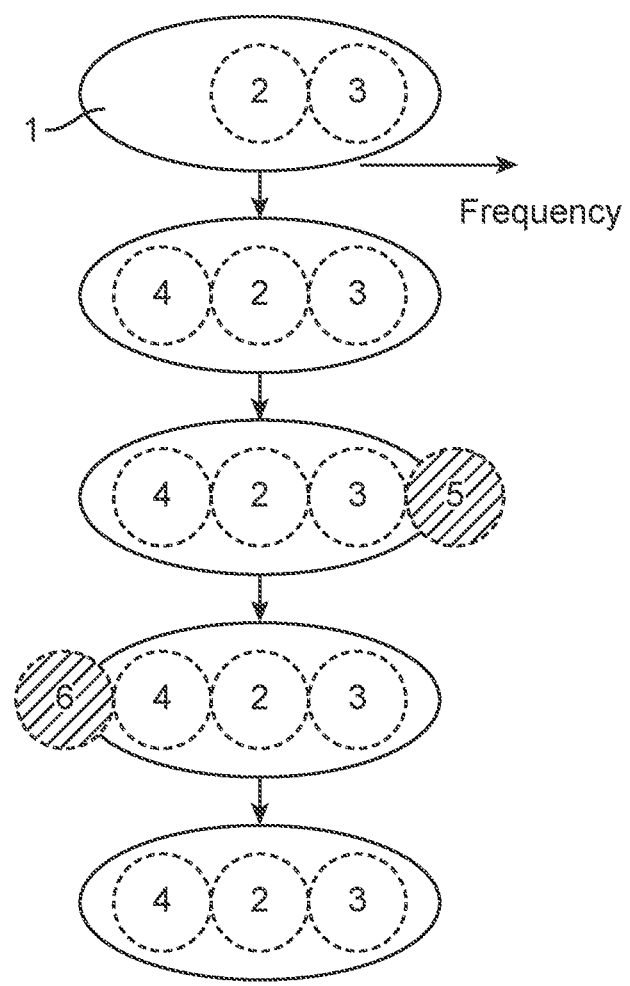
Figure 18:
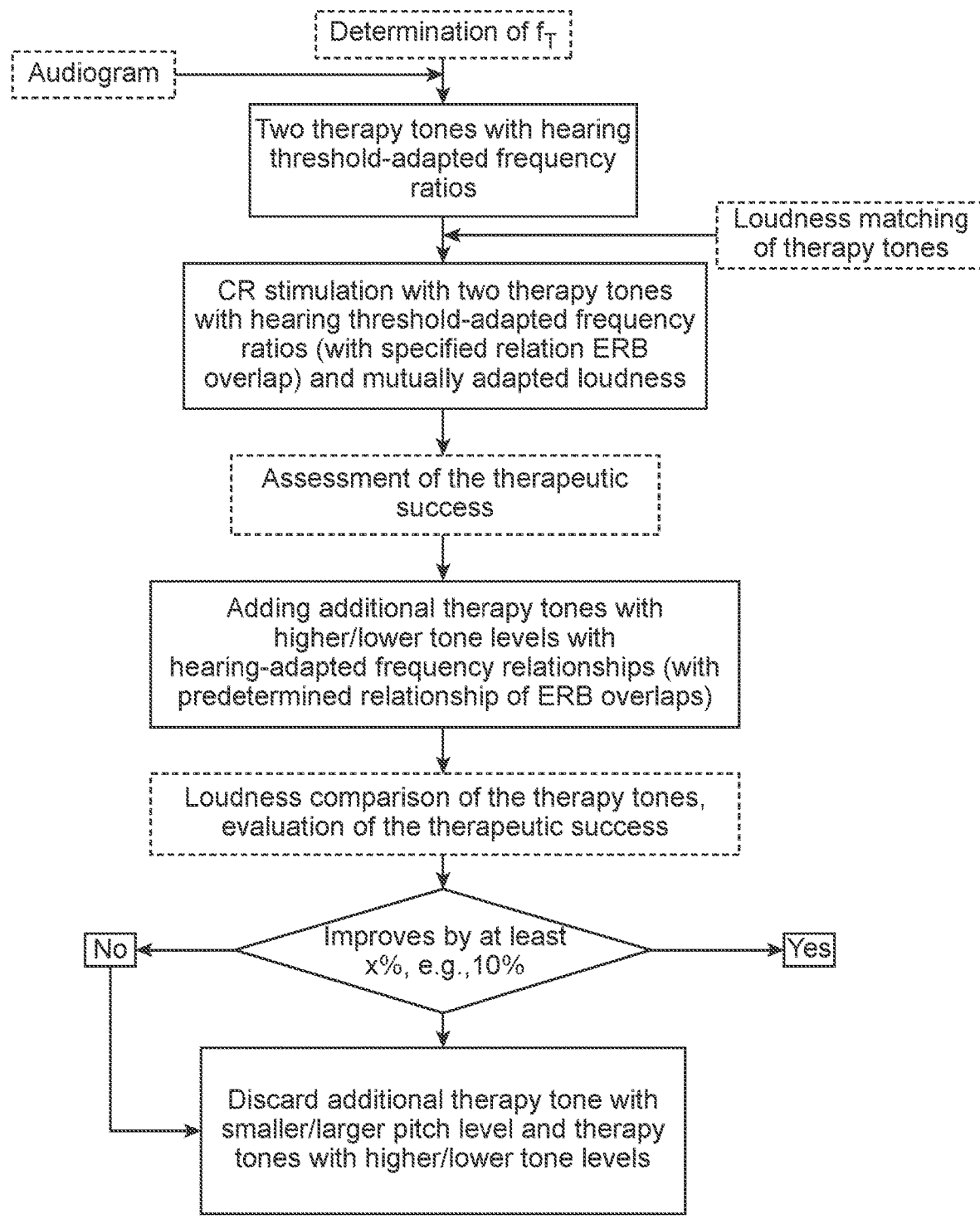
Figure 19:
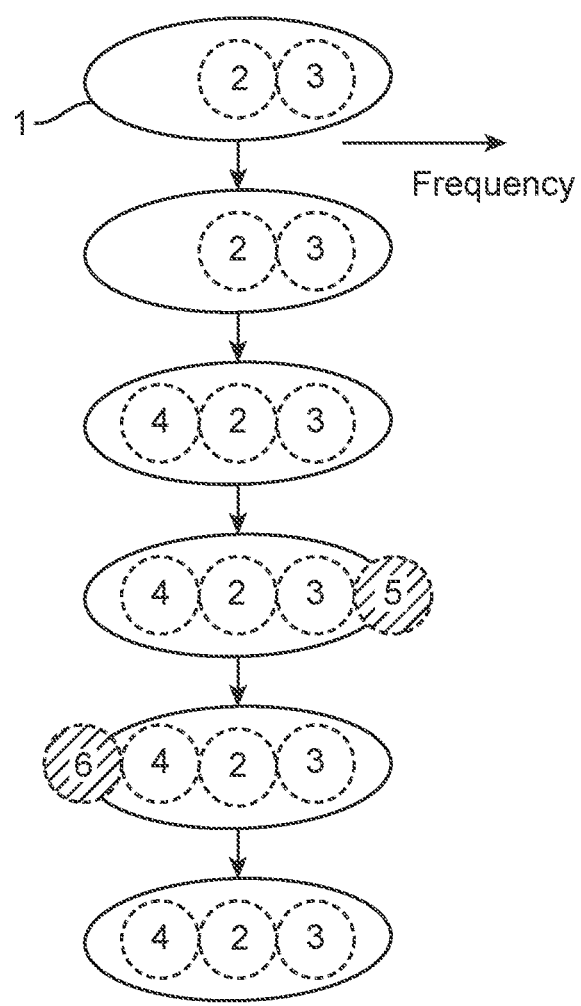
Figure 20:
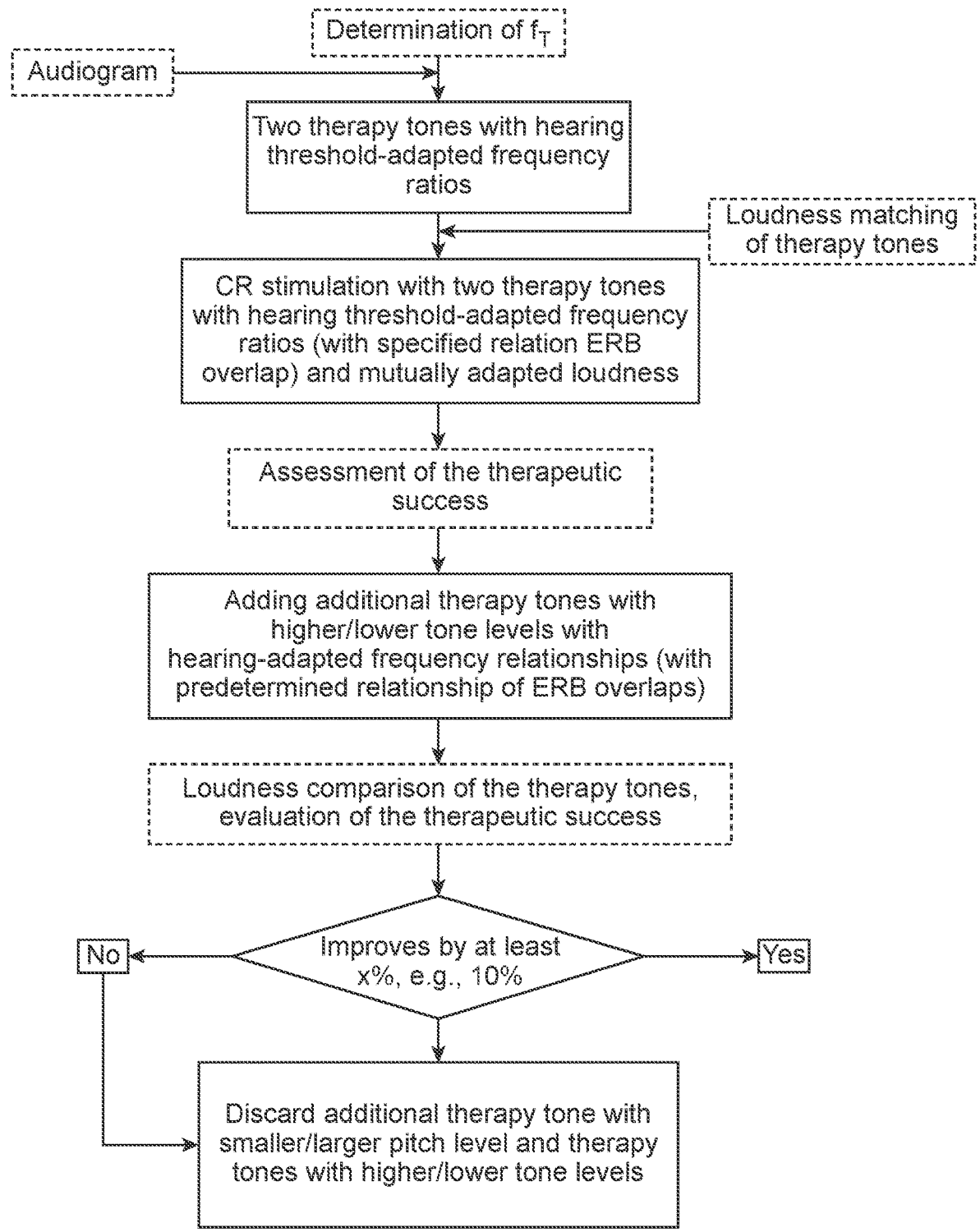
Figure 21:
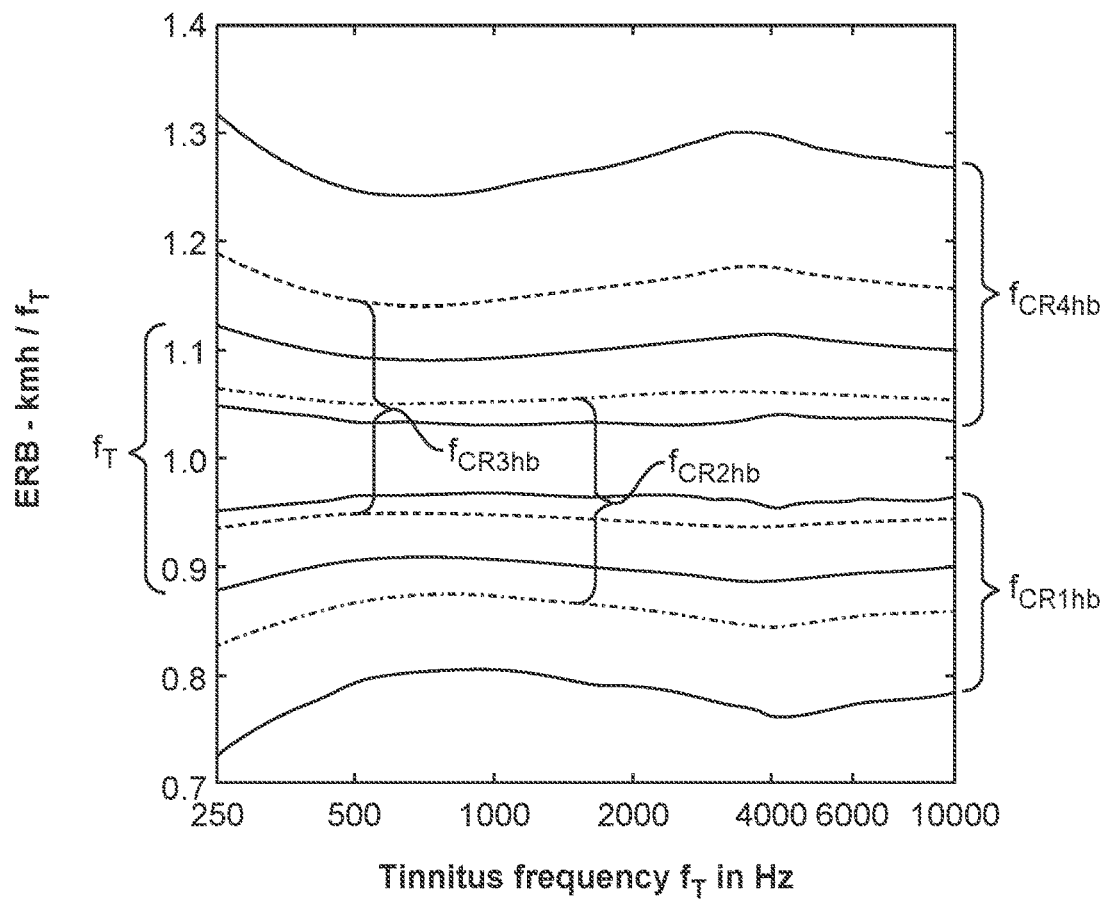
Figure 22:
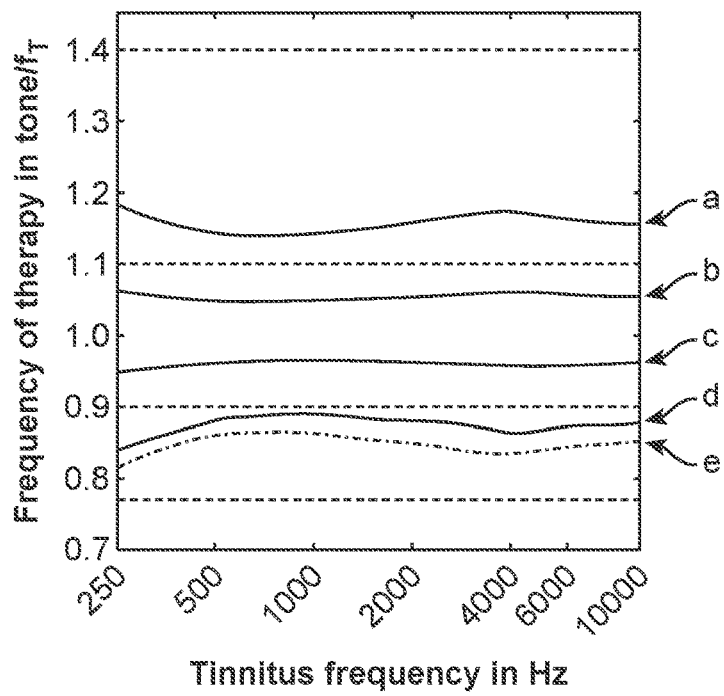
Figure 23:
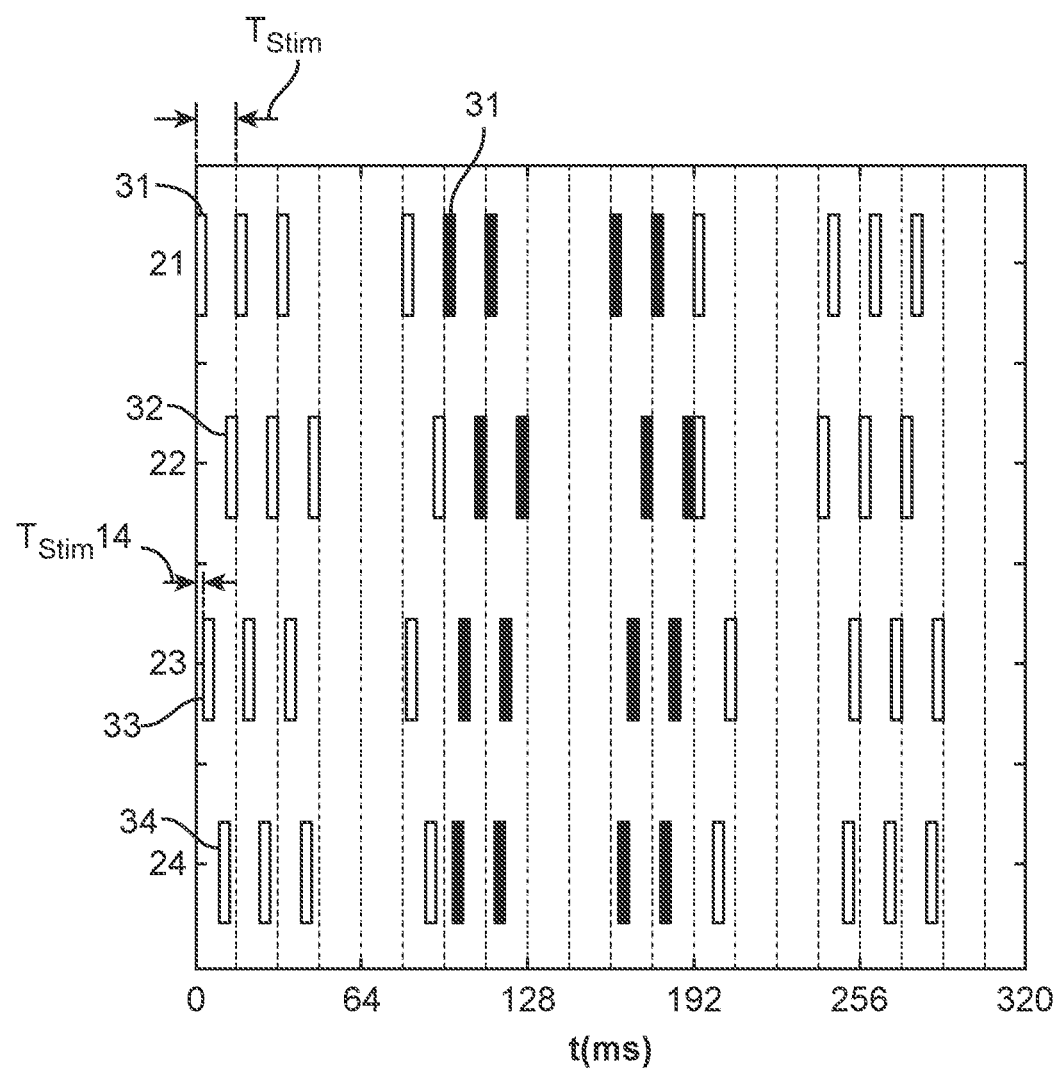
Figure 24:
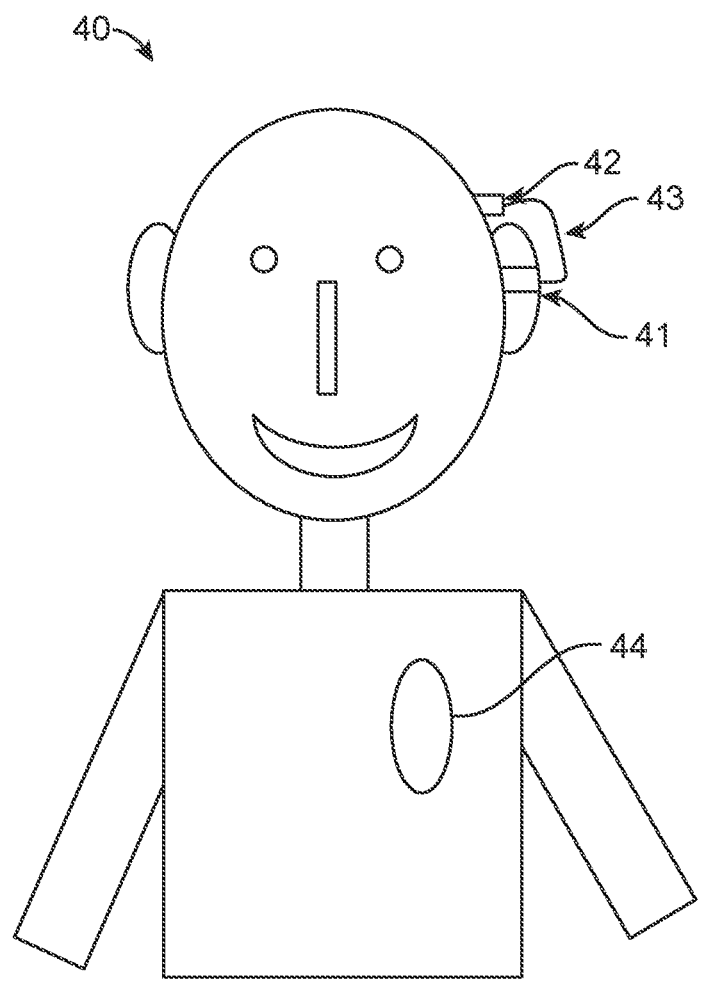
Figure 25:
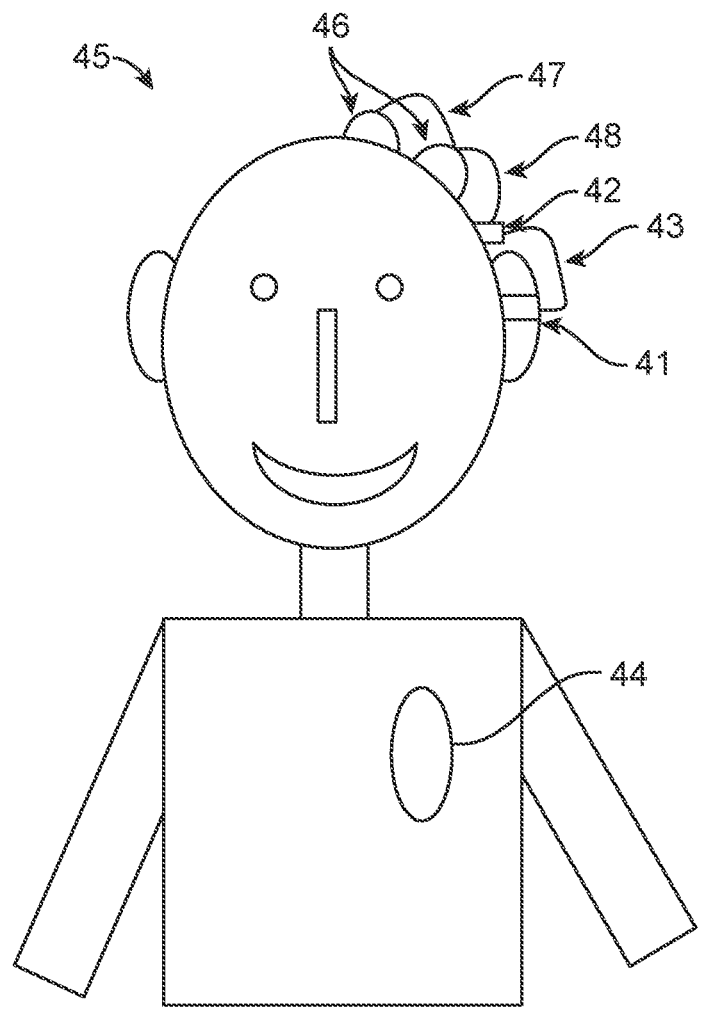
Figure 26:
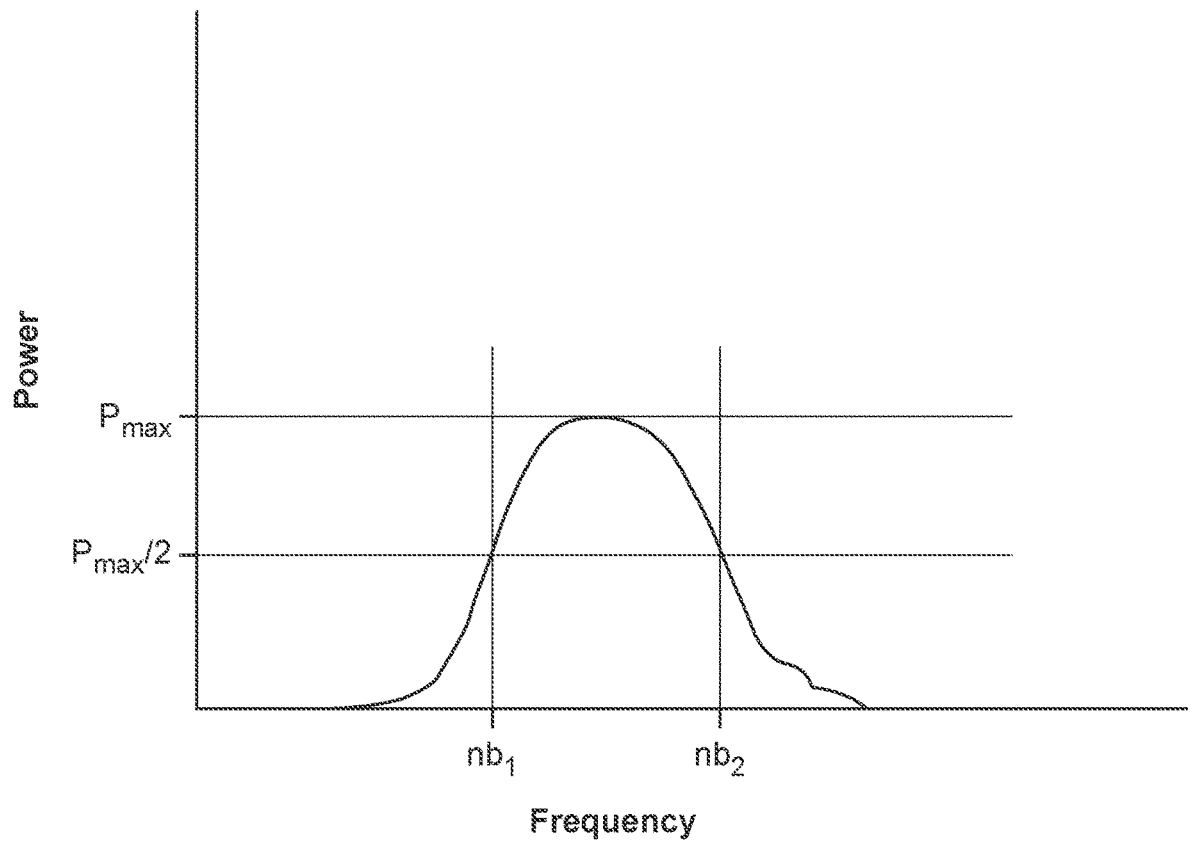
Figure 27:
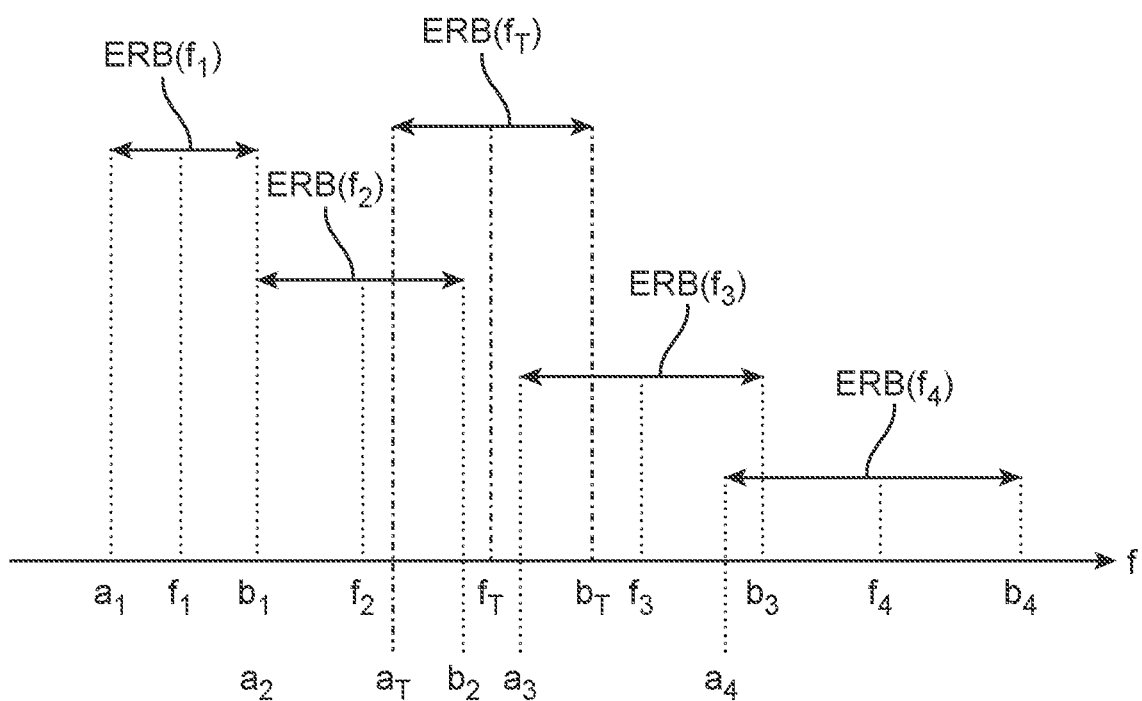
Figure 28:
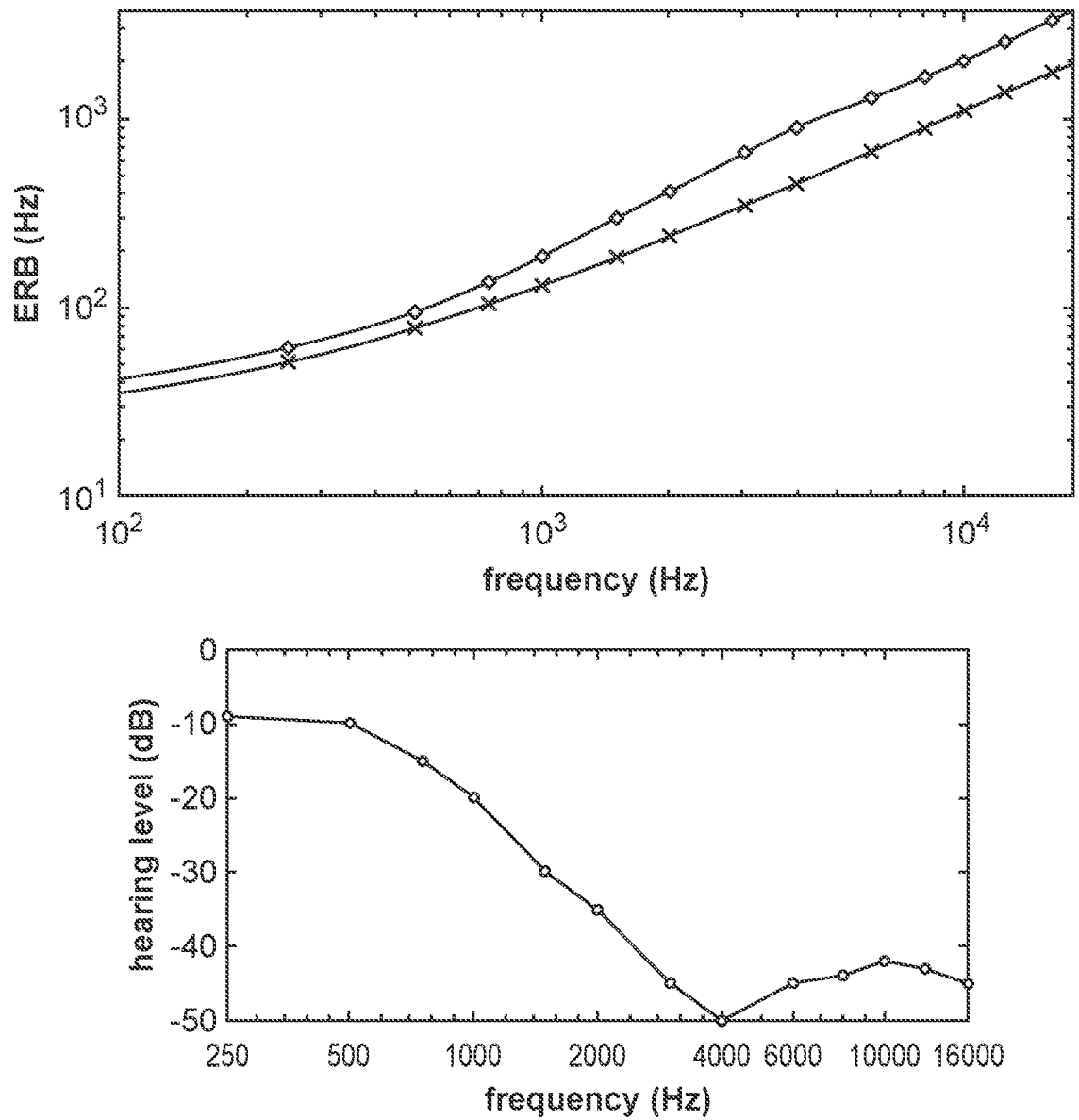
Figure 29:
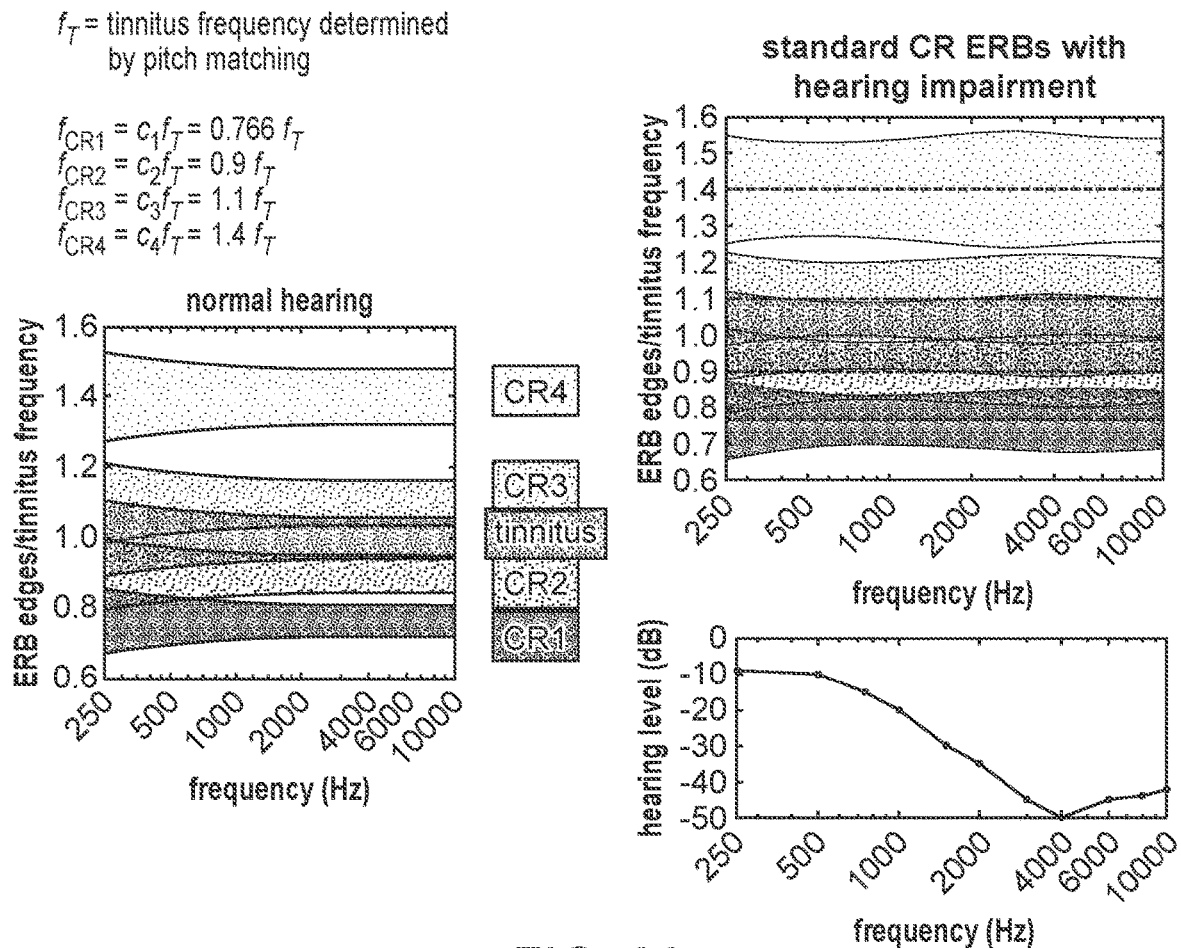
Figure 30:
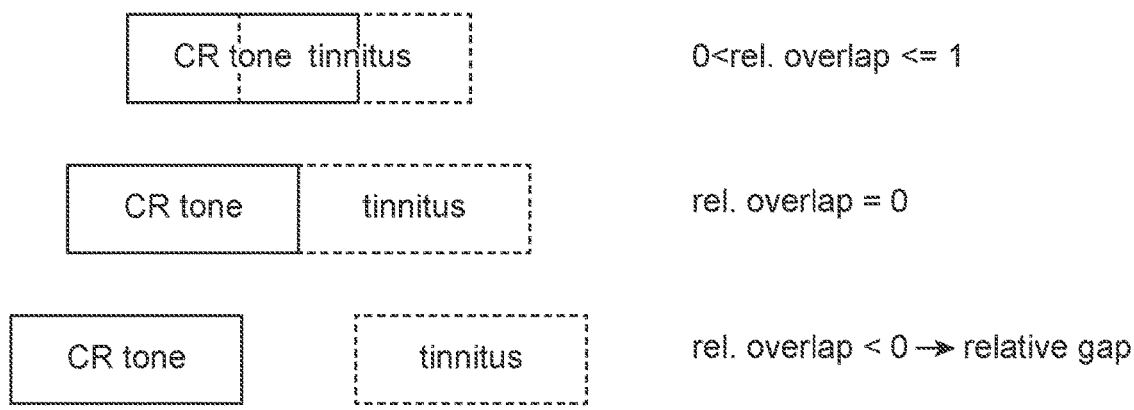
Figure 31:
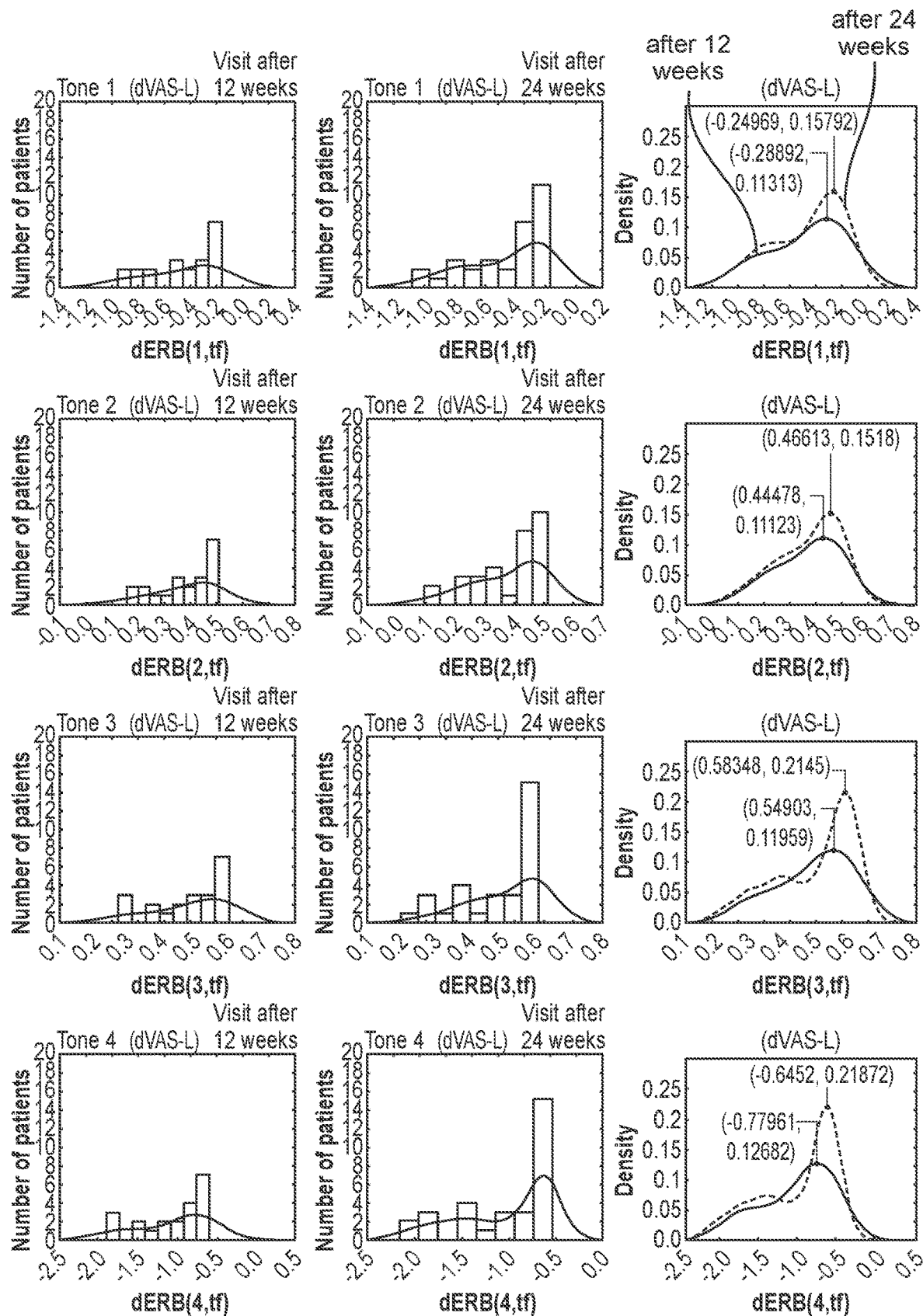
Figure 32:
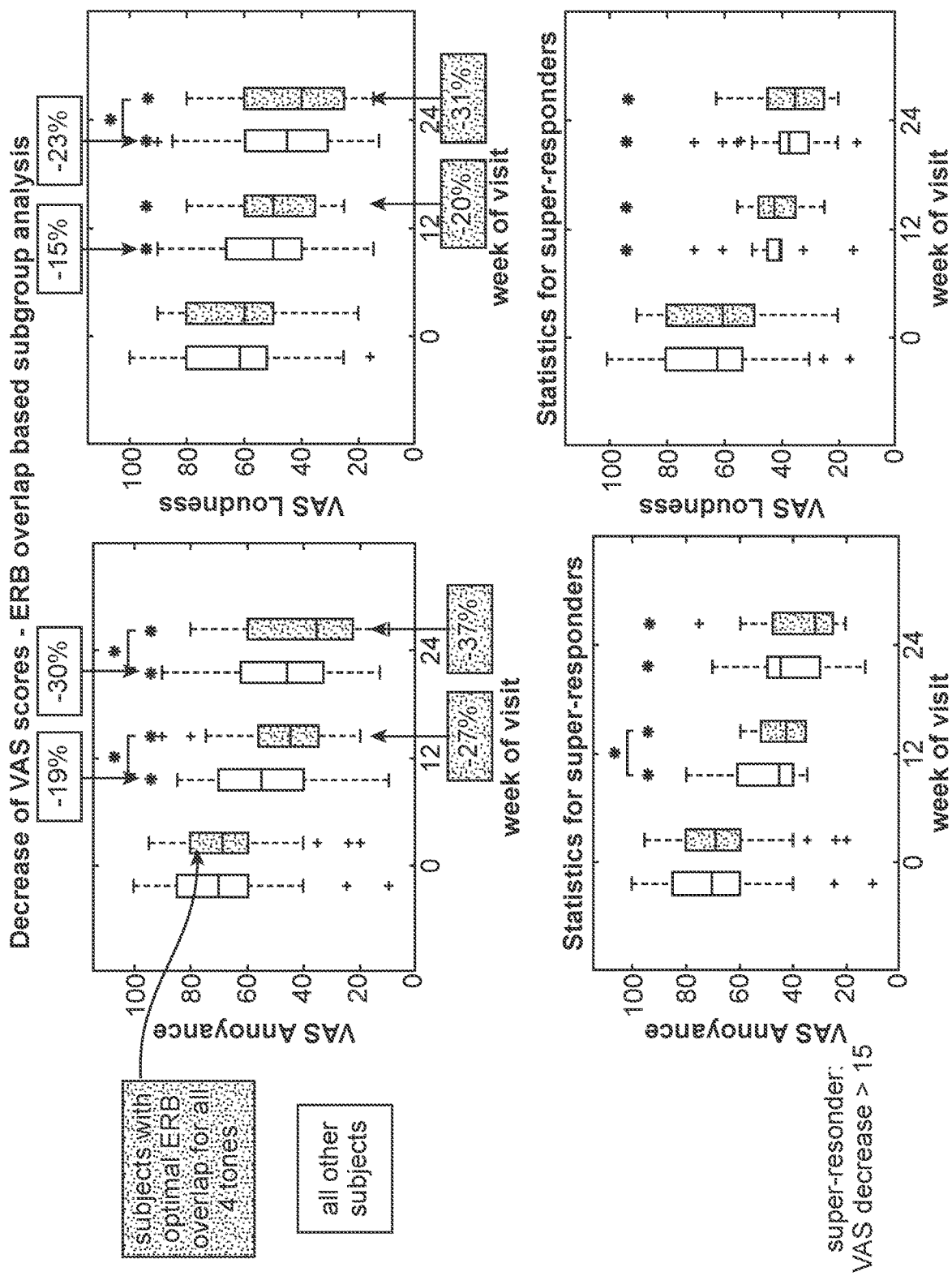
Figure 33:
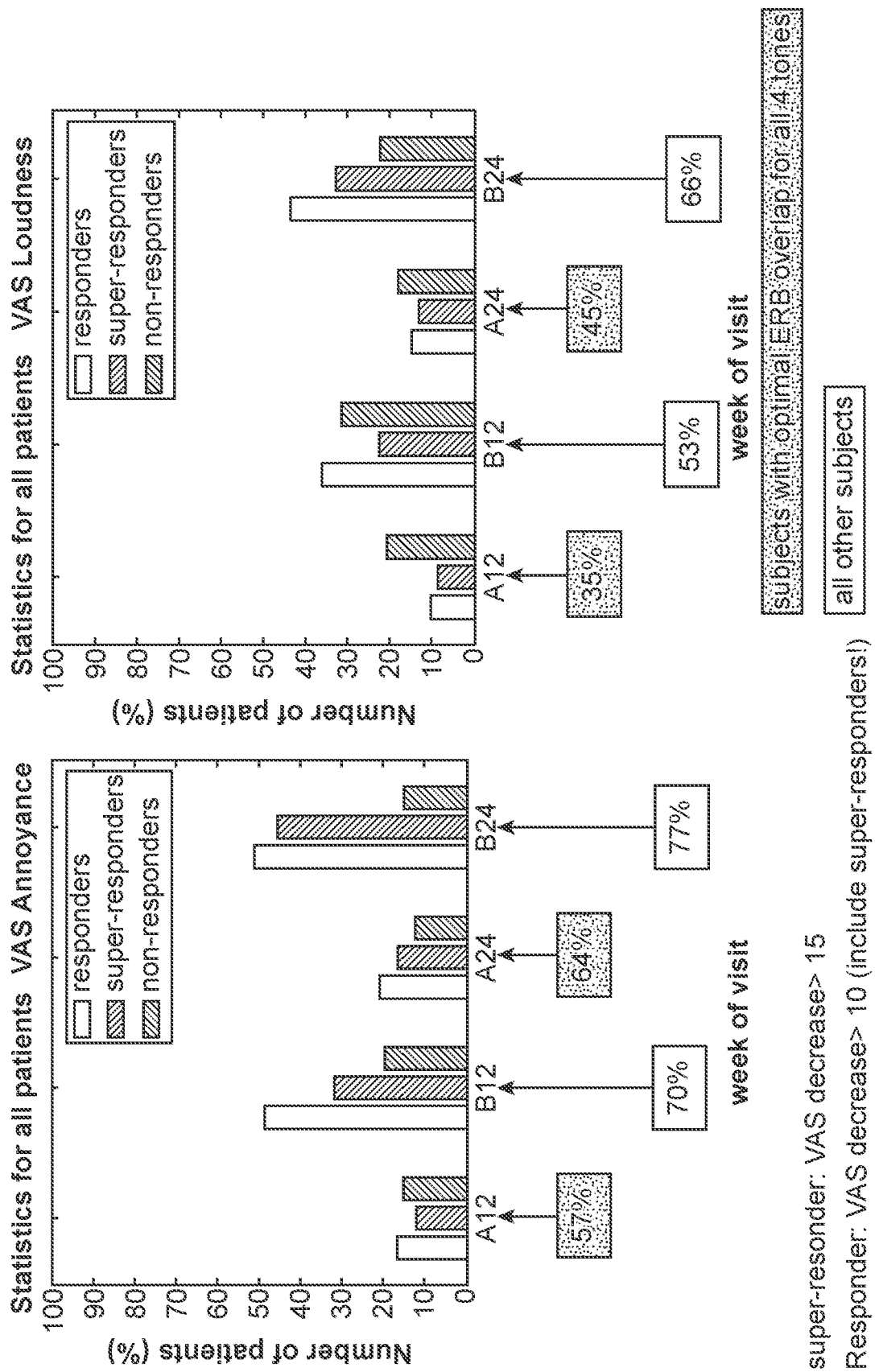
Figure 34:
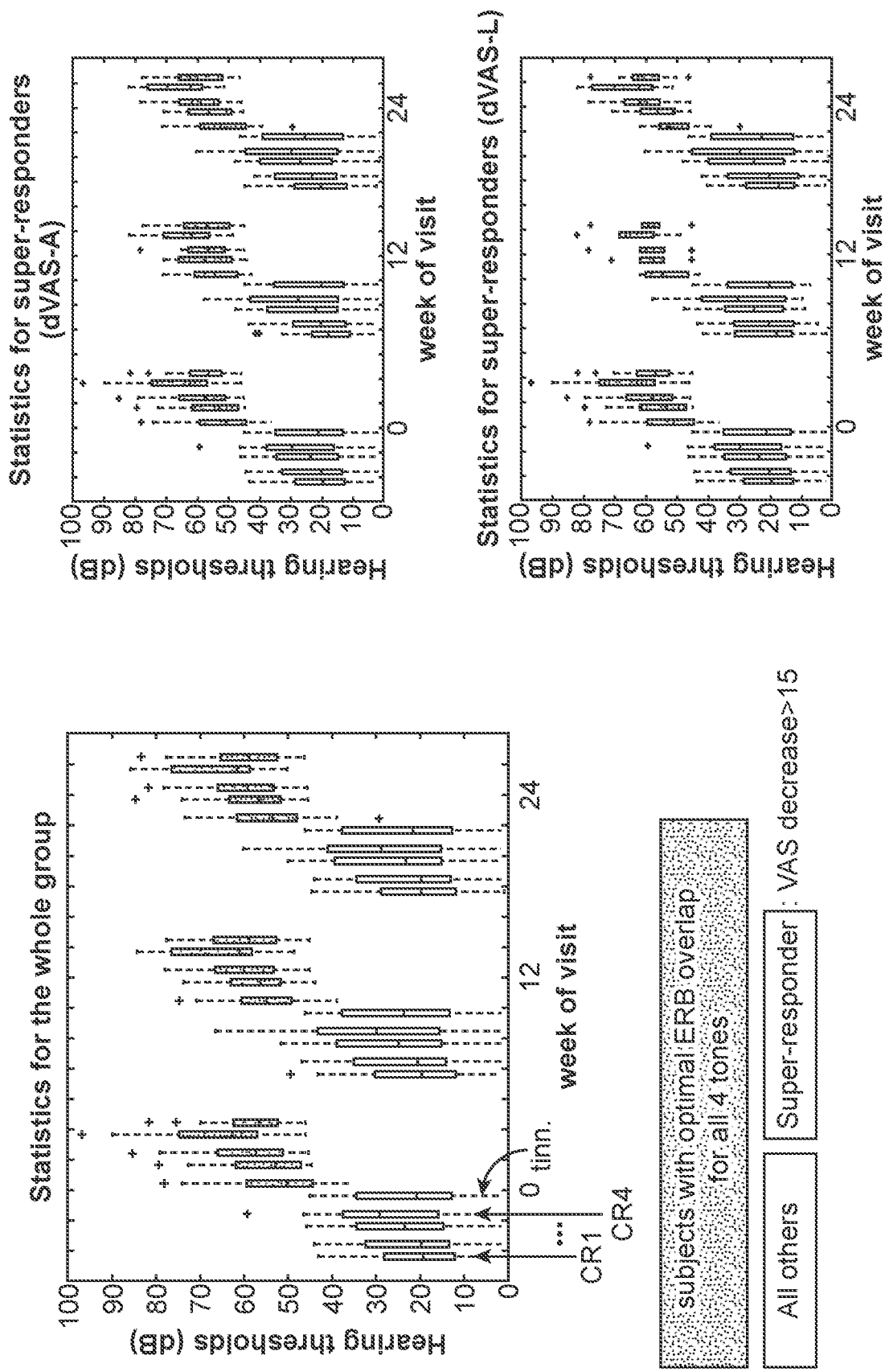
Figure 35:
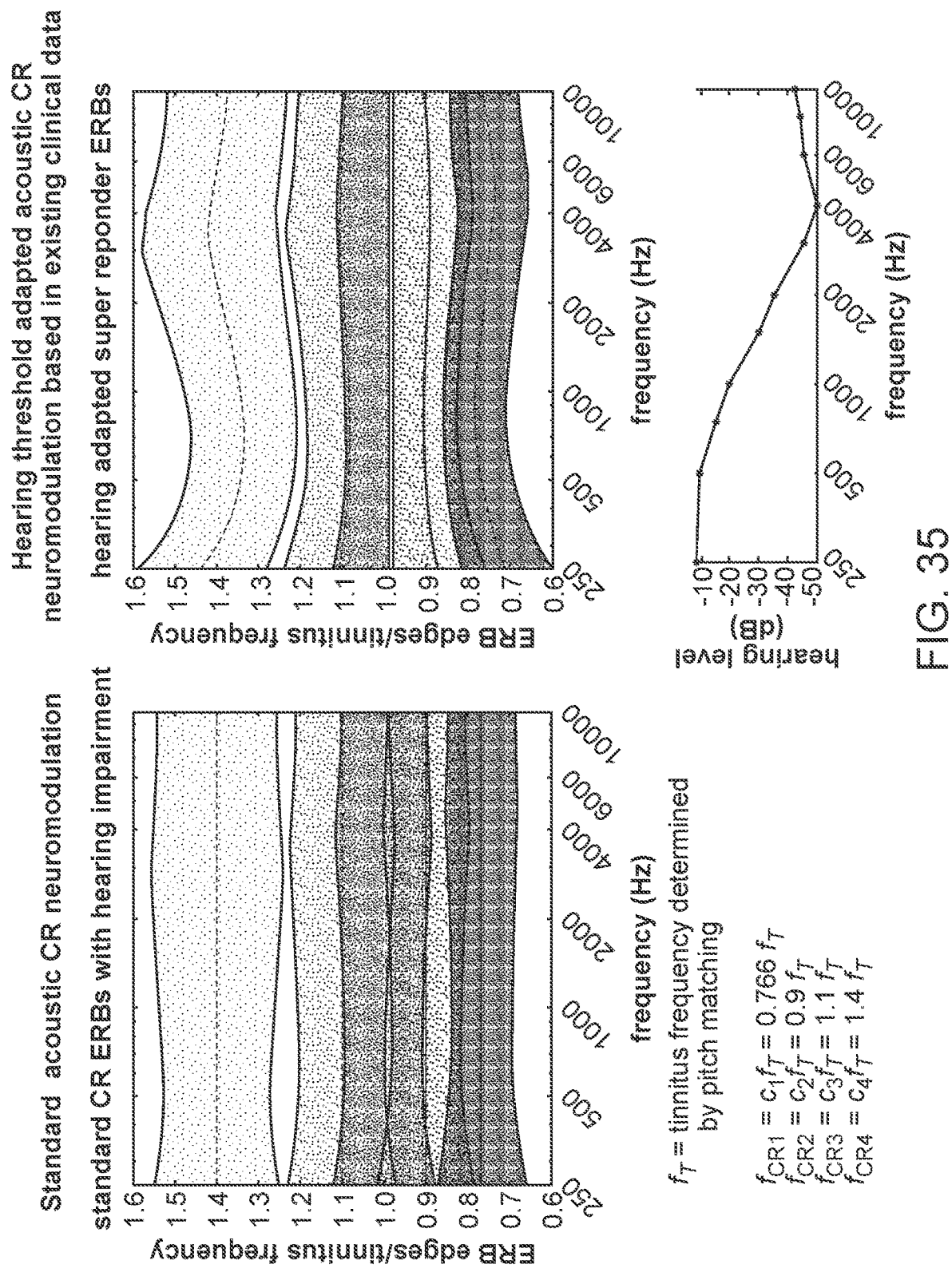

FIG. 11 shows a diagram to illustrate the ERB overlap as a function of frequency;

FIG. 12 shows a schematic diagram of a device for stimulation of a patient with acoustic stimulation signals and for desynchronization of neurons with a pathological synchronous and oscillatory activity according to one embodiment;

FIG. 13 shows a flow chart to illustrate the procedure in determining the optimum arrangement of a predetermined number of therapy tones on the frequency axis;

FIG. 14 shows the diagram from FIG. 11 with points of intersection of the graph with optimum values for the relative ERB overlap to determine the frequencies of the therapy tones;

FIG. 15 shows a diagram to illustrate the ERB bandwidths of therapy tones determined from FIG. 14 as a function of the tinnitus frequency;

FIG. 16 shows a diagram to illustrate the personalized hearing threshold-adapted frequencies from the therapy tones determined from FIG. 14 as a function of the tinnitus frequency;

FIG. 17 and FIG. 18 show flow charts to illustrate the procedure in determining the optimum number of therapy tones and their optimum arrangement on the frequency axis according to a first variant;

FIG. 19 and FIG. 20 show flow charts to illustrate the procedure in determining the optimum number of therapy tones and their optimum arrangement on the frequency axis according to a second variant;

FIG. 21 shows a diagram to illustrate the ERB bandwidths for the personalized tinnitus ERB-centered hearing threshold-adapted and balanced arrangement of the therapy tones as a function of the tinnitus frequency;

FIG. 22 shows a diagram to illustrate the personalized tinnitus ERB-centered hearing threshold-adapted and balanced frequencies of the therapy tones as a function of the tinnitus frequency;

FIG. 23 shows a schematic diagram of an acoustic CR stimulation;

FIG. 24 shows a first schematic diagram of a device for stimulation of a patient with acoustic stimulation signals according to another embodiment;

FIG. 25 shows a schematic diagram of a device for stimulation of a patient with acoustic stimulation signals according to yet another embodiment;

FIG. 26 shows a schematic diagram of a complex acoustic stimulation signal;

FIG. 27 shows notations of band edges and center frequencies of ERBs and each of the four CR tones as an example;

FIG. 28 (upper plot) shows the ERB at normal hearing (thin line) as well as the hearing threshold adapted ERB (solid line). Symbols indicate frequencies at which the audiogram was measured. Lower plot shows the corresponding audiogram (linearly interpolated on a logarithmic frequency axis);

FIG. 29 provides the ERBs of the standard CR tones together with the tinnitus ERB for a normal hearing case (left plot) as well as an example for hearing threshold adapted ERBs (upper right plot) and the corresponding hearing threshold (lower right plot). ERBs are illustrated by plotting ERB edges divided by tinnitus frequency;

FIG. 30 illustrates the calculation of relative ERB overlap;

FIG. 31 displays the distributions of the number of super responders, e.g., the subjects with VAS for loudness (VAS-L) changes >15 (y-axis) in relation to $\rho(f_T, f_j)$ for all four CR tones $f_1, \ldots, f_4$ (rows 1, ..., 4) after 12 weeks (column 1) and after 24 weeks (column 2) and the corresponding distributions obtained by a standard smoothing procedure (column 3);

FIG. 32 shows the subgroup analysis for the two different groups (patients with/without relative optimal ERB overlaps for all 4 CR tones);

FIG. 33 shows results of a subgroup analysis of responder rates;

FIG. 34 displays results of a subgroup analysis of hearing thresholds at CR tones $f_1, \ldots, f_4$ and at the tinnitus frequency $f_T$;

FIG. 35 shows ERBs of standard CR tones together with the tinnitus ERB (left panel, same as right panel in FIG. 29) for a patient with typical hearing loss (lower right panel). In contrast, the right panel shows the hearing threshold adapted ERBs in the same patient (with hearing loss as in the lower right panel) and optimal ERB overlaps (as determined from a re-analysis of clinical data); and FIG. 36 displays an example of an ERB arrangement for tinnitus ERB stretching factor σ=1.5 (upper panel) for a patient with typical hearing loss (lower panel). The results are obtained with the procedure described in the text.

DETAILED DESCRIPTION

Chronic subjective tinnitus occurs in approx. 10% to 15% of the average population (cf. document D8). The quality of life of approx. 2% of the average population is greatly reduced because of their tinnitus. Therefore, this portion of the population will seek professional help (cf. documents D5 and D15). Subjective tinnitus is characterized by pathological synchronous neural activity. Chronic subjective tinnitus is associated with altered spectral performance of EEG (electroencephalography) and MEG (magnetoencephalography) signals formed by a large network of regions of the brain, in particular in the temporal cortex (cf. documents D3, D4, D9, D20, D22, D23 and D25).

Tinnitus as well as other neurologic or psychiatric diseases, which are described further below and can be treated with the help of the present disclosure, may be caused by a disturbance in the bioelectric communication of neural ensembles that are formed in specific circuits. A neural population in the brain and/or spinal cord of a patient here constantly generates pathological neural activity and might even create an associated pathological connectivity (network structure). In doing so, a large number of neurons form synchronous action potentials, namely the neurons involved fire excessively in synchronization. Furthermore, the pathological neural population has an oscillatory neural activity, namely the neurons also fire rhythmically. In the case of neurologic or psychiatric diseases, the average frequency of the pathological rhythmic activity of the neuron ensembles thereby affected is approximately in the range of 1 to 30 Hz but may also be outside this range. In healthy people, however, neurons fire in a qualitatively different manner, e.g., in an uncorrelated manner.

Acoustic "coordinated reset" (CR) stimulation is a treatment using acoustic stimulation signals for treating subjective tinnitus (cf. document D22). Acoustic CR stimulation counteracts the pathological synchronous neural activity associated with tinnitus by desynchronization. The success of this treatment can be verified by way of EEG measurements (cf. document D3, D4, D20 and D22). A feasibility study ("proof of concept trial") has yielded statistically and clinically significant therapeutic effects of acoustic CR therapy (cf. documents D1, D2 and D22). The observations on which the study is based were then repeated in a large-scale study with 200 patients at 23 clinic sites (cf. document D12) and one observation study with 66 patients (cf. document D27).

In acoustic CR stimulation, therapy tones that are played for the patient are converted to nerve pulses in the inner ear and sent via the auditory nerve to the auditory cortex. Due to the tonotopic arrangement of the auditory cortex, a certain portion of the auditory cortex is activated by acoustic stimulation of the inner ear at a certain frequency. Therefore, certain regions of the auditory cortex can be stimulated in a targeted manner by a suitable choice of the frequencies of the therapy tones.

The therapy tones played for the patient in acoustic CR stimulation are designed so that the offset (or phase-shifted) stimulation induces desynchronization of the pathological synchronous and oscillatory activity of the neural population by way of at least two stimulation channels. A reduction in the rate of coincidence of the neurons caused by this stimulation can result in a reduction in the synaptic weights and can thus lead to learning of the tendency to production of pathological synchronous activity.

The therapy tones perceived by the patient via at least one ear cause a so-called reset in the neural population of the phase of neural activity of the stimulated neurons. This reset causes the phase of the stimulated neurons to be set at one or almost one certain phase value, e.g., 0°, regardless of the prevailing phase value (in practice it is difficult to accurately set a certain phase value, but this is not necessary for successful CR stimulation). Thus, the phase of neural activity of the pathological neural population is controlled by way of targeted stimulation. The pathological neuron population is stimulated at different locations by way of multiple stimulation channels, so the phases of neural activity of the subpopulations of pathological neuron population stimulated by the different stimulation channels can be reset at different points in time by applying the therapy tones with a time lag. As a result, the pathological neuron population, whose neurons were previously in synchronization and were active with the same frequency and phase, is split into multiple subpopulations with different phases. Within each of the subpopulations, the neurons are still in synchronization even after the reset and they continue to fire at the same pathological frequency, but with respect to its neural activity, each subpopulation has the phase forced on it by the stimulus generated by the respective stimulation channel. This means that, even after their phases have been reset, the neural activities of the individual subpopulations still have an approximately sinusoidal curve with the same pathological frequency but different phases.

Due to the pathological interaction between the neurons, the condition created by the stimulation with at least two subpopulations is unstable, and the entire neural population rapidly approaches a condition of complete desynchronization, in which the neurons fire in an uncontrolled manner. The desired condition, namely complete desynchronization, usually does not exist immediately after the time-offset (or phase shifted) application of the therapy tones with a time lag (or a phase shift) but instead is usually established within a few periods or even less than one period of the pathological frequency.

One theory to explain the success of stimulation is based on that the desynchronization, which is ultimately the goal, is made possible at all due to the pathologically enhanced interactions among the neurons. This makes use of a self-organization process, which is responsible for the pathological synchronization. One effect of this is that a division of an overall population into subpopulations with different phases is followed by desynchronization. In contrast with that, without a pathologically enhanced interaction of neurons, no desynchronization would be possible.

Furthermore, through CR stimulation, a reorganization of the connectivity of the disturbed neural networks can be achieved, so that long-lasting therapeutic effects are made possible. The synaptic reconstruction thereby achieved is important for effective treatment of neurologic or psychiatric disorders.

To counteract the pathological synchronous neural activity associated with tinnitus in the central auditory system, namely the primary auditory cortex, the frequency $f_T$, i.e., the pitch of the dominant tinnitus tone, is determined first in traditional acoustic CR stimulation according to the audiological characteristics of the respective patient, and then the amplitude, namely the loudness, of the four CR therapy tones to be reproduced for the patient is matched. The frequencies of the four CR therapy tones $f_{CR1}$, $f_{CR2}$, $f_{CR3}$ and $f_{CR4}$, which were used in the feasibility study (cf. document D22) and the following studies and are also used in clinical practice today, are as follows:

$$f_{CR1} = c_1 f_T = 0.766 f_T \quad (1)$$

$$f_{CR2} = c_2 f_T = 0.9 f_T \quad (2)$$

$$f_{CR3} = c_3 f_T = 1.1 f_T \quad (3)$$

$$f_{CR4} = c_4 f_T = 1.4 f_T \quad (4)$$

The frequency ratios $c_1$, $c_2$, $c_3$ and $c_4$ are fixed and are identical for all patients, regardless of their hearing thresholds.

All therapy tones are typically just above the hearing threshold of the respective patient but are comfortably audible. The loudness of the therapy tones is adjusted so that all four therapy tones are perceived at the same subjective loudness level which is slightly above the hearing threshold of the patient.

Figure 1:
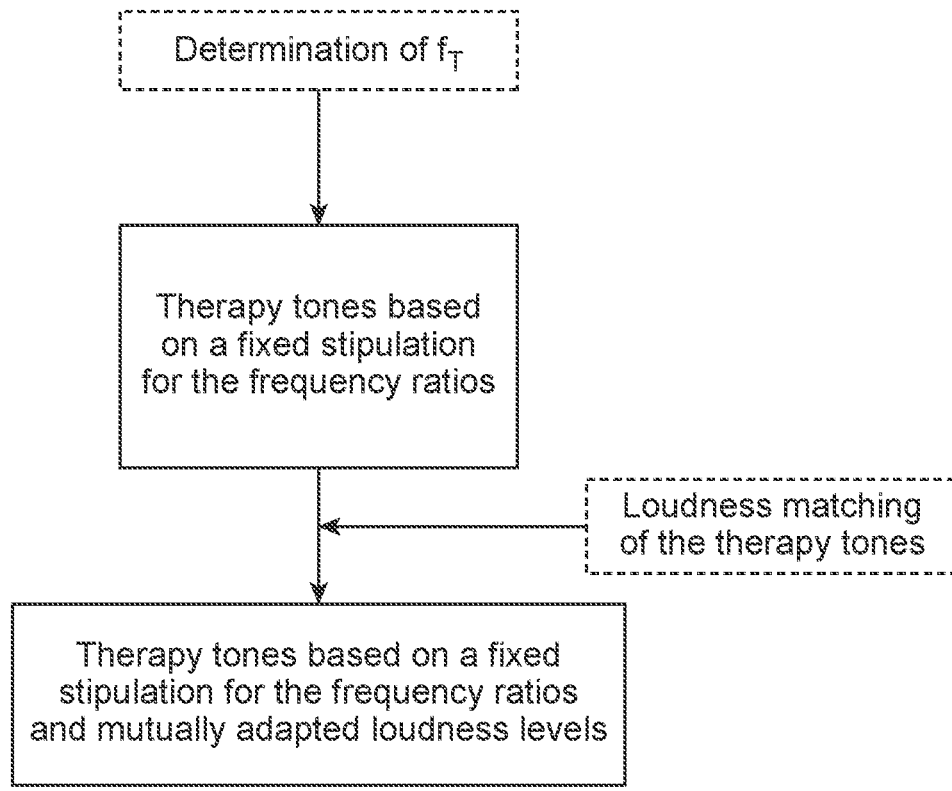
FIG. 1 shows a flow chart to illustrate a comparative acoustic CR therapy for treatment of a patient with tinnitus.

The flow chart in FIG. 1 illustrates schematically a comparative (traditional) acoustic CR therapy for treatment of tinnitus. First, the dominant or most pronounced tinnitus frequency or that perceived as the most annoying for the patient is determined. The therapy tones are then calculated on the basis of the fixed frequency ratios $c_1$, $c_2$, $c_3$ and $c_4$, which are the same for all patients. A loudness comparison is then performed in order to adjust the loudness of the four therapy tones with respect to one another. FIG. 1 shows measurements performed on patients in boxes outlined with dotted lines, while data analysis, signal processing and sound production are shown in boxes outlined with solid lines.

From numeric simulations, CR stimulation supplies optimum desynchronization results if the stimuli are administered at different locations in the brain so that different subpopulations are stimulated (cf. documents D16 and D21). The overlap between the stimulated subpopulations should not be too great. On the other hand, the subpopulations should interact with one another adequately, namely the subpopulations should not be separated too much from one another spatially. In the area of direct electrical brain stimulation, e.g., deep brain stimulation, the dependence of the propagation of the stimulation current on the voltage or current has been investigated (cf. document D7). Accordingly, well-defined predictions have been made for the optimum stimulation amplitudes (cf. document D23) and verified (cf. documents D23 and D26).

For noninvasive auditory stimulation, the relationship between the stimulus and the activated neural population is more complicated. Cortical receptive regions as well as subcortical portions of the central auditory pathway are determined by the tonotopic organization of the auditory system and the auditory filter theory. The auditory filter theory is based on the concept of a center frequency and a bandwidth around the center frequency. The bandwidth of the auditory filters can be described based on the corresponding rectangular bandwidth, which is referred in the technical literature as ERB (equivalent rectangular bandwidth) (cf. documents D11 and D17). For reasons of simplicity and to allow quantitative comparisons across all auditory filter theories, the term equivalent rectangular bandwidth, or ERB, will be used to specify the relevant characteristics of any auditory filter including a center frequency (fc), a low cut-off frequency (fL) and a high cut-off frequency fH. The low and high cut-off frequencies determine the frequency bandwidth (fH−fL) that corresponds to the functional bandwidth of any auditory filter.

In patients with normal hearing ability, namely without hearing damage, the relationship between the ERB and the center frequency is described by approximations that have been verified experimentally (cf. documents D11 and D17):

(i) According to the first approximation, the equation for the ERB of a patient with normal hearing ability is as follows (cf. document D17):

$$ERB_N(\tilde{f}) = 6.23\tilde{f}^2 + 93.39\tilde{f} + 28.52 \quad (5)$$

where $\tilde{f}$ is the frequency in kHz, namely $f = \tilde{f} \cdot 1000$ where $f$ and $ERB_N$ are given in Hz. Consequently, this yields:

$$ERB_N(f) = \frac{6.23}{10^6} f^2 + \frac{93.39}{10^3} f + 28.52 \quad (6)$$

This approximation applies to frequencies f in the range of 100 Hz to 6.5 kHz.

(ii) The second ERB approximation is as follows (cf. document D11):

$$ERB_N(\tilde{f}) = 24.7(4.37 \cdot \tilde{f} + 1) \quad (7)$$

$\tilde{f}$ is the frequency in kHz, namely $f = \tilde{f} \cdot 1000$, where $f$ and $ERB_N$ are given in Hz. Therefore, this yields:

$$ERB_N(f) = \eta \cdot f + 24.7, \quad (8)$$

where $\eta = 107.939/1000$. This approximation is valid for moderate sound levels and for frequencies f in the range of 100 Hz to 10 kHz. This frequency range is much larger than the frequency range of the first approximation. Therefore, the second approximation shall be used hereinafter. For frequencies greater than 10 kHz, equation (8) is used for extrapolation.

In addition, the effect of a patient's hearing loss on the ERB can also be taken into account. Document D18 provides data for 2 kHz, 4 kHz and 6 kHz as well as absolute threshold values between 0 and 80 dB HL. Based on this data, the dependence of ERB on hearing loss can be modeled according to the following equation in a first approximation for the range of 0 and 50 dB HL within the scope of embodiments of the present disclosure:

$$ERB(f,h) = ERB_N(f) \cdot c(h), \quad (9)$$

where ERB (f, h) indicates the ERB influenced by the hearing loss h at the frequency f, $ERB_N(f)$ indicates the ERB without hearing loss at the frequency f, and the term c(h) is specified as follows:

$$c(h) = \begin{cases} 1 + \dfrac{h}{50 \text{ dB } HL} & \text{for } 0 \le h \le 50 \text{ dB } HL \\ 2 & \text{for } h > 50 \text{ dB } HL \end{cases} \quad (10)$$

For frequency values that are different from 2 kHz, 4 kHz and 6 kHz, the model according to equation (10) can be interpolated and extrapolated. For example, an audiogram with a predetermined number of frequencies may be used for calculation of the term c(h) and may be interpolated and extrapolated accordingly. Alternatively, a Békésy audiogram using a continuous course may also be used.

Figure 2:
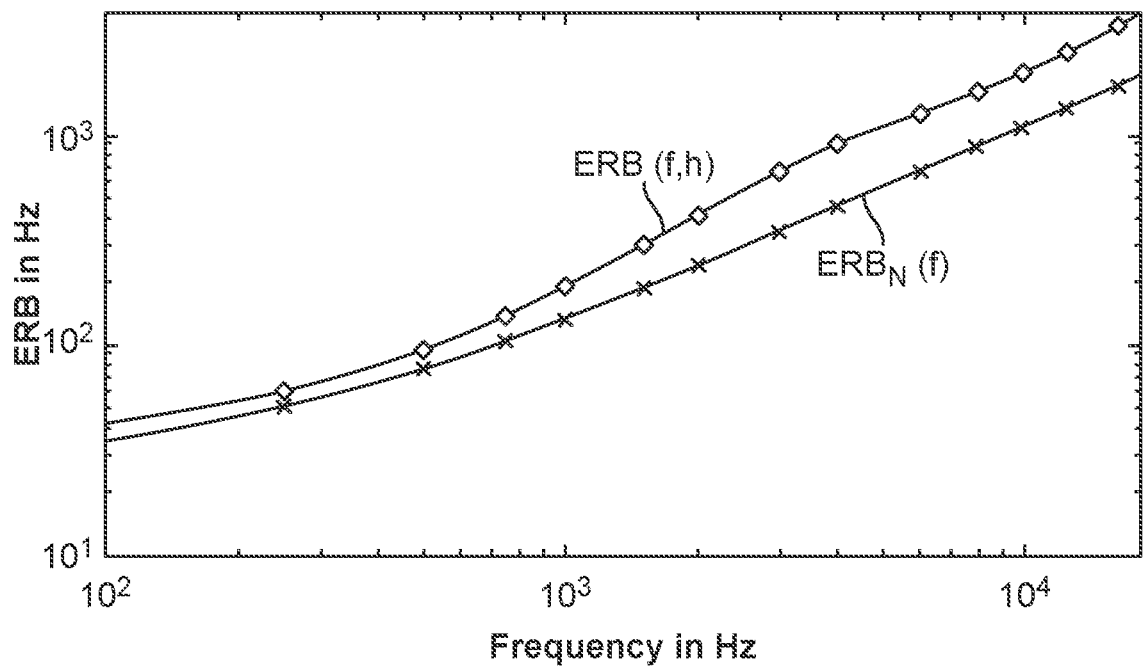
FIG. 2 shows a diagram to illustrate the bandwidth of an auditory filter as a function of the frequency for patients with and without a hearing impairment.

FIG. 2 shows the frequency dependence of the ERB without hearing loss ($ERB_N(f)$) and the ERB with hearing loss (ERB(f, h)). The values for the hearing thresholds to create FIG. 2 hearing threshold (namely the audiogram data) were recorded on a patient. The influence of the broadening of the ERB caused by a hearing threshold and defined by the term c(h) was raised in FIG. 2 by entering the values for $ERB_N(f)$ as crosses and for ERB(f, h) as diamonds into the diagram for the standard values for an audiogram at the frequencies 250 Hz, 500 Hz, 750 Hz, 1 kHz, 1.5 kHz, 2 kHz, 3 kHz, 4 kHz, 6 kHz, 8 kHz, 10 kHz, 12.5 kHz and 16 kHz. The hearing thresholds at these frequencies are 9, 10, 15, 20, 30, 35, 45, 50, 45, 44, 42, 43 and/or 45 dB HL.

Instead of the preceding model, the ERB bandwidths can also be measured on each patient individually at the tinnitus frequency, and the frequency of each frequency tone as well as at related interpolation points for the interpolation, for example, at the frequencies at which the audiogram, can also be determined. A variety of acoustic signals may be used to determine these individual ERB bandwidths, in particular tones, for example, sinusoidal frequency-modulated or amplitude-modulated tones or beeps, clicking sounds or noises such as white noise or bandpass-filtered noise with spectral or temporal gaps. The measurements comprise behavior responses which use a variety of psychoacoustic masking paradigms or physiological responses which in turn use a variety of evoked electric potentials or otoacoustic emissions. Each of the individualized ERB bandwidths includes the individual hearing threshold as well as above-threshold changes associated with the individual hearing loss.

The motivation for using the bandwidth concept and/or the ERB concept is illustrated schematically in FIGS. 3 through 6. It is assumed in these figures that the broadening of the ERB caused by the hearing loss will lead to an increase in the range and/or volume in the brain through which the respective therapy tones are activated. The influence of the broadening of the ERB caused by the hearing loss and the associated increase in the activated neural subpopulations on the therapy tones depend on the hearing loss by the respective patient as well as the interval of the therapy tones.

FIGS. 3 through 6 illustrate the organization of the primary auditory cortex along the frequency axis. In the patient's brain, at least one neural population 1 has a pathological synchronous and oscillatory neural activity, which thus causes the tinnitus, as described above. The neural population 1 should be desynchronized by targeted stimulation within the context of the CR therapy. Due to the four different therapy tones presented to the patient at the same loudness, four subpopulations 2, 3, 4 and 5 in the patient's brain are activated. The size of some populations 2 through 5 is determined by the ERB associated with the respective therapy tone.

Figure 3:
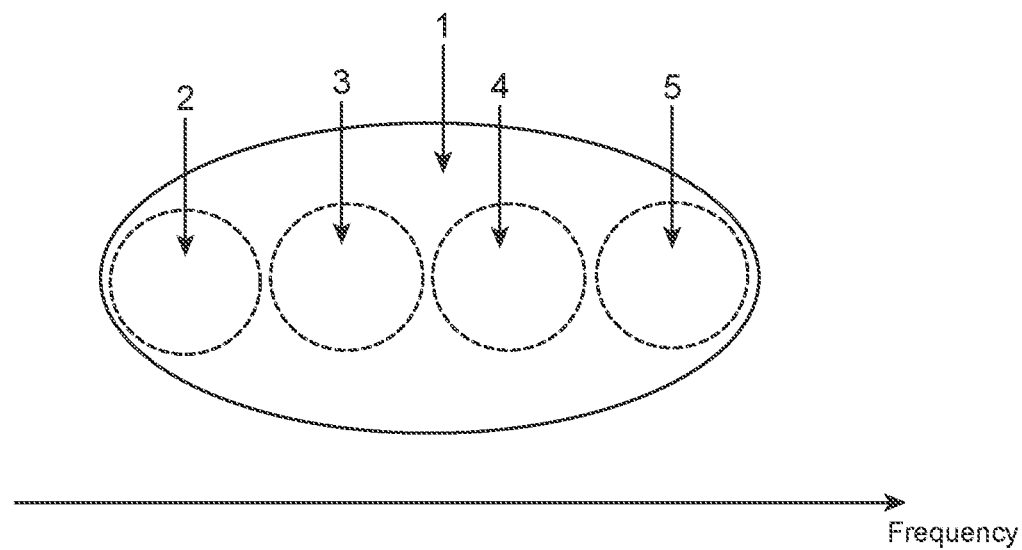
FIG. 3 shows a schematic diagram of a stimulated neural population in the primary auditory cortex of a patient with normal hearing ability.

FIG. 3 illustrates the case for a patient with normal hearing ability. For reasons of simplicity, all four subpopulations 2 to 5 here are the same size and neighboring subpopulations do not overlap with one another.

Figure 4:
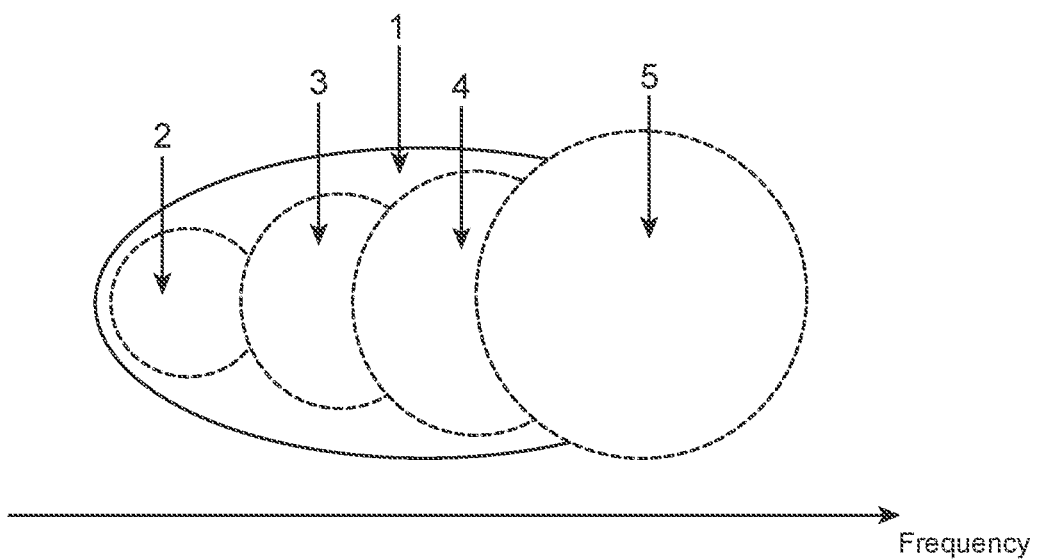
FIG. 4 shows a schematic diagram of a stimulated neural population in the primary auditory cortex of a patient with a hearing impairment.

In FIG. 4, the same therapy tones as in FIG. 3 are reproduced for the patient, but the ERBs for the three higher therapy tones have been broadened because of the hearing loss of one patient. This results in a significant overlap of the ERBs and therefore also the subpopulations. The overlap is especially pronounced between subpopulations 3 and 4 as well as subpopulations 4 and 5. Whereas good stimulation results could be achieved with the selected four therapy tones in the case of the stimulation illustrated in FIG. 3 in a patient with normal hearing ability, the overlap in subpopulations caused by the hearing loss is too great in FIG. 4 to allow a sufficient therapeutic success to be achieved.

Figure 5:
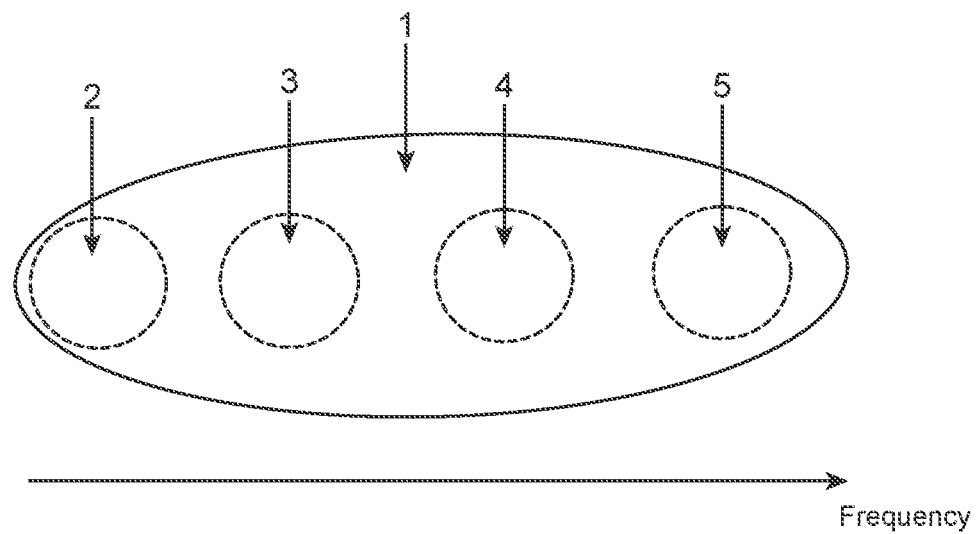
FIG. 5 shows a schematic diagram of the stimulated neural population from FIG. 3 with an enlarged frequency interval between neighboring therapy tones.
Figure 6:
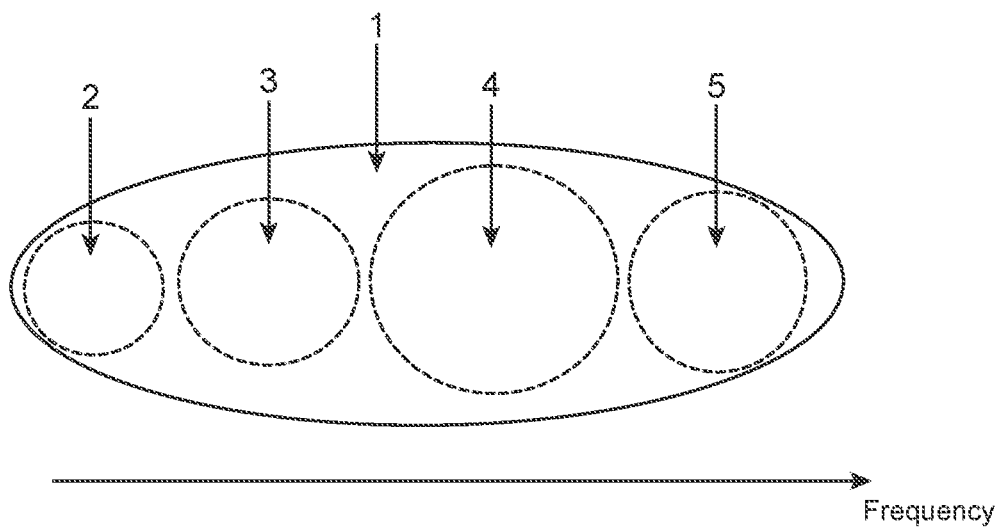
FIG. 6 shows a schematic diagram of the stimulated neural population from FIG. 4 with an enlarged frequency interval between neighboring therapy tones.

In FIGS. 5 and 6, the interval of the neighboring therapy tones has been increased. In the case of a normal hearing ability, subpopulations 2 through 5 are too far apart from one another, as shown in FIG. 5, so that the interaction between neighboring subpopulations and thus also the desynchronizing effect are reduced.

However, FIG. 6 shows that the increased interval of the neighboring therapy tones in the case of a patient with hearing loss results in subpopulations 2 through 5 no longer overlapping but being close enough together due to the increase in interval caused by the hearing loss that the subpopulations interact with one another to a sufficient extent to ensure the desired therapeutic success.

FIGS. 3 to 6 show that the interval between the therapy tones, which leads to good therapeutic results for a patient with normal hearing ability (cf. FIG. 3), may be unfavorable in a patient with a hearing loss, namely the therapy tones are too close together for the patient with hearing loss (cf. FIG. 4). Accordingly, therapy tones that are too far apart from one another for a patient with normal hearing ability (cf. FIG. 5) will lead to the desired therapeutic result in a patient with hearing loss (cf. FIG. 6).

It will be demonstrated below how the frequencies of the therapy tones can be selected, so that the neural subpopulations activated by the therapy tones overlap in such a way that the desired therapeutic success can be achieved.

In a first step, the ERB bandwidth is determined at a tinnitus frequency $f_T$, which was determined for a patient by a standard method, and the ERB bandwidths for the standard therapy tones $f_{CR1}$, $f_{CR2}$, $f_{CR3}$ and $f_{CR4}$ are considered according to equations (1) through (4). The coefficients $c_1$, $c_2$, $c_3$ and $c_4$ are given by $c_1=0.776$, $c_2=0.9$, $c_3=1.1$ and $c_4=1.4$. The therapy tones $f_{CR1}$, $f_{CR2}$, $f_{CR3}$ and $f_{CR4}$ of the standard therapy consequently cover half of an octave on each side of the tinnitus frequency $f_T$. The coefficients $c_1$, $c_2$, $c_3$ and $c_4$ of the standard therapy do not depend on the tinnitus frequency $f_T$ or on the hearing threshold.

Figure 7:
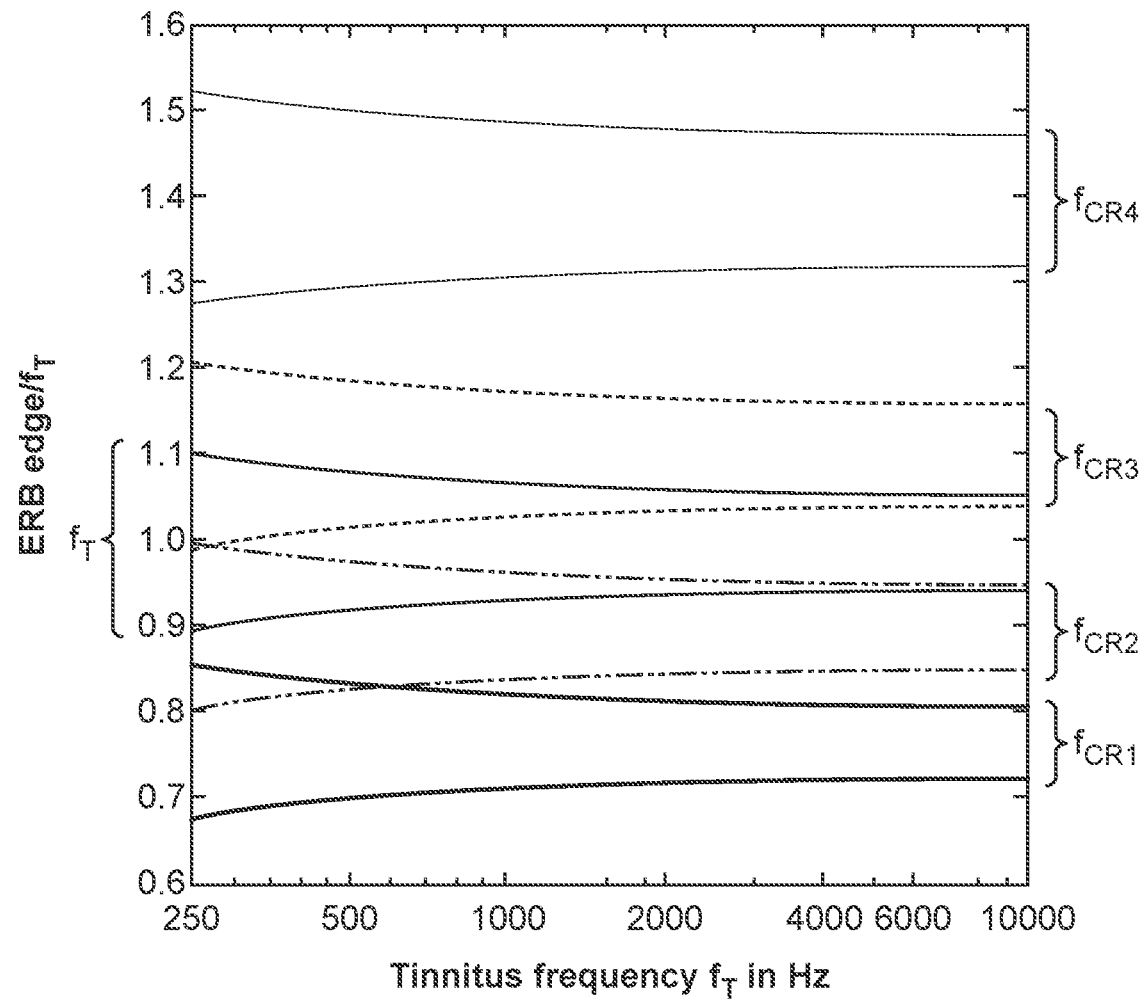
FIG. 7 shows a diagram to illustrate the ERB bandwidths of standard therapy tones as a function of the tinnitus frequency for normal hearing ability.
Figure 8:
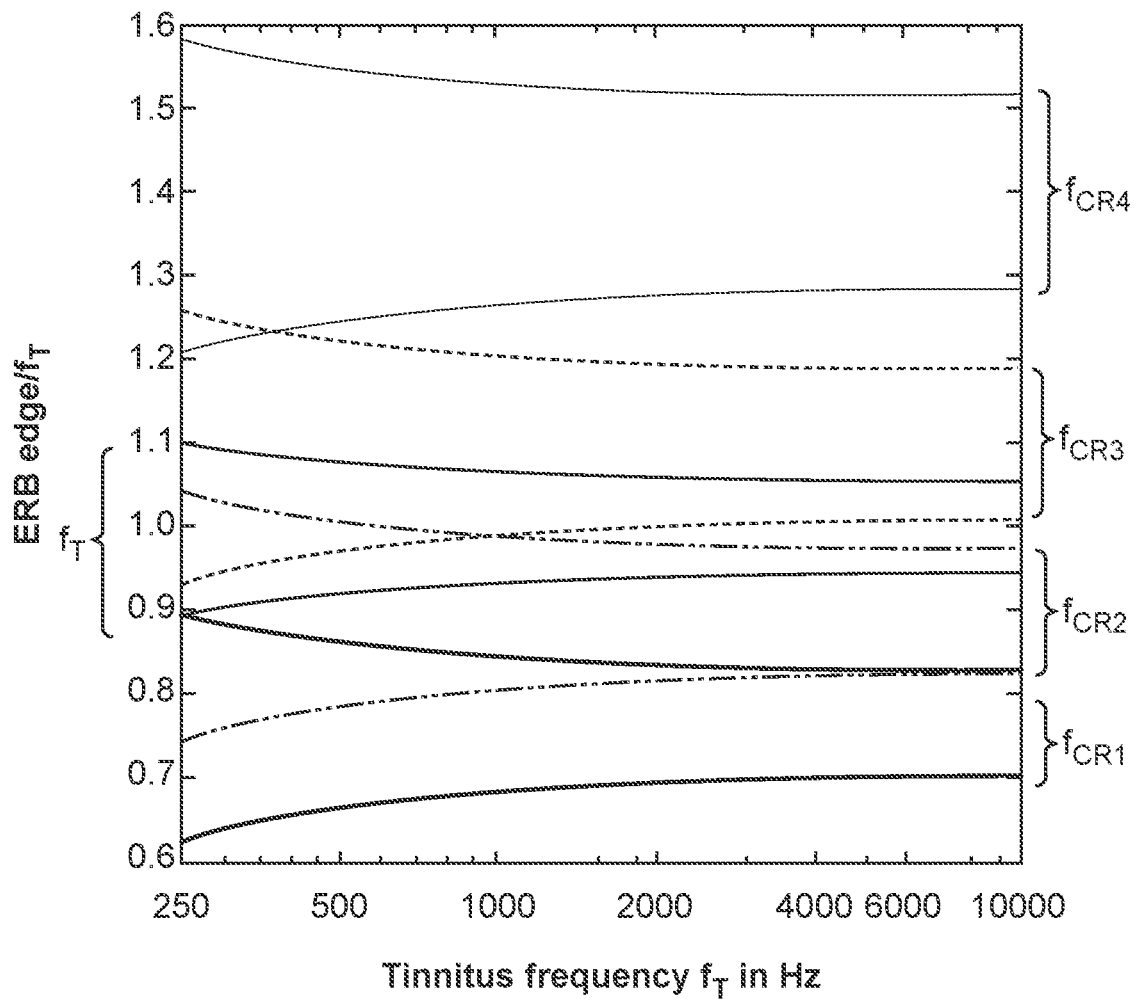
FIG. 8 shows a diagram to illustrate the ERB bandwidths of standard therapy tones as a function of the tinnitus frequency for a hearing impairment of 25 dB HL.
Figure 9:
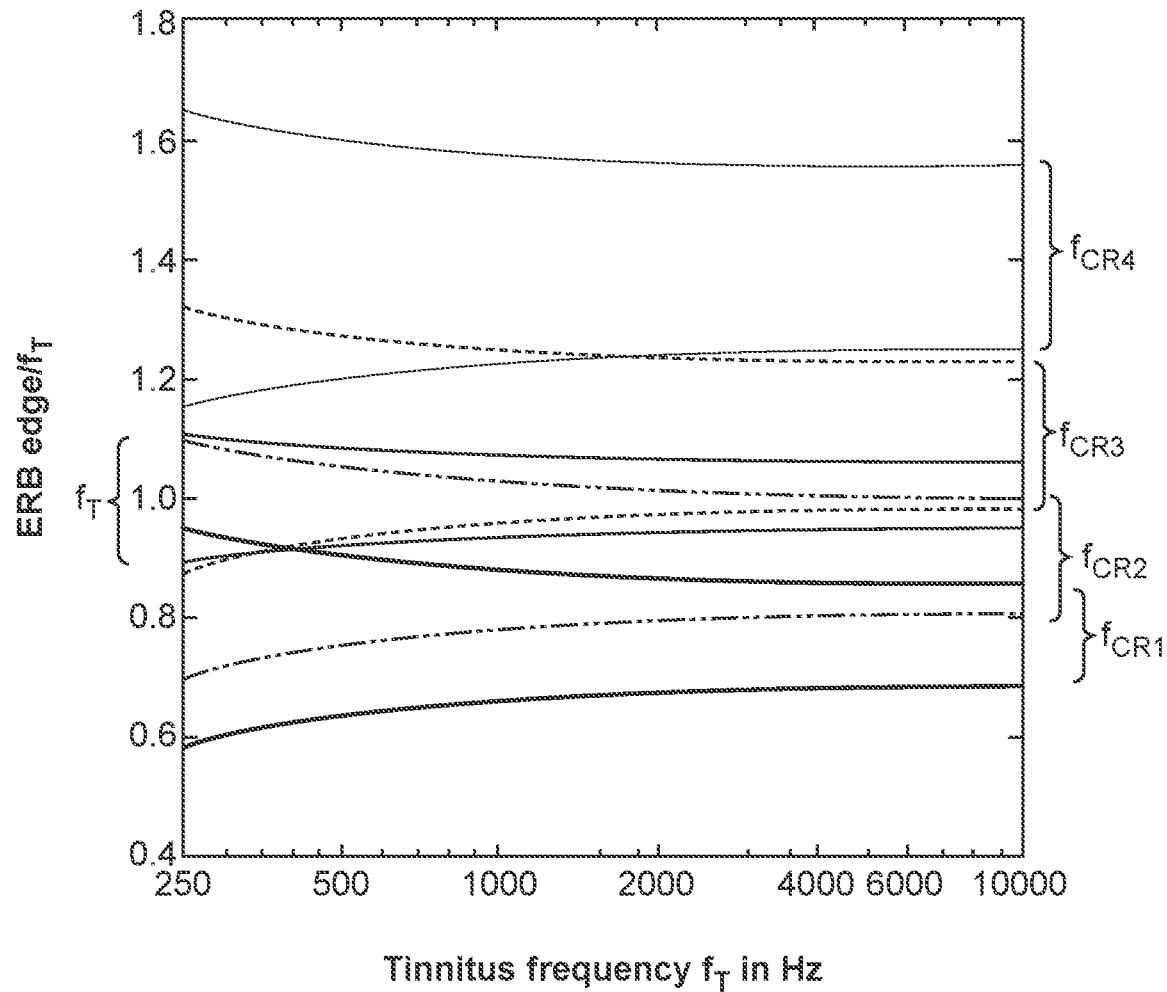
FIG. 9 shows a diagram to illustrate the ERB bandwidths of standard therapy tones as a function of the tinnitus frequency for a hearing impairment of 50 dB HL.

Assuming the patient's hearing loss is homogenous over the entire frequency axis, this then corresponds to a completely horizontal line in the audiogram. FIGS. 7 to 9 show how the ERB bandwidths belonging to the therapy tones $f_{CR1}$, $f_{CR2}$, $f_{CR3}$ and $f_{CR4}$ depend on the tinnitus frequency $f_T$ in the case of a normal hearing ability (cf. FIG. 7), a hearing loss of 25 dB HL (cf. FIG. 8) and a hearing loss of 50 dB HL (cf. FIG. 9). Therefore, in FIGS. 7 through 9, the ERB edges bordering the respective ERB are divided by the tinnitus frequency $f_T$ (cf. y axis) for the four therapy tones $f_{CR1}$, $f_{CR2}$, $f_{CR3}$ and $f_{CR4}$ as well as for the tinnitus frequency $f_T$, each plotted as a function of the tinnitus frequency $f_T$ (cf. X axis).

In FIG. 7, the hearing loss amounts to 0 dB HL over the entire frequency axis, namely the patient has a normal hearing ability and the respective audiogram has a flat horizontal curve. FIG. 7 shows the following ERB bandwidths from top to bottom in the order given:

ERB for the therapy tones $f_{CR4}=1.4f_T$ with ERB edges at $c_4 \pm 0.5$ ERB ($f_{CR4}$, 0 dB HL) represented by solid lines, ERB for the therapy tones $f_{CR3}=1.1f_T$ with ERB edges at $c_3 \pm 0.5$ ERB ($f_{CR3}$, 0 dB HL) represented by dotted lines, ERB for the tinnitus frequency $f_T$ with ERB edges at $1 \pm 0.5$ ERB ($f_T$, 0 dB HL) represented by solid lines, ERB for the therapy tone $f_{CR2}=0.9f_T$ with ERB edges at $c_2 \pm 0.5$ ERB ($f_{CR2}$, 0 dB HL) represented by dash-dot lines and ERB for the therapy tone $f_{CR}1=0.766f_T$ with ERB edges at $c_1 \pm 0.5$ ERB ($f_{CR1}$, 0 dB HL) represented by solid lines.

In FIG. 8 the hearing loss amounts to 25 dB HL over the entire frequency axis, namely the respective audiogram is a flat horizontal line. The following ERB bandwidths are represented in FIG. 8 from top to bottom in the order given:

ERB for the therapy tones $f_{CR4}=1.4f_T$ with ERB edges at $c_4 \pm 0.5$ ERB ($f_{CR4}$, 25 dB HL) represented by solid lines, ERB for the therapy tones $f_{CR3}=1.1f_T$ with ERB edges at $c_3 \pm 0.5$ ERB ($f_{CR3}$, 25 dB HL) represented by dotted lines, ERB for the tinnitus frequency $f_T$ with ERB edges at $1 \pm 0.5$ ERB ($f_T$, 25 dB HL) represented by solid lines, ERB for the therapy tone $f_{CR2}=0.9f_T$ with ERB edges at $c_2 \pm 0.5$ ERB ($f_{CR2}$, 25 dB HL) represented by dash-dot lines and ERB for the therapy tone $f_{CR}1=0.766f_T$ with ERB edges at $c_1 \pm 0.5$ ERB ($f_{CR1}$, 25 dB HL) represented by solid lines.

FIG. 9 shows the hearing loss of 50 dB HL over the entire frequency axis, namely the respective audiogram is a flat horizontal line. In FIG. 9 the following ERB bandwidths are illustrated in the order given here from top to bottom:

ERB for the therapy tones $f_{CR4}=1.4f_T$ with ERB edges at $c_4 \pm 0.5$ ERB ($f_{CR4}$, 50 dB HL) represented by solid lines, ERB for the therapy tones $f_{CR3}=1.1f_T$ with ERB edges at $c_3 \pm 0.5$ ERB ($f_{CR3}$, 50 dB HL) represented by dotted lines, ERB for the tinnitus frequency $f_T$ with ERB edges at $1 \pm 0.5$ ERB ($f_T$, 50 dB HL) represented by solid lines, ERB for the therapy tone $f_{CR2}=0.9f_T$ with ERB edges at $c_2 \pm 0.5$ ERB ($f_{CR2}$, 50 dB HL) represented by dash-dot lines and ERB for the therapy tone $f_{CR}1=0.766f_T$ with ERB edges at $c_1 \pm 0.5$ ERB ($f_{CR1}$, 50 dB HL) represented by solid lines.

FIGS. 7 to 9 show that the overlap, namely the gap (and/or interval) between the ERB bands of two neighboring therapy tones and the overlap and/or gap between the ERB bandwidth at the tinnitus frequency $f_T$ and the ERB bandwidths of the therapy tones depend to a great extent on the tinnitus frequency $f_T$ and are not symmetrical or balanced at all relative to the tinnitus frequency $f_T$.

For example, the interval between the ERB of the therapy tone $f_{CR4}$ and the ERB of the therapy tone $f_{CR3}$ is much larger than the gap between the ERB of the therapy tone $f_{CR2}$ and the ERB of the therapy tone $f_{CR1}$ for a hearing loss of 0 dB HL (cf. FIG. 7). For a hearing loss of 25 dB HL, the ERBs of the therapy tones $f_{CR1}$ and the $f_{CR2}$ overlap because of the broadening of the ERB caused by the hearing loss (cf. FIG. 8), whereas there is still a gap between the ERBs of the therapy tones $f_{CR3}$ and $f_{CR4}$ for a tinnitus frequency $f_T$ greater than approx. 2000 Hz.

In addition, the ERB of the tinnitus frequency $f_T$ and the ERBs of the therapy tones $f_{CR2}$ and $f_{CR3}$ are each slightly greater than approx. 2000 Hz for a hearing loss of 0 dB HL and a tinnitus frequency $f_T$ (cf. FIG. 7). In contrast with that, the overlap between the ERB of the tinnitus frequency $f_T$ and the ERB of the therapy tones $f_{CR2}$ and/or $f_{CR3}$ for a hearing loss of 50 dB HL and a tinnitus frequency $f_T$ greater than approx. 2000 Hz is much greater (cf. FIG. 9). FIGS. 7 through 9 show that the ERBs of the standard therapy tones $f_{CR1}$, $f_{CR2}$, $f_{CR3}$ and $f_{CR4}$ are not balanced with respect to one another or with respect to the tinnitus frequency $f_T$.

Figure 10:
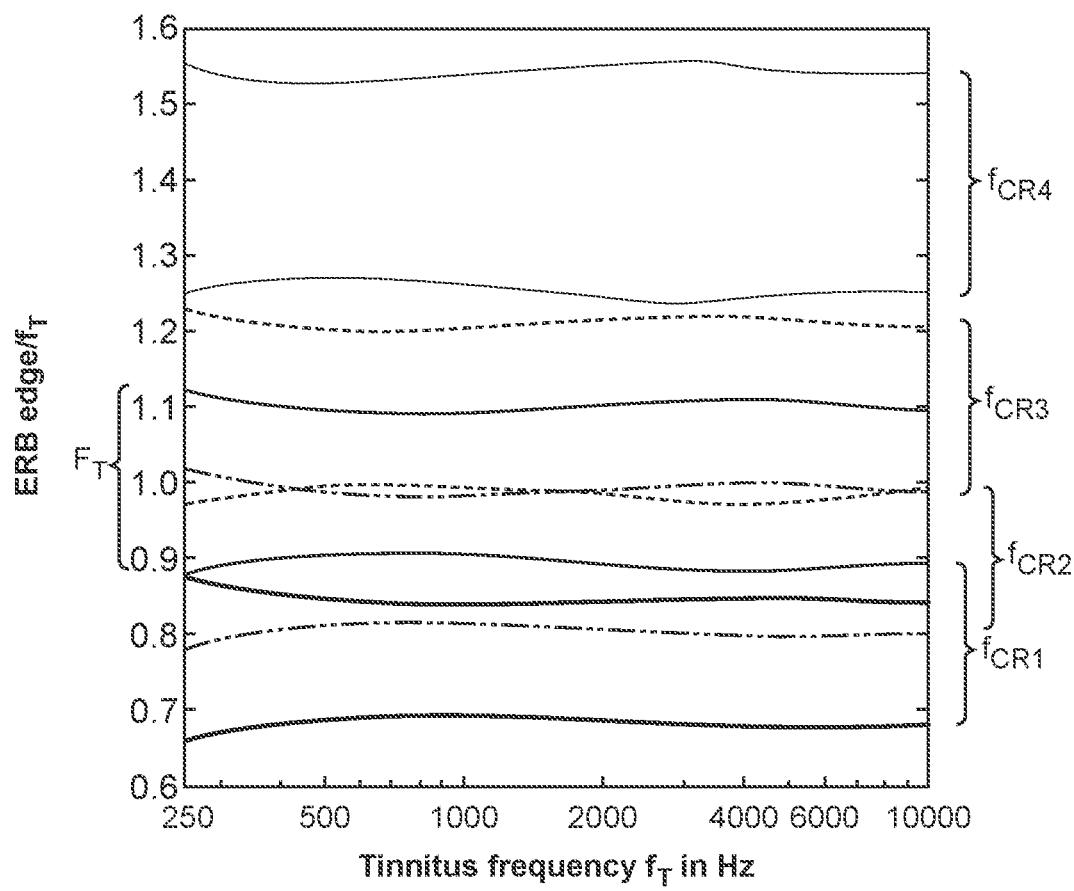
FIG. 10 shows a diagram to illustrate the ERB bandwidths of standard therapy tones as a function of the tinnitus frequency for a frequency-dependent hearing impairment.

This situation becomes more complex when a hearing loss that occurs more commonly in practice is considered, namely when the hearing threshold becomes worse with an increase in frequency. In such a case, the respective audiogram is no longer a horizontal line but instead has a slope. FIG. 10 illustrates one such case with a hearing threshold h, which becomes worse with an increase in frequency, namely the pitch. FIG. 10 is based on the audiogram for the patient in FIG. 2.

FIG. 10 shows the ERB edges bordering the respective ERB, divided by the tinnitus frequency $f_T$ (cf. y axis) for the four therapy tones $f_{CR1}$, $f_{CR2}$, $f_{CR3}$ and $f_{CR4}$ as well as for the tinnitus frequency $f_T$, each plotted as a function of the tinnitus frequency $f_T$ (cf. X axis). The tinnitus frequency $f_T$ perceived by the patient is 2950 Hz. FIG. 10 shows the following ERB bandwidths in the order indicated from top to bottom:

ERB for the therapy tones $f_{CR4}=1.4 f_T$ with ERB edges at $c_4 \pm 0.5$ ERB ($f_{CR4}$, h) represented by solid lines, ERB for the therapy tones $f_{CR3}=1.1 f_T$ with ERB edges at $c_3 \pm 0.5$ ERB ($f_{CR3}$, h) represented by dotted lines, ERB for the tinnitus frequency $f_T$ with ERB edges at $1 \pm 0.5$ ERB ($f_T$, h) represented by solid lines, ERB for the therapy tone $f_{CR2}=0.9 f_T$ with ERB edges at $c_2 \pm 0.5$ ERB ($f_{CR2}$, h) represented by dash-dot lines and ERB for the therapy tone $f_{CR}1=0.766 f_T$ with ERB edges at $c_1 \pm 0.5$ ERB ($f_{CR1}$, h) represented by solid lines.

FIG. 10 shows that the gap between the ERBs of the therapy tones $f_{CR3}$ and $f_{CR4}$ depends greatly on the tinnitus frequency $f_T$, with a maximum occurring both in the lower frequency range and also in the higher frequency range. For a tinnitus frequency $f_T$ in the range of 416 Hz to 1.6 kHz, there is no overlap between the ERBs of the therapy tones $f_{CR2}$ and $f_{CR3}$. As a result, FIG. 10 shows that for a realistic auditory profile, not only are the intervals between the ERBs of the standard therapy tones unbalanced with respect to one another and with respect to the tinnitus frequency $f_T$, but also the mutual spacings of the ERBs depend to a significant extent on the tinnitus frequency $f_T$. Since the tinnitus frequency $f_T$ typically changes as a result of treatment, in most case the tinnitus frequency $f_T$ drops when the arrangement of ERBs during treatment will also change. Consequently, the efficacy of the treatment also does not remain constant over the course of the treatment.

The overlap of the ERBs is determined in order to be able to evaluate the arrangement of ERBs of the therapy tones and the tinnitus tone. To do so, two frequencies $f_j$ and $f_k$ shall be considered, wherein $f_j \leq f_k$; $h_j$ and $h_k$ are the respective hearing thresholds in dB HL at the frequencies $f_j$ and/or $f_k$; $h_j$ and $h_k$ are determined either directly with the help of an audiologic hearing threshold measurement or by way of a linear interpolation of the hearing thresholds, for example, around the frequencies $f_j$ and/or $f_k$. The relative overlap between the ERB bandwidth ERB($f_j$, $h_j$) and the frequency $f_j$ and the ERB bandwidth ERB($f_k$, $h_k$) of the frequency $f_k$ based on the smaller ERB bandwidth can be calculated as follows:

$$\varphi(f_j, f_k) = \frac{\gamma(f_j, f_k)}{\min\{ERB(f_j, h_j), ERB(f_k, h_k)\}} \quad (11)$$

where $$\gamma(f_j, f_k) = \begin{cases} b_j - a_k & \text{for } f_j \leq f_k \\ b_k - a_j & \text{for } f_j > f_k \end{cases}, \quad (12)$$

where $a_j$ and $b_j$ are the lower and/or upper, respectively, edges of the ERB of the frequency $f_j$, and ERB($f_j$, $h_j$)=$b_j - a_j$. Furthermore, $a_k$ and $b_k$ are the lower and/or upper edges, respectively, of the ERB of the frequency $f_k$, ERB($f_k$, $h_k$), and $\min\{x, y\}$ is the minimum of x and y.

Alternatively, a predefined reference value may be used in the denominator of equation (11) for normalization instead of the smaller ERB. In this case, the equation for the relative overlap is as follows:

$$\rho(f_j, f_k) = \frac{\gamma(f_j, f_k)}{ERB(f_k, h_k)} \quad (13)$$

where $$\gamma(f_j, f_k) = \begin{cases} b_j - a_k & \text{for } f_j \leq f_k \\ b_k - a_j & \text{for } f_j > f_k \end{cases}. \quad (14)$$

The relative overlap $\varphi(f_j, f_k)$ and/or $\rho(f_j, f_k)$ may thus assume both positive values and negative values (as well as the value zero). In the case of positive values, this is a true overlap, whereas negative values for the relative overlap $\varphi(f, f_k)$ and/or $\rho(f_j, f_k)$ indicate a gap (and/or a hole and/or a space) between the two ERBs.

The relative overlap between the ERB bandwidth of each of the therapy tone and the ERB bandwidth of the tinnitus frequency $f_T$ can be determined in this way. FIG. 11 shows the relative overlap $\rho(f_j, f_k)$ between an ERB of the frequency f and the ERB of the tinnitus frequency $f_T$ plotted as a function of the frequency f. For the tinnitus ERB, it holds that ERB($f_T$, $h_T$), where $f_T$ is the dominant tinnitus frequency, which can be determined by way of "pitch matching," for example, and $h_T$ is the hearing threshold in units of dB HL at the tinnitus frequency $f_T$. The hearing threshold is either determined directly with the help of an audiologic hearing threshold measurement or by way of a linear interpolation of the hearing thresholds around the frequency $f_T$, for example. The data on the patient from FIG. 2 was used for the hearing threshold, wherein the tinnitus frequency is at 2950 Hz. The maximum relative overlap $\rho(f, f_T)$ is reached when f=$f_T$. In this case, it holds that $\rho(f_T, f_T)=1$.

The possibility of calculating the upper and lower edges of the ERBs shown as examples in FIGS. 7 to 9 is described below:
where a and b are the lower and upper edges, respectively, of ERB(f, h), and $a_T$ and $b_T$ are the lower and upper edges, respectively, of ERB($f_T$, $h_T$).
$u_{CRj}$=upper edge of the ERB of the therapy tone #j (where j=1, 2, 3, 4):

$$u_{CRj}(f_T) = f_{CRj} + \frac{1}{2}ERB(f_{CRj}, h_{CRj})$$
$$= c_j f_T + \frac{1}{2}ERB_N(f_{CRj}) \cdot c(h_{CRj})$$
$$= c_j f_T + \frac{1}{2}(\eta c_j f_T + 24.7) \cdot c(h_{CRj})$$
$$= c_j\left[1 + \frac{\eta}{2}c(h_{CRj})\right]f_T + 12.35 \cdot c(h_{CRj})$$

This yields the following with respect to the tinnitus frequency $f_T$:

$$\frac{u_{CRj}(f_T)}{f_T} = c_j\left[1 + \frac{\eta}{2}c(h_{CRj})\right] + 12.35\frac{c(h_{CRj})}{f_T}$$

In the case for a high tinnitus frequency $f_T$, this yields:

$$\frac{u_{CRj}(f_T)}{f_T} \to c_j\left[1 + \frac{\eta}{2}c(h_{CRj})\right]$$

for $f_T \to \infty$.
$l_{CRj}$=lower edge of the ERB of the therapy tone #j (where j=1, 2, 3, 4):

$$l_{CRj}(f_T) = f_{CRj} - \frac{1}{2}ERB(f_{CRj}, h_{CRj})$$
$$= c_j f_T - \frac{1}{2}ERB_N(f_{CRj}) \cdot c(h_{CRj})$$
$$= c_j f_T - \frac{1}{2}(\eta c_j f_T + 24.7) \cdot c(h_{CRj})$$
$$= c_j\left[1 - \frac{\eta}{2}c(h_{CRj})\right]f_T - 12.35 \cdot c(h_{CRj})$$

With respect to the tinnitus frequency $f_T$, this yields:

$$\frac{l_{CRj}(f_T)}{f_T} = c_j\left[1 - \frac{\eta}{2}c(h_{CRj})\right] - 12.35\frac{c(h_{CRj})}{f_T}$$

In the case for a large tinnitus frequency $f_T$, this yields:

$$\frac{l_{CRj}(f_T)}{f_T} \to c_j\left[1 - \frac{\eta}{2}c(h_{CRj})\right]$$

for $f_T \to \infty$.

$$\frac{u_{CRj}(f_T)}{f_T} \text{ and } \frac{l_{CRj}(f_T)}{f_T}$$

are the upper and lower edges in FIGS. 7 through 9.

To determine the upper and lower edges for the tinnitus ERB, $c_j$ is replaced by 1, which yields:

$$\frac{u_T(f_T)}{f_T} = 1 + \frac{\eta}{2}c(h_T) + 12.35\frac{c(h_T)}{f_T}$$

where $$\frac{u_T(f_T)}{f_T} \to 1 + \frac{\eta}{2}c(h_T)$$

for $f_T \to \infty$ and $$\frac{l_T(f_T)}{f_T} = 1 - \frac{\eta}{2}c(h_T) - 12.35\frac{c(h_T)}{f_T}$$

where $$\frac{l_T(f_T)}{f_T} \to 1 - \frac{\eta}{2}c(h_T)$$

for $f_T \to \infty$.

One option for calculating the relative ERB overlaps shown in FIG. 11 as an example is described below.

First, a more explicit formula is derived for $\gamma(f, f_T)$. The formula for the relative ERB overlap is calculated as follows:

$$\rho(f, f_T) = \frac{\gamma(f, f_T)}{\min\{ERB(f_T, h_T), ERB(f, h)\}}$$

with $$\gamma(f, f_T) = \begin{cases} b - a_T & f \le f_T \\ b_T - a, & f > f_T \end{cases}$$

where $$ERB(f, h) = ERB_N(f) \cdot c(h)$$
$$c(h) = \begin{cases} 1 + \dfrac{h}{50 \text{ dB } HL}, & 0 \le h \le 50 \text{ dB } HL \\ 2, & h > 50 \text{ dB } HL \end{cases}$$
$$ERB_N(f) = \eta f + 24.7,$$
$$\eta = 107,939/1000$$

where a and b are the lower and upper edges, respectively, of ERB(f, h), and $a_T$ and $b_T$ are the lower and upper edges, respectively, of ERB($f_T$, $h_T$). Using the equations given above, this yields:

$$a = \left(1 - \frac{\eta c(h)}{2}\right)f - 12.35 c(h)$$

-continued $$b = \left(1 + \frac{\eta c(h)}{2}\right)f + 12.35\, c(h)$$

$$a_T = \left(1 - \frac{\eta c(h_T)}{2}\right)f_T - 12.35\, c(h_T)$$

$$b_T = \left(1 + \frac{\eta c(h_T)}{2}\right)f_T + 12.35\, c(h_T)$$

and $$b - a_T = \left(1 + \frac{\eta c(h)}{2}\right)f - \left(1 - \frac{\eta c(h_T)}{2}\right)f_T + 12.35\, [c(h) + c(h_T)]$$

$$b_T - a = \left(1 + \frac{\eta c(h_T)}{2}\right)f_T - \left(1 - \frac{\eta c(h)}{2}\right)f + 12.35\, [c(h) + c(h_T)]$$

FIG. 12 illustrates schematically a device 10 for stimulation of a patient by using acoustic stimulation signals. The device 10 may be used for treatment of diseases characterized by neural populations with a pathological synchronous and oscillatory neural activity.

In addition to the tinnitus therapy, the device 10 can also be used for treatment of the following diseases: depression, epilepsy, compulsive disorders, dementia diseases, Alzheimer's disease, autism, dysfunctions after a stroke, sleep disorders, schizophrenia, irritable bowel syndrome, addictive diseases, borderline personality disorder, attention deficit disorder, attention deficit hyperactivity disorder, gambling addiction, neuroses, bulimia, anorexia, eating disorders, burnout syndrome, migraines, cluster headaches, general headaches as well as other diseases characterized by pathologically enhanced synchronization of neurons.

The device 10 comprises of a control unit 11 and a stimulation unit 12, which generates acoustic stimulation signals and stimulates neurons in the patient's brain (from the brain stem to the cortex) and/or the patient's spinal cord by way of a plurality of stimulation channels. Each stimulation channel permits stimulation of another target region in the patient's brain and/or spinal cord. During operation of the device 10, the control unit 11 carries out control of the stimulation unit 12. To do so, the control unit 11 generates control signals, which are received by the stimulation unit 12.

The control unit 11 and the stimulation unit 12 are noninvasive units, namely they are outside of the patient's body during operation of the device 10 and are not implanted surgically in the patient's body.

The device 10 may optionally also comprise an evaluation unit 13 for evaluating the success of a treatment and an input/output unit 14, with which the control unit 11 and/or the evaluation unit 13 can make information and/or data available.

The individual components of the device 10, in particular the control unit 11, the stimulation unit 12, the evaluation unit 13 and/or the input/output unit 14 may be separated from one another structurally. The device 10 may therefore also be regarded as a system. To carry out its functions, the control unit 11 and/or the evaluation unit 13 may include a processor, for example, a microcontroller. The stimulation methods described here may be stored as software code in a memory associated with the control unit 11 and/or to the evaluation unit 13.

According to a first embodiment, the optimum arrangement of one or more acoustic therapy signals on the frequency axis is determined with the help of the device 10. The number of acoustic therapy signals is usually predetermined.

In the first embodiment, the control unit 11 is designed or configured so that it determines a bandwidth of an auditory filter with a frequency of a predetermined pitch as a center frequency, wherein this bandwidth represents a reference bandwidth. The control unit 11 also determines the frequency of a first acoustic therapy signal, such that a measure of overlap between the reference bandwidth around the frequency of the predetermined tone and a first bandwidth of an auditory filter with the frequency of the first acoustic therapy signal as the center frequency assumes a predetermined first value. Next, the first acoustic therapy signal is played for the patient by the simulation unit 12.

The first acoustic therapy signal as well as all additional acoustic therapy signals described in the present disclosure may be either a tone, such as a pure sinusoidal vibration, or a mixed tone, such as a sound comprised of different tones of any frequencies. The concept of a mixed tone also comprises noise and sounds. For reasons of simplicity, the term "therapy tones" is used in some embodiments but this could also be mean mixed therapy tones.

The measure of coverage may be an overlap or a gap. In some embodiments, it is referred to as an overlap for reasons of simplicity. If the overlap has a negative value, it is a gap.

The first embodiment is described below on the basis of an example embodiment (cf. FIGS. 13 to 16). In this example embodiment, a patient suffering from tinnitus is treated with the help of the device 10. The frequency of the predetermined tone in this case is the tinnitus frequency $f_T$ of the dominant tinnitus tone perceived by the patient. As the bandwidth around a center frequency, the ERB bandwidth around the tinnitus frequency $f_T$ is used here as the reference bandwidth and/or the ERB bandwidths around the frequencies of the four therapy tones as the first, second, third and/or fourth bandwidths are used. Furthermore, the relative ERB overlap is used to determine the optimum arrangement of a predetermined number of therapy tones on the frequency axis, wherein the predetermined number here is four.

The procedure for determining the individualized hearing threshold-adapted therapy tones according to the first embodiment is diagramed in the flow chart in FIG. 13. First, the dominant or most pronounced tinnitus frequency $f_T$ or the frequency perceived by the patient as the most annoying is determined by tone matching, for example. In the case of multiple dominant tinnitus frequencies, they are treated in succession. The highest priority here is typically given to the dominant tinnitus frequencies that are the highest and/or the most annoying. The therapy tones are calculated with respect to the tinnitus frequency $f_T$ or the neighboring therapy tones based on the relative ERB overlap extracted from the patient's audiogram. The broadening of the bandwidth of the auditory filters caused by hearing loss is taken into account by using the audiogram. A loudness equalization is performed to adapt the loudness of the therapy tones mutually to one another. FIG. 13 shows measurements carried out on the patient in boxes outlined with dotted lines, while the signal broadening and sound production are shown in boxes outlined with solid lines.

In the example embodiment of the first embodiment which is described below, four therapy tones are used. According to a first variant of the example embodiment, the ERB bandwidth of the tinnitus frequency $f_T$ is used as a reference for all four therapy tones, and the relative ERB overlaps for each ERB of the four therapy tones are calculated with the ERB of the tinnitus frequency $f_T$. The resulting relative ERB overlaps are referred to as $\rho(f_{CR1hta}, f_T)$, $\rho(f_{CR2hta}, f_T)$, $\rho(f_{CR3hta}, f_T)$ and $\rho(f_{CR4hta}, f_T)$ where "hta" stands for "hearing threshold adapted."

By analysis of data published in the document D27, it has been discovered that the following relative ERB overlaps produce optimum therapeutic results for the four therapy tones: $\rho(f_{CR1hta}, f_T)=-0.25$, $\rho(f_{CR2hta}, f_T)=0.47$, $\rho(f_{CR3hta}, f_T)=0.58$ and $\rho(f_{CR4hta}, f_T)=-0.65$. These values for the ERB overlap can be used as the predetermined first, second, third and/or fourth values for the measure of coverage. Patients stimulated with these ERB overlap values respond significantly more quickly to the acoustic CR neuromodulation than even those to a much greater extent in comparison with an acoustic CR neuromodulation using other ERB overlap values.

Accordingly, the ERB overlap values given above can be used to determine the therapy tones with the optimal frequencies. To do so the tinnitus frequency $f_T$ which is perceived by the patient and can be determined, for example, by way of a traditional method for determining the pitch level of the tinnitus ("pitch matching") and the interpolated hearing threshold which can be determined from the patient's audiogram are involved. With this data, the frequencies of the four therapy tones that meet the predetermined conditions can be determined according to $\rho(f_{CR1hta}, f_T)=-0.25$, $\rho(f_{CR2hta}, f_T)=0.47$, $\rho(f_{CR3hta}, f_T)=0.58$ and $\rho(f_{CR4hta}, f_T)=-0.65$.

The assignments $\rho(f_{CRjhta}, f_T)=\hat{\rho}_j$ for $j=1, \ldots, 4$ where $\hat{\rho}_1=-0.25$, $\hat{\rho}_2=0.47$, $\hat{\rho}_3=0.58$ and $\hat{\rho}_4=-0.65$ are plotted as horizontal lines in FIG. 14. Otherwise FIG. 14 is identical to FIG. 11. The points of intersection of the four horizontal lines with the graphs plotted in FIG. 14 and characterized by circles indicate the optimum frequencies of the four therapy tones.

To determine the four frequencies, the following calculations can be carried out:

(i) The calculation is begun at $f=f_T$ and the frequency $f$ is reduced until $\rho(f, f_T)=\hat{\rho}_2$ has been reached on the graph in FIG. 14. Then the respective frequency $f_{CR2hta}$ can be taken from the frequency axis in FIG. 14. Next the frequency $f$ is reduced further until the graph in FIG. 14 has reached $\rho(f, f_T)=\hat{\rho}_1$. The respective frequency is $f_{CR1hta}$.

(ii) The calculation begins again at $f=f_T$ and the frequency $f$ is increased until $\rho(f, f_T)=\hat{\rho}_3$ has been reached on the graph in FIG. 14. The respective frequency $f_{CR3hta}$ can be derived from the frequency axis in FIG. 14. Next the frequency $f$ is increased further until the graph in FIG. 14 has reached $\rho(f, f_T)=\hat{\rho}_4$. The respective frequency is $f_{CR4hta}$.

In general, the control unit 11 determines the frequencies of the first through fourth acoustic therapy signals $f_{CR1hta}$ through $f_{C42hta}$ in that the control unit 11 varies the frequency of the respective acoustic therapy signal until the control unit 11 ascertains that the extent of coverage between the reference bandwidth around the tinnitus frequency $f_T$ and the bandwidth of the auditory filter with the frequency of the respective acoustic therapy signal as the center frequency assumes the predetermined value $\hat{\rho}_1, \hat{\rho}_2, \hat{\rho}_3$ and/or $\hat{\rho}_4$.

Within the scope of some embodiments of this disclosure, the two following data records have been found for optimum relative ERB overlaps in addition to the data set given above:

$$\rho(f_{CR1hta},f_T)=0.05, \rho(f_{CR2hta},f_T)=0.55,$$
$$\rho(f_{CR3hta},f_T)=0.65 \text{ and } \rho(f_{CR4hta},f_T)=-0.45 \quad (i)$$

$$\rho(f_{CR1hta},f_T)=0.15, \rho(f_{CR2hta},f_T)=0.65, \rho(f_{CR3hta},f_T)=0.7$$
$$\text{and } \rho(f_{CR4hta},f_T)=-0.35 \quad (ii)$$

It should be pointed out that the four data sets cited here are just three examples of the relative ERB overlaps with which optimum therapeutic success can be achieved. For example, the acoustic stimulation therapy may also be used successfully when the values for the relative ERB overlaps are varied within the ranges of ±10% or up to ±20%. Also, although certain values for optimum relative ERB overlaps are provided, these values are provided by way of example, and other embodiments can be implemented with different values relative to the example values.

It has been found that the tinnitus ERB should be used as a reference for normalization and $\rho(f_{CRjhta}, f_T)$ should be calculated for $j=1, \ldots, 4$ instead of $\varphi(f_{CRjhta}, f_T)$. In contrast with $\rho(f_{CRjhta}, f_T)$, $\varphi(f_{CRjhta}, f_T)$ typically leads to suboptimum results or even to no improvement at all for the patient.

FIG. 15 shows the respective ERB edges divided by the tinnitus frequency $f_T$ (cf. y axis) for the optimum relative ERB overlaps $\rho(f_{CR1hta}, f_T)=-0.25$, $\rho(f_{CR2hta}, f_T)=0.47$, $\rho(f_{CR3hta}, f_T)=0.58$ and $\rho(f_{CR4hta}, f_T)=-0.65$ as well as the hearing threshold h of the tinnitus patient from FIG. 2 and a tinnitus frequency $f_T$ of 2950 Hz plotted as a function of the tinnitus frequency $f_T$ (cf. X axis). In FIG. 15, the following ERB bandwidths are represented in the order given, from top to bottom:

ERB for the therapy tones $f_{CR4hta}$ with ERB edges at $f_{CF4hta}/f_T \pm 0.5$ ERB ($f_{CR4hta}$, h) represented by solid lines, ERB for the therapy tones $f_{CR3hta}$ with ERB edges at $f_{CR3hta}/f_T \pm 0.5$ ERB ($f_{CR3hta}$, h) represented by dotted lines, ERB for the tinnitus frequency $f_T$ with ERB edges at $1 \pm 0.5$ ERB ($f_T$, h) represented by solid lines, ERB for the therapy tone $f_{CR2hta}$ with ERB edges at $f_{CR2hta}/f_T \pm 0.5$ ERB ($f_{CR2hta}$, h) represented by dash-dot lines and ERB for the therapy tone $f_{CR1hta}$ with ERB edges at $f_{CR1hta}/f_T \pm 0.5$ ERB ($f_{CR1hta}$, h) represented by solid lines.

FIG. 15 shows that the overlaps and/or gaps between the ERBs of the therapy tones and the overlaps and/or gaps between tinnitus ERB and the ERBs of the therapy tones are stable over the entire tinnitus frequency axis. For example, the overlaps and/or gaps can vary up to ±10% or up to ±20% within the tinnitus frequency axis.

FIG. 16 shows the personalized hearing threshold-adapted frequencies of the four therapy tones divided by the tinnitus frequency $f_T$. The personalized frequencies can also be referred to as individualized frequencies. FIG. 16 shows from bottom to top $f_{CR1hta}/f_T$, $f_{CR2hta}/f_T$, $f_{CR3hta}/f_T$ and $f_{CR4hta}/f_T$ in the order given, represented by solid lines. FIG. 16 uses the hearing threshold h of the patient from FIG. 2 and the tinnitus frequency $f_T$ of 2950 Hz plus the optimum relative ERB overlaps $\rho(f_{CR1hta}, f_T)=-0.25$, $\rho(f_{CR2hta}, f_T)=0.47$, $\rho(f_{CR3hta}, f_T)=0.58$ and $\rho(f_{CR4hta}, f_T)=-0.65$. For comparison, FIG. 16 also shows the ratios between the frequencies of the standard therapy tones and the tinnitus frequency $f_T$, i.e., $f_{CR1}/f_T=0.766$, $f_{CR2}/f_T=0.9$, $f_{CR3}/f_T=1.1$ and $f_{CR4}/f_T=1.4$, from bottom to top in the order given represented by dotted horizontal lines.

FIG. 16 shows the relationship between the frequencies $f_{CR1}$, $f_{CR2}$, $f_{CR3}$ and $f_{CR4}$ of the fixed standard therapy tones and the frequencies $f_{CR1hta}$, $f_{CR2hta}$, $f_{CR3hta}$ and $f_{CR4hta}$ of the personalized hearing threshold-adapted therapy tones. The intervals of the personalized hearing threshold-adapted therapy tones $f_{CR1hta}$, $f_{CR2hta}$, $f_{CR3hta}$ and $f_{CR4hta}$ vary along the tinnitus frequency axis and may be wider or narrower depending on the patient's hearing threshold in comparison with the intervals of the standard therapy tones $f_{CR1}$, $f_{CR2}$, $f_{CR3}$ and $f_{CR4}$.

According to a second variant of the example embodiment, the ERB bandwidth of the tinnitus frequency $f_T$ is used solely as a reference for the therapy tone situated directly in proximity to the ERB of the tinnitus frequency $f_T$, namely the two middle therapy tones in the case of four therapy tones, for example. For therapy tones located farther toward the outside of the frequency axis, the relative ERB overlap with the next closest therapy tone on the frequency axis is used.

An analysis of the data published in document D27 has revealed the following optimum relative ERB overlaps for the four therapy tones: $\rho(f_{CR1hta}, f_{CR2hta})=0.17$, $\rho(f_{CR2hta}, f_T)=0.47$, $\rho(f_{CR3hta}, f_T)=0.58$ and $\rho(f_{CR3hta}, f_{CR4hta})=-0.13$. Patients stimulated with these relative ERB overlap values responded significantly more quickly to the acoustic CR neuromodulation as well as to a much greater extent in comparison with an acoustic CR neuromodulation using other ERB overlap values. This first variant and the second variant of the example embodiment yield essentially the same improvement in the acoustic CR therapy.

It has been found that the ERB closest to the tinnitus frequency $f_T$ should be used as a reference for the normalization and in addition the terms $\rho(f_{CR1hta}, f_{CR2hta})$, $\rho(f_{CR2hta}, f_T)$, $\rho(f_{CR3hta}, f_T)$ and $\rho(f_{CR3hta}, f_{CR4hta})$ should be determined instead of the terms $\varphi(f_{CR1hta}, f_{CR2hta})$, $\varphi(f_{CR2hta}, f_T)$, $\varphi(f_{CR3hta}, f_T)$ and $\varphi(f_{CR3hta}, f_{CR4hta})$ to avoid suboptimum results.

In a second embodiment, with the help of the device 10, the optimum number of several acoustic therapy signals and their best possible arrangement on the frequency axis are determined (cf. FIGS. 17 through 22). In the second embodiment, not only the optimum intervals between the acoustic therapy signals are calibrated but also the location of the entire group of acoustic therapy signals on the frequency axis is calibrated. Since the second embodiment may involve a lower precision in determination of the tinnitus frequency $f_T$ perceived by the patient, the second embodiment may be used advantageously in the treatment of patients who have difficulties in audiological determination of the tinnitus frequency $f_T$.

The control unit 11 is designed or configured in the second embodiment such that it determines the frequency of a first acoustic therapy signal and the frequency of a second acoustic therapy signal such that a measure of coverage between a first bandwidth of an auditory filter with the frequency of the first acoustic therapy signal as the center frequency and a second bandwidth of an auditory filter with the frequency of the second acoustic therapy signal as the center frequency assumes a predetermined first value. Next the first acoustic therapy signal and the second acoustic therapy signal are played for the patient by the stimulation unit 12.

In the second embodiment, the first and second acoustic therapy signals as well as all other acoustic therapy signals may each be either a tone, such as a pure sinusoidal vibration, or a mixed tone, such as a sound comprised of tones of any frequency, in particular a noise or a sound. For reasons of simplicity, the term therapy tones is used in some embodiments, but this may also be understood to refer to mixed therapy tones.

The measure of overlap may be either an overlap or a gap. For reasons of simplicity, the term "overlap" is used in some embodiments. If the overlap has a negative value, it is a gap.

The second embodiment is described below on the basis of one example embodiment (cf. FIGS. 17 through 22). In the example embodiment a patient suffering from tinnitus is treated with the help of the device 10. As bandwidths around center frequencies, the ERB bandwidths around the frequencies of the therapy tones are used as the first, second, third and/or fourth bandwidths. Furthermore, the relative ERB overlap is used to determine the optimum number of therapy tones and their optimum arrangement on the frequency axis.

The procedure for determining the optimum number of therapy tones and their optimum arrangement on the frequency axis according to a first variant of the example embodiment is diagrammed in the flow chart in FIG. 17. The frequency axis in FIG. 17 shows the tonotopic organization of the primary auditory cortex. A neural population 1 in the primary auditory cortex, which has a pathological synchronous and oscillatory neural activity, is to be desynchronized by way of a targeted acoustic stimulation, in particular an acoustic CR stimulation.

This stimulation is started with a first therapy tone and a second therapy tone in the vicinity of the frequency $f_T$ of the dominant tinnitus tone perceived by the patient.

The determination of the tinnitus frequency $f_T$ should be at least accurate enough so that the subpopulations 2 and 3, activated by the first and second therapy tones, are linked either within or in close proximity, for example, by connections over one or more synapses, for example, in the neural population 1 with the pathological synchronous and oscillatory neural activity, or they are linked by nerve pathways directly to neural population 1.

Stimulation with just two therapy tones may not be adequate under some circumstances to achieve a complete desynchronization of neural population 1 and a complete disappearance of the tinnitus symptoms but typically initial therapeutic success can be achieved through such stimulation in the sense that the pathological synchronous and oscillatory neural activity and the tinnitus symptoms are both reduced. In the second embodiment, successive additional therapy tones are added to the first and second therapy tones, a check being performed by the evaluation unit 13 each time a therapy tone is added to ascertain whether the result of the treatment has been improved by the added therapy tone. The additional therapy tones may be added to the first and second therapy tones on both sides (with respect to the frequency axis).

In the example embodiment shown in FIG. 17, a third therapy tone which stimulates subpopulation 4 is added to the first and second therapy tones. The frequency of the third therapy tone is lower here than the frequencies of the first and second therapy tones. The patient is then stimulated with a CR stimulation formed from the three therapy tones (cf. the description of FIG. 23 below where N=3, namely stimulated over three stimulation channels). It is then found by way of the evaluation unit 13 that by adding the third therapy tone the desynchronization of the neural population 1 is further increased and the tinnitus symptoms are further reduced. Accordingly, the third therapy tone is retained and not discarded. Furthermore it can be concluded from this that the subpopulation 4 stimulated by the third therapy tone is situated within or sufficiently close to the target neural population 1 or is at least connected directly to the target neural population 1 by way of nerve pathways.

Next a fourth therapy tone which stimulates a subpopulation 5 and a fifth therapy tone which stimulates a subpopulation 6 are also added to the first three therapy tones. In CR stimulation with the corresponding sets of therapy tones (cf. the description of FIG. 23 below, where N=4, namely stimulation is performed over four stimulation channels), however, it is found that the stimulation success is not further improved in either case. Consequently, the two subpopulations 5 and 6 have just a slight overlap with the neural population 1. Therefore, the fourth and fifth therapy tones are discarded by the control unit 11.

As a result the first, second and third therapy tones are selected for stimulation of the patient, and a suitable CR stimulation is performed with these therapy tones.

It should be noted that the frequencies of the therapy tones mentioned above are selected so that their ERB bandwidths have a predefined overlap with the ERB bandwidth of the respective neighboring therapy tone. To emphasize this relationship, subpopulations adjacent in FIG. 17 come in contact with one another, namely the subpopulations related to the ERBs have the same spatial distance from the respective neighboring subpopulations. However, the spatial distance illustrated in FIG. 17 serves for illustrative purposes.

A matching method for determining the pitch of the tinnitus ("pitch matching") yields the dominant or most pronounced tinnitus frequency $f_T$ or the frequency perceived by the patient as the most annoying. A pair of first and second therapy tones with the frequencies $f_{CR2hta}$ and $f_{CR3hta}$ which stimulate subpopulations 2 and 3 are then calculated with respect to the tinnitus frequency $f_T$ or with respect to neighboring therapy tones based on a predefined value for the relative ERB overlap, which has been extracted from the patient's audiogram, thereby taking into account the hearing threshold-induced spreading of the auditory filters.

The loudness levels of the first and second therapy tones are adapted to one another by way of a loudness matching. Furthermore, the success of the therapy is evaluated (e.g., by way of a clinical assessment "clinical scores"), in particular "visual analog scale scores" for loudness and/or annoyance (cf. document D1) or a tinnitus questionnaire (cf. document D2) and/or objectively such as an electrophysiological measurement, in particular an electroencephalographic (EEG) or electromyographic (EMG) or magnetoencephalographic (MEG) measurement.

For example, the neural activity of the neuron population 1 can be measured by way of noninvasive sensors, e.g., EEG, EMG or MEG sensors that are utilized chronically or intermittently. The neural activity can also be determined by detection of characteristic motion patterns such as tremor, akinesis or epileptic seizures with the help of an accelerometer or gyroscope or indirectly by measuring the activation of the autonomous nervous system or by measuring the conductivity resistance of the skin.

Alternatively, the sensor may also be implanted in the patient's body. Examples of invasive sensors that may be used include epicortical electrodes, deep brain electrodes for measuring local field potentials, for example, subdural or epidural brain electrodes, subcutaneous EEG electrodes and subdural or epidural spinal cord electrodes.

The evaluation unit 13 may contain such sensors or it may receive information and/or data sent to the evaluation unit 13 via the input/output unit 14, where this information is used by the evaluation unit 13 to ascertain the success of the stimulation. For example, the evaluation unit 13 may detect a successful stimulation if the synchronicity of the neural population 1 has been reduced by at least a predefined value as a result of the stimulation.

As illustrated schematically in FIG. 17, additional therapy tones are added to the therapy tones already selected. If the therapeutic success is thereby increased by a certain value, for example, the synchronicity of the neural population 1 is reduced by at least a predefined value, then the therapy tones are retained and otherwise they are discarded.

The addition of another therapy tone is assessed as a success, for example, if the clinical assessments or the objective electrophysiological measurement show an improvement by at least 5% or 10% or 15%, etc., for example.

To obtain reliable results, the assessment of the therapeutic success can be repeated several times.

In the present embodiment a predetermined value is used for the relative ERB overlap for all neighboring therapy tones. For example, one value may be selected from the values 0.35, 0.47, 0.58, 0.65 and 0.71 for the predetermined value for the ERB overlap $\rho(f_{CRjhta}, f_{CRj+1hta})$ of neighboring therapy tones. However, therapeutic success can be achieved if these values are varied within ranges of ±10% or even ±25%. The frequencies of neighboring therapy tones are determined, for example, by having the control unit 11 vary the frequency of the neighboring therapy tones until the control unit 11 detects that the ERB overlap $\rho(f_{CRjhta}, f_{CRj+1hta})$ of the neighboring therapy tones has assumed the selected value for the ERB overlap. It is advantageous if, in choosing the first two therapy tones, which stimulate subpopulations 2 and 3 in FIG. 17, not only is their mutual relative ERB overlap determined, but in addition the criterion is that the relative ERB overlap of the two tones, respectively, is identical or as similar as possible to the tinnitus ERB (in relation to the tinnitus ERB). This boundary condition "anchors" the first pair of therapy tones in a balanced manner, e.g., on the tinnitus frequency $f_T$, based on the extent of the tinnitus ERB.

The procedure for determining the individualized hearing threshold-adapted therapy tones with the calibration of both the number and frequency intervals of the therapy tones according to the first variant of the second embodiment is diagramed in the flow chart in FIG. 18. First the dominant or most pronounced tinnitus frequency $f_T$ or the frequency perceived by the patient as being the most annoying is determined by pitch matching, for example. A first and a second therapy tones are then calculated with respect to the tinnitus frequency $f_T$ or neighboring therapy tones are calculated based on a predetermined value for the relative ERB overlap, wherein the ERB overlap is extracted from the patient's audiogram and the hearing threshold adapted spreading of the auditory filters is thereby taken into account. The therapeutic success is evaluated by way of CR stimulation (using two stimulation channels) and additional therapy tones on the right and left sides of the frequency axis are added. If the therapeutic success is not further improved by adding a therapy tone on the right or left side of the frequency axis, then no further therapy tone is added on the respective side. In FIG. 18, measurements and evaluations performed on the patient are shown in boxes outlined with dotted lines whereas data analysis, signal processing and sound generation are shown in boxes outlined with solid lines.

FIG. 19 shows the procedure for determining the optimum number of therapy tones and their optimum arrangement on the frequency axis according to a second variant of the example embodiment of the second embodiment. In the second variant, in comparison with the first variant of the example embodiment, the relative ERB overlap $\rho(f_{CRjhta}, f_{CRj+1hta})$ of neighboring therapy tones can be calibrated. In a first step the relative ERB overlap $\rho(f_{CR2ta}, f_{CR3hta})$ of the first and second therapy tones by way of which the subpopulations 2 and 3 are stimulated is calibrated. To do so multiple CR stimulations are performed using the two therapy tones and different values for the relative ERB overlap $\rho(f_{CR2ta}, f_{CR3hta})$. The value for the relative ERB overlap $\rho(f_{CR2ta}, f_{CR3hta})$ can be selected from the following values, for example: 0.35, 0.47, 0.58, 0.65 and 0.71. Next the value for the relative ERB overlap at which the CR stimulation has shown the greatest therapeutic success is selected. Alternatively the relative ERB overlap $\rho(f_{CR2ta}, f_{CR3hta})$ can also be varied continuously and/or incrementally, and the value range at which the best therapeutic results are obtained can be selected. In another alternative, the relative ERB overlap can be varied until an adequate reduction, e.g., 10% or 7% or 5% of the synchronous EEG performance/power is observed. It is advantageous if, in the selection of the first two therapy tones which stimulate subpopulations 2 and 3 in FIG. 19, not only their mutual relative ERB overlap is taken into account but also in addition the criterion that the relative ERB overlap of the two therapy tones with the tinnitus ERB (in relation to the tinnitus ERB) should be identical or at least as similar as possible. This boundary condition "anchors" the first pair of therapy tones in a balanced manner, namely it is based on the extent of the tinnitus ERB relative to the tinnitus frequency $f_T$. This individual value which is determined with the help of the first and second therapy tones for the relative ERB overlap is then used for all other therapy tones. The procedure is otherwise exactly the same as that represented in FIG. 17.

The procedure for determining the individualized hearing threshold adapted therapy tones with the calibration of the number of therapy tones, the frequency intervals of the therapy tones and the relative ERB overlap of neighboring therapy tones according to the second variant of the second embodiment are diagramed in the flow chart in FIG. 20. First the dominant or most pronounced tinnitus frequency $f_T$ or that perceived by the patient as the most annoying is ascertained, e.g., by pitch matching. A first therapy tone and a second therapy tone are then calculated with respect to the tinnitus frequency $f_T$ or neighboring therapy tones based on a predetermined value for the relative ERB overlap, wherein the ERB overlap is extracted from the patient's audiogram and the hearing threshold adapted broadening of the auditory filters is thereby taken into account. A loudness matching is carried out to adapt the loudness of the two therapy tones to one another, and a therapeutic success is evaluated by means of CR stimulation using the two therapy tones. Next the relative ERB overlap of the two therapy tones is calibrated. The resulting value determined for the optimum relative ERB overlap is then used for adding all other therapy tones. Additional therapy tones are added on the right or left sides of the frequency axis and the respective stimulation result achieved is assessed with the help of CR stimulation. If the therapeutic success is not improved further by adding a therapy tone on the right or left side of the frequency axis, then no further therapy tone is added on the respective side. In FIG. 20, measurements carried out on the patient and evaluations are shown in boxes outlined with dotted lines, while data analysis, signal processing and sound generation are shown in boxes outlined with solid lines.

In principle the optimum ERB overlap can be recalibrated for each additional therapy tone. However, this is time-consuming and goes beyond typical time constraints in a clinical/audiological application.

The ERB arrangement shown in FIG. 15 leads to improved treatment results, but the arrangement of the various therapy tones may still be unbalanced. For example, there is no overlap between the ERB of the therapy tone $f_{CR4hta}$ and the ERB of the therapy tone $f_{CR3hta}$ whereas the ERB of the therapy tone $f_{CR2hta}$ and the ERB of the therapy tone $f_{CR1hta}$ do overlap. It has surprisingly been discovered that a balanced tinnitus ERB-centered arrangement of the therapy tones is more advantageous for the therapeutic result and also with respect to the parameterization and therefore the calibration because just two parameters, the stretching factor of the tinnitus ERB and the number of therapy tones, are specified to be introduced into the target ERB. The stretched tinnitus ERB is referred to as the target ERB. To obtain a personalized tinnitus ERB-centered, hearing threshold adapted and balanced arrangement of therapy tones, one should proceed as shown in FIG. 13 and then continue as follows, for example.

First, the target ERB is specified by broadening the tinnitus ERB by way of a stretching factor. The stretching factor prevents narrow intervals between the therapy tones in a manner that is not advantageous. The following values for the stretching factor are advantageous in the case of four therapy tones, for example: 1.5, 2.0, 2.25 and 2.5. However, good results can still be obtained if the stretching factor is varied in a range of up to ±15%. The goal here is to place the four therapy tones in the target ERB in such a way that the arrangement is balanced. The frequencies of the four therapy tones to be determined are referred to below as $f_{CR1hb}$, $f_{CR2hb}$, $f_{CR3hb}$ and $f_{CR4hb}$ where "hb" stands for "hearing threshold adapted" or "hearing threshold adapted, balanced."

Two therapy tones with the frequencies $f_{CR2hb}$ and $f_{CR3hb}$, which meet the following conditions, are selected:
(i) The overlap of the ERBs of the two internal therapy tones with the frequencies $f_{CR2hb}$ and $f_{CR3hb}$ is not negligible and symmetrical (symmetry condition).
(ii) The mutual ERB overlap of the two therapy tones with the frequencies $f_{CR2hb}$ and $f_{CR3hb}$ (with respect to the lower ERB) is:
   identical to the overlap of the ERB of the therapy tone with the frequency $f_{CR1hb}$ and the ERB of the therapy tone with the frequency $f_{CR2hb}$ (with respect to the internal ERB, namely the ERB of the therapy tone with the frequency $f_{CR2hb}$) and
   identical to the overlap of the ERB of the therapy tone with the frequency $f_{CR3hb}$ and the ERB of the therapy tone with the frequency $f_{CR4hb}$ (with respect to the internal ERB, namely the ERB of the therapy tone with the frequency $f_{CR3hb}$).

An infinite number of balanced arrangements of therapy tones satisfy the conditions (i) and (ii). The arrangement of the therapy tones is selected with the help of the following secondary conditions: the maximum relative overlap parameters that meet the following conditions are selected:
  The frequency of the lowest therapy tone, namely the frequency $f_{CR1hb}$, is higher than the lower edge of the tinnitus ERB.
  The frequency of the highest therapy tone, namely the frequency $f_{CR4hb}$, is lower than the upper edge of the tinnitus ERB.

In FIG. 21 the ERB edges bordering the respective ERB, divided by the tinnitus frequency $f_T$ (cf. y axis) for the personalized tinnitus ERB-centered, hearing threshold-adapted and balanced arrangement of the therapy tones are plotted as a function of the tinnitus frequency $f_T$ (cf. X axis) with a stretch factor of 1.5. The hearing threshold h of the tinnitus patients from FIG. 2 and a tinnitus frequency $f_T$ of 2950 Hz were used. FIG. 21 shows the following ERB bandwidths in the order given from top to bottom:
  ERB for the therapy tones $f_{CR4hb}$ with ERB edges at $f_{CF4hb}/f_T$±0.5 ERB ($f_{CR4hb}$, h) represented by solid lines,
  ERB for the therapy tones $f_{CR3hb}$ with ERB edges at $f_{CR3hb}/f_T$±0.5 ERB ($f_{CR3hb}$, h) represented by dotted lines, ERB for the tinnitus frequency $f_T$ with ERB edges at $1\pm0.5$ ERB ($f_T$, h) represented by solid lines, ERB for the therapy tone $f_{CR2hb}$ with ERB edges at $f_{CR2hb}/f_T\pm0.5$ ERB ($f_{CR2hb}$, h) represented by dash-dot lines and ERB for the therapy tone $f_{CR1hb}$ with ERB edges at $f_{CR1hb}/f_T\pm0.5$ ERB ($f_{CR1hb}$, h) represented by solid lines.

FIG. 22 shows the personalized tinnitus ERB-centered hearing threshold-adapted and balanced frequency of the therapy tones divided by the tinnitus frequency $f_T$. The hearing threshold h of the tinnitus patients from FIG. 2, a tinnitus frequency $f_T$ of 2950 Hz and a stretch factor of 1.5 were used. FIG. 22 shows from bottom to top $f_{CR1hb}/f_T$ ('d'), $f_{CR2hb}/f_T$ ('c'), $f_{CR3hb}/f_T$ ('b') and $f_{CR4hb}/f_T$ ('a') in the order given, represented by solid lines. The lower edge ('e') and the upper edge ('a') of the target ERB divided by the tinnitus frequency $f_T$ comprise the four frequencies of the therapy tones. It should be pointed out that $f_{CR4hb}/f_T$ and the upper edge of the target ERB divided by the tinnitus frequency $f_T$ coincide ('a'). For comparison purposes, FIG. 22 also shows the ratios between the frequencies of the standard therapy tones and the tinnitus frequency $f_T$, namely $f_{CR1}/f_T=0.766$, $f_{CR2}/f_T=0.9$, $f_{CR3}/f_T=1.1$ and $f_{CR4}/f_T=1.4$, shown from bottom to top in the order given, represented by dotted horizontal lines. The frequencies $f_{CR1hb}$, $f_{CR2hb}$, $f_{CR3hb}$ and $f_{CR4hb}$ are within the target ERB, namely within the tinnitus ERB after being improved by a stretch factor of 1.5.

In principle, the larger ERB and/or the external ERB relative to the tinnitus frequency $f_T$ may be used as a reference. Instead of a symmetrical arrangement with an even number of, for example, four therapy tones, an odd number of therapy tones may also be used, such that one therapy tone, usually the center therapy tone, is aimed directly at the tinnitus frequency $f_T$.

Some embodiments permit rapid and effective calibration of the therapy tones. For example, four therapy tones can be inserted into a target ERB with a stretch factor of 1.5, for example, as described above. The ERBs of neighboring therapy tones have an identical relative overlap. Then additional therapy tones are added on the right and left sides with the same relative ERB overlap as that shown in FIGS. 17 and 18. The added therapy tones are discarded if the therapeutic result is not improved by a minimum amount, for example, an additional 5% or 10% or 15% or 25%.

In addition to treating tinnitus, the device 10 is also suitable for treating other diseases characterized by pathologically-enhanced neural synchronization. These diseases include depression, epilepsy, compulsive disorders, dementia illnesses, Alzheimer's disease, autism, dysfunctions following a stroke, sleep disorders, schizophrenia, irritable bowel syndrome, addictive diseases, borderline personality disorder, attention deficit disorder, attention deficit hyperactivity syndrome, gambling addiction, neuroses, bulimia, anorexia, eating disorders, burnout syndrome, migraines, cluster headaches and general headaches.

For treatment of the above diseases, the procedure is as follows:

(i) A frequency range with a hearing loss of ≤50 dB HL or a voice range of 250 to 6000 Hz, for example, or a range over the voice range with a hearing loss of ≤50 dB HL or a frequency range preferred by the patient (not perceived as annoying and/or troublesome, not interfering with the understanding of speech, not causing hyperacusis, etc.).

(ii) A frequency is selected either randomly or by a physician or audiologist; this frequency is specified as the frequency of the predetermined tone, namely as the tinnitus frequency $f_T$.

(iii) The steps illustrated in FIGS. 13, 18 and 20 are carried out with the selected frequency as the tinnitus frequency $f_T$.

The therapy tones obtained by way of some embodiments are used in CR stimulation. FIG. 23 shows as an example of a CR stimulation, in which sequences of therapy tones 31 to 34 are generated in four stimulation channels 21 to 24. In each of the stimulation channels 21 to 24, therapy tones 31 to 34 are generated at a certain frequency, namely each one of the therapy channels 21 to 24 stimulates a certain sub-population in the target region in the patient's brain. For example, in a therapy channel 21, therapy tones 31 with the frequency $f_{CR1hta}$ or $f_{CR1hb}$ are generated, therapy channel 22 of the therapy tone 32 with the frequency $f_{CR2hta}$ or $f_{CR2hb}$, therapy channel 23 of the therapy tone 33 with the frequency $f_{CR3hta}$ or $f_{CR3hb}$ and therapy channel 24 of the therapy tone 34 with the frequency $f_{CR4hta}$ or $f_{CR4hb}$.

FIG. 23 shows the therapy tones 31 to 34 generated in the stimulation channels 21 to 24 plotted as a function of time t. The sequences are generated in a predetermined time grid comprised of successive cycles. The individual cycles are differentiated from one another by dotted lines in FIG. 23. Each cycle has a length $T_{stim}$. In each cycle in which a stimulation occurs, exactly one sequence of therapy tones 31 to 34 is generated in the stimulation channels 21 to 24, and exactly one therapy tone is generated in each of the stimulation channels 21 to 24, namely each sequence in the present example comprised of a series of four time-delayed therapy tones 31 to 34, each of which is generated in different stimulation channels 21 to 24 in particular, wherein the time lag may be based in particular on the starting points of the therapy tones 31 to 34.

It is possible to provide that the sequence of stimulation channels 21 to 24, in which the therapy tones 31 to 34 are generated within the respective sequence, e.g., after a certain number of cycles, is varied. It has proven advantageous, in particular at low stimulus intensities, if the sequence of simulation channels 21 to 24 is varied in a randomized manner for one cycle to the next. A difference in filling of the bars shown in FIG. 23, symbolizing therapy tones 31 to 34, indicates a variation in the order.

CR stimulation may be carried out continuously, for example, where sequences of therapy tones 31 to 34 are always generated in successive cycles. Alternatively, however, pauses may also occur during CR stimulation, in particular during entire cycles, in which there is no stimulation with therapy tones 31 to 34.

Each of the four stimulation channels 21 to 24 stimulates a respective one of the subpopulations 2 to 5 of the pathological neural population 1 illustrated in FIGS. 3 to 6. During cycles in which the sequences are constant, the respective therapy tone 31 to 34 is applied periodically with the period $T_{stim}$ in each of the stimulation channels 21 to 24. Therapy tones 31 to 34 produce a phase reset of the neural activity of the respective stimulated subpopulation 2 to 5. Furthermore, the time lag between therapy tones that are generated in different stimulation channels and follow one another directly in time within a sequence amounts to $T_{stim}/4$, because four stimulation channels 21 to 24 are used for the CR stimulation in the present example embodiment. For the general case of N (N≥2) stimulation channels used for the stimulation, the time lag between therapy tones generated in different stimulation channels within a sequence of directly chronologically successive therapy tones would amount to $T_{stim}/N$ (for example, there may be a deviation of up to +5%, +10% or ±20% from this value). The time lag $T_{stim}/N$ may relate to the initial points in time of the therapy tones. The therapy tones generated in different stimulation channels may be identical except for the different starting points and the frequencies.

The period $T_{stim}$, which indicates, first, the duration of a cycle and, second, the period, is repeated with the same sequences, and the therapy tones 31 to 34 generated in a respective stimulation channel 21 to 24 may be close to the middle period of the pathological oscillation of the neural population 1 with the pathological synchronous and oscillatory neural activity and/or may deviate from the middle period by up to ±5%, ±10% or ±20%. The frequency $f_{stim}=1/T_{stim}$ is typically in the range of 1 to 30 Hz. The period of pathological oscillation of the neural population 1 to be stimulated can be measured by way of EEG, for example. However, it is also possible to use values from the literature or empirical values based on the respective disease to be treated for the period of the pathological oscillation.

FIG. 23 shows as an example CR stimulation in which therapy tones are generated in four stimulation channels, namely N=4. However, the number N of stimulation channels may also be selected differently (with N≥2). CR stimulation may thus be carried out with exactly two stimulation channels, namely N=2, if stimulation with just two therapy tones is provided, for example, in the embodiment according to FIG. 13, or in order to test the first two therapy tones, which stimulate subpopulations 2 and 3 in the embodiments according to FIGS. 17 and 19. CR stimulation can also be carried out with exactly three stimulation channels, namely N=3. CR stimulation with three stimulation channels may be desirable in the embodiment according to FIG. 13 or in the embodiments according to FIGS. 17 and 19, and it may be used to test the CR stimulation with three therapy tones which stimulate, for example, subpopulations 2, 3 and 4. The stimulation pattern in CR stimulation over two or three stimulation channels corresponds essentially to the pattern illustrated in FIG. 23 except that each sequence comprise of two therapy tones for N=2 and/or three therapy tones for N=3 and thus two and/or three therapy tones are generated in cycles in which stimulation is carried out, and the time lag between therapy tones created within a sequence of chronologically directly successive therapy tones generated in different stimulation channels amounts to $T_{stim}/2$ and/or $T_{stim}/3$, respectively, according to one example embodiment.

The phase reset induced by the therapy tones can be verified as described above, and the therapy tones in CR stimulation produce a so-called reset of the phase of neural activity of the stimulated neurons. With the help of the measurement signals recorded with a sensor, for example, an EEG sensor or an MEG sensor, such a test can then be performed by the actual therapeutic CR neurostimulation. In order for a therapy tone, whose frequency has been determined using the methods described here, to induce a phase reset, for example, the amplitude, or the loudness of the therapy tone, can be varied until a phase reset of the neurons stimulated by the therapy tone is detected on the basis of the methods described below.

To do so, a signal which adequately represents the activity of the subpopulation stimulated over the $j^{th}$ stimulation channel is measured by way of a sensor. This signal is obtained either directly from the subpopulation by way of a noninvasive measurement, e.g., by way of EEG or MEG electrodes or by way of an invasive measurement, for example, by way of implanted electrodes, as surface EEG or as local field potential by way of depth electrodes. The signal can also be determined indirectly by measurement of a variable that correlates with the activity of the stimulated subpopulation. For example, EEG/MEG/LFP signals of the neural activity of a neural population closely associated with this population are suitable for this purpose.

Since neural signals typically contain rhythmic activity in different frequency bands, it is advantageous in such cases to determine the signal $x_j(t)$ which represents the pathological oscillatory activity of the subpopulation stimulated by the $j^{th}$ stimulation channel by way of band pass filtering or by wavelet analysis or by empirical mode decomposition.

A procedure that is streamlined for verifying a phase reset comprises of determining the average stimulus response. To do so, a therapy tone with identical parameters is generated at the times $\tau_1, \tau_2, \ldots, \tau_l$, the intervals between the individual therapy times $\tau_{k+1}-\tau_k$ should be large enough and should be randomized, namely not constant in order to avoid standardization processes (cf. document D29). The distances $\tau_{k+1}-\tau_k$ should typically be in the range of at least a factor of 10, or even better a factor of 100 of the middle period of the pathological isolation. The stimulus response average over all l is calculated according to the following equation:

$$\bar{x}_j(t) = \frac{1}{l}\sum_{k=1}^{l} x_j(\tau_k + t)$$

If the intervals $\tau_{k+1}-\tau_k$ between the individual therapy tones are large enough, then one does not obtain an average stimulus response in the pre-stimulus range, namely in the range before application of the respective therapy tone (cf. document D29). A phase reset can be detected if an average stimulus response can be detected, namely when there is a stimulus response different from zero in the post-stimulus range, namely in the range of t>0, where t=0 represents the initial point in time of the respective therapy tone. This can be determined by visual inspection. This can also be carried out by device 10, in particular the control unit 11 by taking into account the pre-stimulus distribution of $\bar{x}_j(t)$ or $|\bar{x}_j(t)|$ and determining a characteristic threshold value, for example, the $99^{th}$ percentile of the pre-stimulus distribution of $|\bar{x}_j(t)|$ or its maximum. For example, if the amount of the post-stimulus response exceeds this characteristic threshold value in principle or for a predetermined minimum period of time, for example, 20 ms, then the average response is different from zero. In this case, there may be a phase reset. In other words, the intensity of the therapy tones, in particular their amplitude, or loudness, would have to be increased until the post-stimulus response is different from a zero line. In addition to the methods presented here, which are streamlined but have proven successful in practice, other statistical tests with which those skilled in the art are familiar may be used for signal analysis.

Analysis of the phase permits a more accurate but more complicated variant for investigating whether the therapy tones induce a phase reset. To do so, the phase $\psi_j(t)$ of $x_j(t)$ is determined. This is done by way of a Hilbert transformation from the signal determined by way of band-pass filtering and/or empirical mode decomposition representing the pathological oscillatory activity. This empirical mode decomposition permits a parameter-independent determination of physiologically relevant modes in various frequency ranges in comparison with band-pass filtering (cf. document D30). The combination of empirical mode decomposition with the subsequent Hilbert transformation is referred to as Hilbert-Huang transformation (cf. document D31). The phase $\psi_j(t)$ can also be determined by way of wavelet analysis.

A phase reset occurs when the phase $\psi_j(t)$ is set at a preferred value by a therapy tone (with the start of the therapy tone at t=0) after a certain period of time. In other words, $\{\psi_j(\tau_k+t)\}_{k=1,\ldots,l}$, the distribution of values of the phase $\psi_j(t)$ obtained from the l stimulus responses has an accumulation point at the time t (relative to the start of the therapy tone at t=0). Those skilled in the art are familiar with those methods with which it is possible to detect that a distribution has an accumulation point (namely a peak). One method is to determine the phase reset index ρ(t) by way of circular average:

$$\phi(t) = \left| \frac{1}{l} \sum_{k=1}^{l} \exp[i\psi_j(\tau_k + t)] \right|$$

A phase reset occurs when φ(t) exceeds the maximum or the 99$^{th}$ percentile of the pre-stimulus distribution of φ(t) (at a point in time or within a small time window of 20 ms, for example).

In practice, analysis with the average responses $\bar{x}_j(t)$ has proven to be sufficient for some embodiments.

FIG. 24 shows schematically a device 40 for noninvasive acoustic stimulation of neurons with a pathological synchronous and oscillatory neural activity according to one embodiment of the invention. The device 40 can be operated as an acoustic stimulator by itself or in combination with a hearing device, e.g., combined in one component. The device 40 may also include an audiometer combined with it structurally or it may be equipped to receive data from an audiometer by wireless transmission, for example.

Acoustic stimulation signals, in particular therapy tones, are administered to the patient via an earbud or headphones 41 or a loudspeaker (or a hearing aid, a cochlear implant (which can deliver signals both acoustically and electrically), or another acoustic generator or transducer of a different design), wherein an earbud is a loudspeaker placed in the auditory channel. The earbud or headphones 41 is/are connected by cable 43 to a control unit 42 placed behind the ear with a (rechargeable) battery. A central control unit 44 with a (rechargeable) battery for operation by the patient may be connected to the components in and/or on the ear either by cable or by wireless connection.

FIG. 25 shows schematically a device 45, which is a refinement of the device 40 from FIG. 24. The device 45 contains, in addition to the components described above, noninvasively secured EEG electrodes 46 which are connected by cable 47, 48 to the behind-the-ear control unit 42. EEG signals are amplified and applied in the control unit 42.

The devices 10, 40 and 45 may also contain a unit for producing an audiogram and/or a unit for recording sensor signals, in particular EEG signals or MEG signals and/or for detecting information about the patient's condition, in particular VAS scales or tinnitus questionnaires, in addition to containing the device components already described above. However, it is also possible to provide that the audiogram, the sensor signals and/or the well-being information is/are detected by way of external devices and that the corresponding data is sent to the devices 10, 40 and 45 by way of an input/output unit.

The audiogram typically covers frequencies from 250 Hz to 8000 Hz or from 250 Hz to 16,000 Hz. It may be more advantageous to produce a high-pitch audiogram, e.g., up to 16,000 Hz if the dominant tinnitus frequency is at higher frequencies, in particular at more than 8000 Hz. In this case, the therapy tones will be higher than 8000 Hz and the choice of an optimal interval between them can involve adaptation to the respective hearing threshold.

Embodiments of this disclosure are not restricted to pure tone stimuli, but may use many other types of sound stimuli including stimuli with frequency components within the auditory filter bandwidth, and the inverse case of broadband signals with removal of frequency components within the auditory filter bandwidth. For instance, in the case of delivering CR stimulation with four different narrowband noise sound stimuli, replacement can be made of the ERB corresponding to the sine tone, as used so far, by an integral ERB belonging to the narrowband signal as described in the following and illustrated in FIG. 26.

Let $nb_1$ and $nb_2$ denote the lower and the upper frequency where the power of the narrowband signal is equal to half of its maximal value, namely 3 dB less power than at the peak as shown in FIG. 26, with $nb_2-nb_1$ specifying the band width at half maximum power. The value of 3 dB is arbitrary but is the most commonly used in engineering when specifying electronic filters. It also is the most commonly used in psychoacoustics because of the analogy to engineering filters, because this value is just over the just noticeable differences (jnd) for loudness that range from about 0.5 dB to 2.0 dB depending on frequency and because it is approximately the midpoint of the dB step size use for diagnostic threshold testing. To extract the perceptually prominent part of the power spectrum of a narrow band signal and separate it from possible additional noise and/or sound components not relevant to the disclosed stimulation mechanism, a 3 dB cutoff is used. The approach is stable with respect to variations of the cutoff level of up to 10%, up to 25% and even more. Then the integral auditory filter range of this narrow band noise stimulus reads:

$$[nb_{min}, nb_{max}]$$

where $$nb_{min} = \min\{f - 0.5 \cdot ERB(f,h)\}_{nb_1 \leq f \leq nb_2}$$

$$nb_{max} = \max\{f - 0.5 \cdot ERB(f,h)\}_{nb_1 \leq f \leq nb_2}$$

Because the ERB width depends on the frequency f, and also on the hearing threshold h, $nb_{min}$ is not necessarily equal to $nb_1 - 0.5 \cdot ERB(nb_1, h)$, and $nb_{max}$ is not necessarily equal to $nb_2 + 0.5 \cdot ERB(nb_2, h)$.

The integral ERB of the narrow band signal is then given by $nb_{max} - nb_{min}$. The sound used for stimulation may contain additional spectral components that do not exceed the half maximum ($P_{max}/2$) level. These frequency components generally are not relevant for measures of hearing sensitivity or pitch estimates under most circumstances and are also remote from the frequency region of interest. In that case one can determine the integral ERB in the same way as explained above. Instead of considering the spectral power of the narrow band sound signal one can also use the intensity and apply the same analysis.

Currently the diagnosis of primary tinnitus is an exclusionary diagnosis that is made after having ruled out diseases that may cause secondary tinnitus. No objective diagnosis of primary tinnitus is available. However, embodiments of this disclosure can be used for diagnostic purposes, too.

Abnormal neuronal synchrony is typically found in patients with primary tinnitus (see documents D3, D4, D9, D10, D20, D22, D23 and D25) and is reflected in abnormal spectral power of EEG signals and/or MEG signals and/or the corresponding brain source activity, e.g., determined with a BESA source montage approach (see document D34), and/or the corresponding current source density approach, e.g. calculated with sLORETA (see document D33). While the currently available findings have been shown to work on a group basis, namely able to separate groups of tinnitus patients from groups of healthy controls or groups of patients before and after successful treatment intervention (see documents D3, D4, D9, D20, D22, D23 and D25), so far a diagnostic test remains desired that allows these separations on an individual basis.

Some embodiments can be used for diagnostic purposes even with the surprising finding that the amount of abnormal neuronal synchrony may not be characteristic for primary tinnitus. Rather, the response of the abnormal, synchronized neuronal activity in the auditory cortex to desynchronizing test sound stimulation, e.g., acoustic CR neuromodulation, delivered in a hearing threshold adapted manner by way of this disclosure, can be used as a diagnostic marker for primary tinnitus.

To this end some embodiments are used in the following way:

(i) Assess the tinnitus frequency fr by way of a pitch matching procedure.

(ii) Calibrate up to 4 stimulation tones as described above (see FIGS. 13, 18 and 20).

(iii) Perform EEG and/or MEG recordings before, during and after stimulation.

(iv) Determine baseline power levels of delta and/or theta and/or alpha and/or gamma band levels, e.g., in 2-5 min spontaneous recordings, for example with eyes closed. Spectral power in the different frequency bands is separated by way of standard bandpass filters with dedicated band pass parameters, e.g., delta: 1-4 Hz, theta: 4-8 Hz, alpha: 8-13 Hz, gamma: 30-48 Hz, or by way of empirical mode decomposition (see documents D30 and D32) where the modes are assigned to different frequency bands by way of spectral analysis (see document D20).

(v) Perform test stimulation for, e.g., 5 min or 10 min or 15 min.

(vi) Assess the duration of significant after-effects at 60 s after cessation of stimulation, e.g., by using a 10 s window for time-varying spectral analysis and standard statistical tests (e.g. Wilcoxon matched pairs signed-rank test)

(vii) Findings indicative of tinnitus-related abnormal brain activity: Significant aftereffects to be observed after 60 s after cessation of stimulation:

Delta Band after-Effect:
(a) significant decrease of delta power below baseline from 60 still at least 240 s after 15 min desynchronizing sound stimulation.
(b) significant decrease of delta power below baseline from 60 s till at least 120 s after 10 min desynchronizing sound stimulation.
(c) significant decrease of delta power below baseline from 60 still at least 90 s after 5 min desynchronizing sound stimulation.

Gamma Band after-Effect:
(a) significant decrease of gamma power below baseline from 60 still at least 240 s after 15 min desynchronizing sound stimulation.
(b) significant decrease of gamma power below baseline from 60 s till at least 120 s after 10 min desynchronizing sound stimulation.
(c) significant decrease of gamma power below baseline from 60 still at least 90 s after 5 min desynchronizing sound stimulation.

Alpha Band after-Effect:
(a) significant increase of gamma power below baseline from 60 still at least 120 s after 15 min desynchronizing sound stimulation.
(b) significant increase of gamma power below baseline from 60 s till at least 90 s after 10 min desynchronizing sound stimulation.
(c) significant increase of gamma power below baseline from 60 still at least 75 s after 5 min desynchronizing sound stimulation.

After-effects can be assessed unilaterally, e.g., for the auditory cortex of the same side, in case of unilateral tinnitus or bilaterally (by taking the mean of both sides) in patients with bilateral tinnitus. Instead of current source density or brain source activity, reconstructed after-effects can also be determined by using EEG and/or MEG signals (without any inverse analysis techniques).

These after-effect markers can be used in isolation or in combination (to increase their diagnostic specificity). If used in isolation the delta-band after-effect marker is most specific. The most robust pair of markers is the delta/gamma marker pair, since the alpha band activity may be altered due to non-disease related influences, e.g., relaxation etc.

Some embodiments can also be used for diagnostic purposes and/or to monitor therapeutic outcome in the course of a treatment. Both purposes can leverage that the amount of abnormal neuronal synchrony, in particular, in the delta frequency band (e.g., 1-4 Hz) may not be sufficient to separate healthy controls from patients with primary tinnitus on a patient-to-patient basis.

By the same token, some embodiments can also be used to monitor therapeutic outcome in the course of a treatment. To this end the after-effect markers as explained above, especially the delta band marker, are assessed at each visit. Positive therapeutic effect translates into a decrease of the duration of the test stimulation after-effects.

In the following auditory filter theory will be explained. Auditory filter theory is based on the concept that the auditory system functions as a spectrum analyzer that is able to analyze the level, typically on a dB scale, of broad band acoustic signals such as speech, music and noise to provide information on the spectral content of the signal. It is based on the fundamental engineering concept of a band pass filter that can have a wide variety of shapes and fundamental operational differences. However, an auditory filter typically is described as having a center frequency $f_C$, a low cut-off frequency $f_L$, a high cut-off frequency $f_H$, a bandwidth BW centered on this frequency, $BW=f_H-f_L$ at a point 3 dB lower than the $f_C$, an out of band rejection rate=dB/octave, and a variety of temporal effects such as phase changes associated with different portions of the filter. $f_L$ and $f_H$ are the lower and upper edges of the bandwidth, respectively.

Auditory filter theory can specify a particular filter that can be described both subjectively and mathematically and then represents the auditory system as a set of adjacent auditory filters. The center frequency $f_C$ of an auditory filter initially is determined by the peripheral auditory system, specifically the external ear, middle ear, and most prominently, the cochlea. The bandwidths BW and filter shapes are determined from a variety of psychoacoustic and physiologic measures with descriptions that can include detailed mathematical representations that specify level, frequency and phase effects. For acoustic tonal stimulation, and by analogy the tinnitus percept, the fundamental concept is that an acoustic signal is filtered in the spectral domain by the auditory filter to establish the spectral resolution of the resulting auditory percept that is associated with various locations in the auditory system beginning at the peripheral ear and extending to central nervous system locations up to the level of the auditory cortex.

Auditory filter theories are used to explain several abilities of the auditory system including frequency sensitivity and selectivity (e.g., frequency tuning curves), speech perception (e.g., vowel discrimination), music perception (e.g., timbre), source identification (e.g., male vs female speaker) and selective attention (e.g., enhanced ability to attend to a specific signal in the presence of non-specific noise).

Auditory filter theories have employed a wide variety of mathematical representations. The physical acoustic waveform in the environment can be described as the amount of time between specified oscillations in the waveform, period p in msec. The number of oscillations per unit time, frequency f in $Hz=1/p$. The values can be expressed on a linear scale or on a logarithmic scale, $\log(p)$ and $\log(f)$. The logarithmic scales have the same absolute value, $\log(f)=-\log(p)$. A musical octave scale is specified if the log base value=2 (see document D14).

Auditory filter theories can employ a wide variety of perceptual phenomena that can be described mathematically as well. Musical pitch can be specified as being proportional to $\log(f)$ with the musical octave=$\log_2(f/127.09)$ multiplied by 12 for semi-tones or by 1200 for cents.

Auditory pitch also can be specified based on psychoacoustically derived division of frequency ranges into perceptually equal intervals or judgements of the frequency of a tone as half as high as a comparison tone (see document D6). One mel m=one thousandth the pitch of a 1 kHz tone, further specified as $m=1127 \ln(1+f/700)$, or the inverse: $f=700 [\exp(m/1127)-1]$.

Auditory filter theory also can use the concept of critical bandwidth $B_c$ derived from either masking (see document D19) or loudness summation psychoacoustic measures (see document D28). Masking involves simultaneously presenting a tonal signal S with a broadband noise N where selectively the frequencies of N that fall within a critical band contribute to masking of the signal. The larger the critical bandwidth, the lower the signal-to-noise ratio S/N and the more the signal is masked. Loudness summation involves measurement of loudness changes with increasing signal bandwidth.

The Bark, B, scale is a psychoacoustically-derived frequency scale where equal frequency distances correspond with equal perceptual distances (see document D24). A scale from 1 to 24 corresponds to the first 24 critical bands. The critical band rate scale, z, (in bark)=$[26.81/(1+1960/f)]-0.53$, with f in Hz. Critical bandwidth (in Hz), $B_c=52548/(z^2-52.56 z+690.39)$.

Auditory filter theories are useful for understanding a wide variety of auditory phenomena including sound localization ability, the physiology of the cochlea and central nervous system processing of auditory signals and tinnitus.

For acoustic tonal stimulation for tinnitus intervention, and by analogy the pitch matched frequency of the tinnitus percept, a tonal signal can be considered analogous to the center frequency of an auditory filter. The auditory filter characteristics, such as filter bandwidth, can be used to represent specific spatial representation in the auditory system. Because the spatial representation of these signals is systematically organized at the level of the cochlea and sequentially through the eighth cranial nerve, the auditory neural centers in the brainstem, and all the way to the auditor cortex in the temporal lobe, acoustic coordinated reset tinnitus intervention signals are tightly controlled and the effects are better understood.

The auditory filter models cited above refer to normal hearing. An adjustment for hearing loss can take two forms. In the case of an auditory filter model that contains both hearing threshold and suprathreshold information, the hearing loss adjustment can be made from the normal hearing data. In the frequency tuning curve model, e.g., where the hearing threshold can be specified as the minimum point of the frequency tuning curve and the frequency selectivity is specified for all suprathreshold levels of stimuli, an adjustment for hearing loss can be estimated by re-specifying the minimum point on the curve based on the magnitude of the hearing loss and no additional measures are involved other than the existing diagnostic audiogram. This estimate would rely on the assumption that the individual's tuning curve for signals above threshold would be close to the normal frequency tuning curve and the assumption that the actual change in hearing sensitivity would be accurately estimated from the diagnostic audiogram, two assumptions not based on direct measures. In the case of an auditory filter model based on data measured in persons with sensorineural hearing loss, the ERB model, or the frequency tuning curve model e.g., the adjustment for sensorineural hearing loss, can be made from published average measured data secondary to the original auditory filter theory. The hearing loss range can be set for the ERB analysis based on published actual averaged data from hearing loss subjects though this is not required, and ERB bandwidths can be specified for all levels of hearing loss. Finally, regardless of which auditory filter model is employed, the actual auditory filter can be measured in an individual patient with a variety of either psychoacoustic or physiologic methods.

Instead of using the mathematical formulas presented above, some embodiments can also use actual measures of the auditory filters for a particular patient. The disadvantage of measuring auditory filters individually is the time involved. Alternatively, as a hybrid compromise, some embodiments can provide stimuli initially determined with a model-based auditory filter (e.g., ERB) calculated with the formulas presented above. At subsequent visits (e.g., for re-calibrating the sound treatment) the auditory filters can be measured initially at the principal diagnostic frequencies, e.g., at 250 Hz, 500 Hz, 750 Hz, 1 kHz, 1.5 kHz, 2 kHz, 3 kHz, 4 kHz, 6 kHz, 8 kHz, 10 kHz, 12.5 kHz, 16 kHz or alternatively with more fine-grained measures around the tinnitus frequency $f_T$ to gradually replace the model-based estimates of the auditory filters with individually measured auditory filters visit by visit. Due to the extra time for these additional measures this hybrid procedure can be selectively applied to patients who do not respond sufficiently well to the initial model based sound therapy.

The following provided further details for explaining and implementing some embodiments of this disclosure.

Analysis of the Spacing of the Standard CR Tones:

In a proof of concept study (document D22) 63 patients with primary tinnitus received acoustic coordinated reset (CR) therapy. The therapy is composed of four tones $f_1$, $f_2$, $f_3$, $f_4$, spaced around the pitch of the tinnitus $f_T$ with a well-defined pattern and implemented several hours per day for 12 weeks and 24 weeks. The mean tinnitus reduction was substantial but with a range of effective reductions across individual subjects. The purpose of the following is to analyze the individual results of this study with respect to the frequency spacing of the tones.

The frequencies of CR tones used in the proof of concept study (D22) were a fixed percentage of a tone matched to the pitch of the tinnitus with two placed below the tinnitus frequency and two placed above the tinnitus frequency. The tinnitus pitch and the four CR therapy tones were specified by:

$f_T$=tinnitus frequency determined by pitch matching $$f_1 = c_1 f_T = 0.766 f_T$$

$$f_2 = c_2 f_T = 0.9 f_T$$

$$f_3 = c_3 f_T = 1.1 f_T$$

$$f_4 = c_4 f_T = 1.4 f_T$$

Frequency Spacing of Standard CR Tones:

To quantify the frequency spacing of the tones, the analysis is based on auditory filter theory where the relevant auditory processing for a single tone is a band width centered on the tone. In this case the corresponding rectangular band width (ERB) (D11; D17) was used for the tinnitus frequency and for each of the four tones. To determine the frequency spacing and overlap of the ERBs between the different CR tones and the tinnitus frequency, determination is made of the spacing of their corresponding ERBs and adjustment is made of these ERBs further based on the hearing level at each frequency for each subject. To this end the following notations are introduced in FIG. 27.

FIG. 27 shows notations of band edges and center frequencies of ERBs and each of the four CR tones as an example.

The x-axis is the frequency (f) axis. $a_j$ and $b_j$ denote the lower and upper edge of an ERB($f_j$), the ERB belonging to the j-th CR tone.

Consideration is made of two different approximations for the corresponding rectangular bandwidth for normal hearing ($ERB_N$):

(i) $1^{st}$ ERB approximation (D17):

$$ERB(\tilde{f}) = 6.23 \tilde{f}^2 + 93.39 \tilde{f} + 28.52$$

$\tilde{f}$ is in kHz, i.e.: $f = \tilde{f} \cdot 1000$, where f and ERB are in Hz. Accordingly, one obtains $$ERB(f) = \frac{6.32}{10^6} f^2 + \frac{93.39}{10^3} f + 28.52$$

This approximation is valid for f in the range from 100 Hz to 6.5 kHz.

(ii) $2^{nd}$ ERB approximation (D11):

$$ERB(\tilde{f}) = 24.7(4.37 \tilde{f} + 1)$$

$\tilde{f}$ is in kHz, i.e.: $f = \tilde{f} \cdot 1000$, where f and ERB are in Hz. Accordingly, one obtains $$ERB(f) = 2\eta f + 24.7 \quad \text{(Eq.A)},$$

where $2\eta = 107,939/1000$. This approximation is valid for moderate sound levels and for f in the range from 100 Hz to 10 kHz.

The frequency range of validity is significantly greater than that of the $1^{st}$ approximation. In addition, the $2^{nd}$ approximation appears to be superior in terms of a broader coverage of the admissible tinnitus frequency range combined with a streamlined mathematical model. Accordingly, the $2^{nd}$ ERB approximation is used for the following analysis.

Hearing Threshold Adapted ERB:

In a next step, account is taken of the impact of hearing loss on the ERB. D18 provides data for 2 kHz, 4 kHz, and 6 kHz and absolute hearing threshold between 0 and 80 dB HL. Based on their data, in a first approximation, for the range between 0 and 50 dB HL the dependence of ERB on hearing loss h can be modeled by $$ERB(h) = ERB_0 \cdot c(h)$$

where $ERB_0$ denotes the ERB at normal hearing, and $$c(h) = 1 + h/50$$

and h is hearing threshold in dB HL. Note, for frequencies other than 2 kHz, 4 kHz, and 6 kHz, this model can be considered as a first approximation.

FIG. 28 (upper plot) shows the ERB at normal hearing (thin line) as well as the hearing threshold adapted ERB (solid line). Symbols indicate frequencies at which the audiogram was measured. Lower plot shows the corresponding audiogram (linearly interpolated on a logarithmic frequency axis).

For the sake of illustration, assume a homogenous hearing loss, e.g., a hearing loss that is the same magnitude across frequency. The corresponding ERBs of the tinnitus frequency as well as CR tones #1, . . . , #4 (displayed relative to tinnitus frequency) are plotted for h=0 dB HL (FIG. 29, left panel).

The frequencies of the CR therapy tones $f_1$, $f_2$, $f_3$, $f_4$ used in the proof of concept study (D22) are specified by:

$f_T$=tinnitus frequency determined by pitch matching $$f_1 = c_1 f_T = 0.766 f_T$$

$$f_2 = c_2 f_T = 0.9 f_T$$

$$f_3 = c_3 f_T = 1.1 f_T$$

$$f_4 = c_4 f_T = 1.4 f_T$$

The left panel in FIG. 29 shows the tinnitus frequency-dependent ERB edges divided by the tinnitus frequency for the case of normal hearing (0 dB HL for all frequencies), respectively. For instance, the upper and lower edge of the uppermost, light shaded area (belonging to the fourth CR tone, "CR4") reads $b_4/f_T$ and $a_4/f_T$, respectively.

In relation to the tinnitus ERB, namely the ERB belonging to the frequency $f_T$, the ERBs of the different CR tones (CR1, . . . , CR4) are not symmetrically aligned on the (relative) frequency axis. Considering ERBs as quantifying the tonotopic pathways to neuronal populations in the central auditory system, e.g., the auditory cortex, it is hypothesized that a non-symmetrical arrangement of ERBs of CR tones corresponds to a non-symmetric, (spatially) non-balanced stimulation of neuronal sub-populations in the auditory cortex by the different tones CR1, . . . , CR4. According to computational and pre-clinical findings in a larger number of studies, a spatially symmetric arrangement of stimulated cortical sub-populations is optimal: The spacing (in cortical coordinates) of the sub-populations (belonging to the entire population involved in the abnormal neuronal synchronization process) affected by the different subpopulations should be intermediate, as opposed to completely overlapping or completely separate. The spatial overlap of the sub-populations stimulated by the tones should be weak, but the sub-populations should still share significant synaptic connections and, hence, not be located far away from each other.

In addition, FIG. 29 shows the ERB arrangement for the case of standard CR tones f_1, . . . , f_4 with a typical hearing loss (upper right panel) with hearing threshold as displayed in the lower right panel. Overall (e.g., across all tinnitus frequencies) the arrangement of the different CR ERBs (e.g., ERBs belonging to the different CR tones) is neither spatially well-balanced nor spatially symmetric. Furthermore, the overlaps and/or gaps between the different ERBs depend on the tinnitus frequency $f_T$. This aspect is relevant because for approximately 85% of the tinnitus patients the tinnitus frequency $f_T$ decreased during the course of the CR treatment, so the CR tones have to be re-adjusted (by tinnitus pitch matching) on a regular basis. Accordingly, during the course of the treatment in an individual patient, the spacing of the CR tone ERBs may change significantly. It is hypothesized that the efficacy of the CR treatment may vary accordingly.

Next re-analysis is made of data of an observational study (a study without control/placebo/sham control group). The subjective tinnitus frequency of all patients treated with acoustic CR neuromodulation in that study was pitch matched with the same procedure as in the proof of concept study (D22).

Calculation of the Relative ERB Overlap:

The tinnitus ERB (e.g., the ERB belonging to the tinnitus frequency $f_T$) is used as a reference for calculating the relative overlap or relative separation (gap) of each of the CR therapy tone ERBs as illustrated in FIG. 30.

The relative overlap/gap between the ERB of the j-th CR tone (j=1, . . . , 4) and the tinnitus ERB reads $$\rho(f_T, f_j) = \begin{cases} \dfrac{b_T - a_j}{ERB(f_T)}, & f_T < f_j \\ \dfrac{b_j - a_T}{ERB(f_T)}, & f_T \geq f_j \end{cases}$$

$0 < \rho(f_T, f_j) \leq 1$ if $ERB(f_T)$ and $ERB(f_j)$ overlap.

$0 = \rho(f_T, f_j)$ if $ERB(f_T)$ and $ERB(f_j)$ just touch.

$\rho(f_T, f) < 0$ if $ERB(f_T)$ and $ERB(f_j)$ do not overlap, and there is a gap between both ERBs. Since the ERB is specified on a linear frequency axis (D11; D17), calculation is made of the relative ERB overlaps on a linear frequency axis. Calculating the relative ERB overlaps on a logarithmic frequency axis does not yield different subgroups with pronounced and statistically significant differences in therapeutic outcomes.

Relative ERB Overlaps/Gaps for VAS Loudness Scores:

To study whether particular relative ERB overlaps/gaps $\rho(f_T, f_j)$ might be associated with better treatment outcome, FIG. 31 plots the distributions of the number of super responders, e.g., the subjects with VAS for loudness (VAS-L) changes >15 (y-axis) in relation to $\rho(f_T, f_j)$ for all four CR tones $f_1, \ldots, f_4$ (rows 1, . . . , 4) after 12 weeks (column 1) and after 24 weeks (column 2) and the corresponding distributions obtained by a standard smoothing procedure (column 3). Super responders are patients who respond particularly well, e.g., have a decrease of their VAS-L score (e.g., score for VAS loudness) of at least 15. (Very similar distributions are obtained for responders, as opposed to super responders, e.g., patients with a decrease of at least 10.) For CR tones 2 and 3 the super responders show a prominent peak in the distribution at larger relative overlap values (at approx. 0.45 and 0.55), whereas for CR tones 1 and 4 super responders show a prominent peak in the distribution at smaller relative gap values (at approx. −0.25 and −0.65). The smoothened distributions are obtained to determine peak maxima (for illustration).

Relative ERB Overlaps/Gaps for VAS Annoyance Scores:

Very similar distributions are obtained for the distribution of super responders based on the VAS scores for annoyance (VAS-A).

If determination is made of the distribution of the super responders for VAS-L and VAS-A by calculating $\rho(f_T, f_j)$ for CR tones 2 and 3 (j=2,3) and $\rho(f_1, f_2)$, e.g., the relative ERB overlap between the neighboring CR tones 1 and 2, and $\rho(f_3, f_4)$, e.g., the relative overlap between the neighboring CR tones 3 and 4, one obtains very similar results. In contrast and remarkably, if $ERB(f_T)$, the tinnitus ERB, is not used as reference for the normalization in the formula for the relative ERB overlap/gap $\rho$, one obtains significantly different distributions of the super responders (closer to a flat distribution, considerably less pronounced peak).

ERB Overlap Based Subgroup Analysis of Treatment Outcome:

The entire patient population (N=66) is divided in (i) patients having relative overlaps $\rho(f_T, f_j)$ for all four CR tones j=1, . . . , 4 that are close to the relative ERB overlaps/gaps given by the peaks in the super responder distributions, which will be called "optimal" relative ERB overlaps/gaps, and (ii) all other patients and results are plotted in FIG. 32.

Subgroup Analysis of the Entire Population:

The upper two panels show whisker plots of the VAS-L and VAS-A values at baseline (prior to treatment), after 12 weeks and after 24 weeks of treatment with acoustic CR neuromodulation for the two subgroups of the entire population: the subgroup of patients with optimal relative ERB overlaps and all other patients.

VAS-A: At baseline both subgroups have similar VAS distributions, whereas after both 12 weeks and after 24 weeks the reduction of VAS-A scores is significantly stronger in the subgroup with optimal relative ERB overlaps/gaps.

VAS-L: At baseline both subgroups have similar VAS distributions, whereas after 24 weeks the reduction of VAS-A scores is significantly stronger in the subgroup with optimal relative ERB overlaps/gaps.

Subgroup Analysis of the Super Responders:

The lower two plots show whisker plots of the VAS-L and VAS-A values at baseline (prior to treatment), after 12 weeks and after 24 weeks of treatment with acoustic CR neuromodulation for the two subgroups of the super responders: subgroup of super responders with optimal relative ERB overlaps and all other super responders.

VAS-A: At baseline both subgroups of super responders have similar VAS distributions, whereas after 12 weeks the reduction of VAS-A scores is significantly greater in the subgroup of super responders with optimal relative ERB overlaps/gaps.

VAS-L: There was no significant difference between the two subgroups of super responders.

Comparing the subgroup analysis of all patients (upper plots) with the subgroup analysis of the super responders (lower plots) it is concluded that all patients, not just the super responders, have a greater benefit if the CR tones have optimal relative ERB overlaps.

ERB Based Subgroup Analysis of Responder Rates:

Determination is then made of the responder rate dependent on the relative ERB overlap/gap (FIG. 33). To this end, calculation is made of the number of responders, super responders and non-responders with optimal relative ERB overlap/gap after 12 weeks (A12) and 24 weeks (A24) of therapy as opposed to the number of all other responders, super responders and non-responders after 12 weeks (B12) and 24 weeks (B24) of therapy. The left and right panels refer to the decrease of VAS-A and VAS-L, respectively. Intriguingly, the responder rate is greater for patients without optimal relative ERB overlap/gap.

In FIG. 34 whisker plots are shown of the distribution of the hearing thresholds at CR tones $f_1, \ldots, f_4$ and at the tinnitus frequency $f_T$ for the subgroup of patients with optimal relative ERB overlap/gap and for the subgroup of all other patients (left panel). The right panel shows the corresponding distributions for the VAS-A and VAS-L super responders.

Patients with optimal relative ERB overlap/gap have significantly greater hearing impairment. Accordingly, it is hypothesized that greater hearing impairment leads to greater errors of the tinnitus pitch matching procedure that, in turn, causes a reduced responder rate. Stated in another way, if the tinnitus frequency is properly assessed by way of the pitch matching the treatment outcome is significantly stronger with optimal ERBs. However, it may be more difficult to obtain a reliable pitch match in patients with pronounced hearing impairment.

Translational Consequence:

To improve the treatment, in a first step, one could use the optimal relative ERB overlaps/gaps to determine the frequencies $f_1, \ldots, f_4$ based on the tinnitus frequency $f_T$ (obtained by pitch matching). In a first approximation, in patients with pronounced hearing impairment these hearing threshold adapted CR tones are similar to the standard CR tones (with fixed ratio to the tinnitus frequency). In contrast, in normal hearing patients the determination of CR tones based on the calculation of the relative ERB overlap/gap will mimic the relative ERB overlap/gap observed in hearing impaired patients treated with standard CR tones. Because tinnitus pitch matching is more reliable in patients with normal (or moderate) hearing impairment as opposed to in patients with pronounced hearing impairment, it is hypothesized that acoustic CR neuromodulation with optimal relative ERB overlaps/gaps will lead to improved treatment outcome.

Recalling the arrangement of the hearing threshold adapted ERBs of the standard CR tones $f_1, \ldots, f_4$ (from FIG. 29) for normal hearing (left panel) and a typical hearing loss (right panel), the case for standard CR tones $f_1, \ldots, f_4$ with a typical hearing loss is replotted in FIG. 35 (left panel). For comparison, the right panel of FIG. 35 shows the hearing threshold adapted ERBs in a patient with identical hearing loss (lower right panel) and optimal ERB overlaps (as determined from the re-analysis of the clinical data above). Due to the procedure of hearing threshold adaptation based on the optimal relative ERB overlap/gap, the relative ERB gaps/overlaps between adjacent CR tones hardly vary with tinnitus frequency $f_T$. Hence, in a first approximation relative ERBs between treatment tones no longer depend on the tinnitus frequency $f_T$ and, thus, would no longer vary in the course of the treatment (e.g., if it is assumed that the pitch matching is ideal and the tinnitus frequency is reduced by the treatment). However, the mutual arrangement of the different ERBs is still not symmetric and well-balanced in the hearing loss case (right panel). For instance, between $ERB(f_3)$ and $ERB(f_4)$ there is a gap at all frequencies, whereas $ERB(f_1)$ and $ERB(f_2)$ there is overlap at all frequencies.

Figure 36:
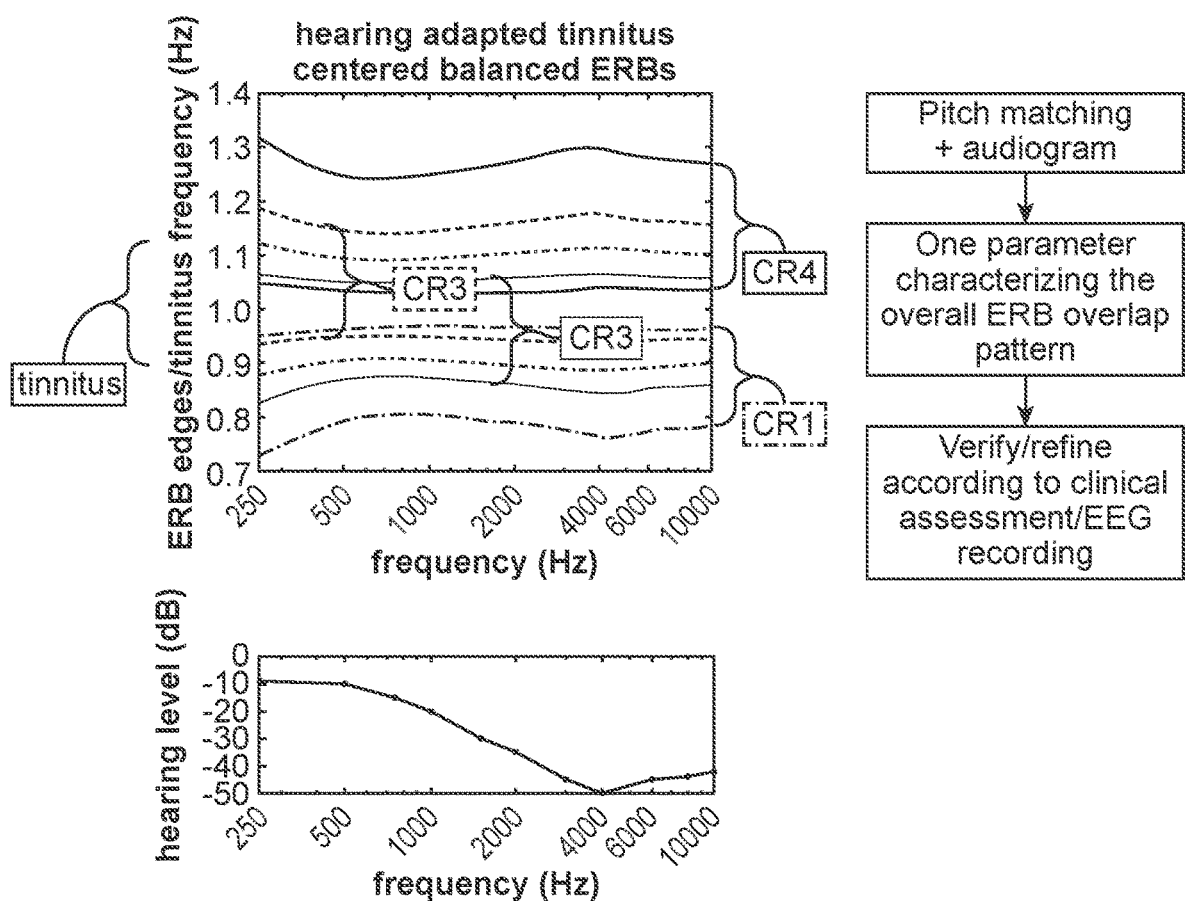

It is hypothesized that a more effective CR treatment can be achieved by way of a symmetric, well-balanced arrangement of the ERBs of the CR tones. Based on the patient's audiogram this can be achieved, for instance, with just two parameters: (i) the tinnitus frequency $f_T$ and (ii) a target ERB which is $\sigma \cdot ERB(f_T)$, where $\sigma$ is a stretching factor that ensures that the CR tone spacing does not get too narrow. FIG. 36 shows an example of a symmetric ERB arrangement for $\sigma=1.5$ (upper panel) for the patient with the typical hearing loss (lower panel). The stretching factor can be calibrated based on treatment outcome (even by the patient's individual results) or (in a more sophisticated way) by way of EEG recordings e.g., assessing the CR-induced reduction of auditory delta power. The dependence of EEG delta power suppression on the stretching factor $\sigma$ can be assessed to establish a range of $\sigma$ values suitable for clinical applications.

The mutual overlap $\xi$ of $ERB(f_2)$ and $ERB(f_3)$ (relative to smaller ERB) is identical with overlap of $ERB(f_1)$ and $ERB(f_2)$ (relative to inner ERB, e.g., $ERB(f_2)$) and identical with overlap of $ERB(f_3)$ and $ERB(f_4)$ (relative to inner ERB, e.g., $ERB(f_3)$) (mutually symmetric arrangement).

An objective is to find maximal relative overlap parameter $\xi$ which fulfills
 lowest CR tone ($f_1$) is greater than lower edge of stretched tinnitus ERB, e.g., $\sigma \cdot ERB(f_T)$.
 highest CR tone ($f_4$) is smaller than higher edge of stretched tinnitus ERB.

LITERATURE

D1 I. Adamchic, B. Langguth, C. Hauptmann, P. A. Tass: Psychometric evaluation of Visual Analog Scale for the assessment of chronic tinnitus. Am. J. Audiol., 21, 215-225 (2012)

D2 I. Adamchic, P. A. Tass, B. Langguth, C. Hauptmann, M. Koller, M. Schecklmann, F. Zeman, M. Landgrebe: Linking the Tinnitus Questionnaire and the Clinical Global Impression: Which differences are clinically important? Health and Qol Outcomes, 10, 79 (2012)

D3 I. Adamchic, T. Toth, C. Hauptmann, P. A. Tass: Reversing pathologically increased EEG power by acoustic coordinated reset neuromodulation. Human Brain Mapping, 35, 2099-2118 (2014)

D4 I. Adamchic, B. Langguth, C. Hauptmann, P. A. Tass: Abnormal brain activity and cross-frequency coupling in the tinnitus network. Front. Neurosc., 8, 284 (2014)

D5 A. Axelsson, A. Ringdahl: Tinnitus—a study of its prevalence and characteristics. Br. J. Audiol., 23, 53-62 (1989)

D6 L. L. Beranek: Acoustic Measurements, New York: Wiley (1949)

D7 C. R. Butson, C. C. Mcintyre: Current steering to control the volume of tissue activated during deep brain stimulation. Brain Stimul., 1(1), 7-15 (2008)

D8 J. J. Eggermont, L. E. Roberts: The neuroscience of tinnitus. Trends Neurosci., 27, 676-682 (2004)

D9 J. J. Eggermont, P. A. Tass: Maladaptive neural synchrony in tinnitus: origin and restoration. Front. Neurol., 6, 29 (2015)

D10 J. J. Eggermont: The auditory cortex and tinnitus—a review of animal and human studies. European Journal of Neuroscience, 41, 665-676 (2015)

D11 B. R. Glasberg, B. J. C. Moore: Derivation of auditory filter shapes from notched-noise data. Hearing Research, 47 (1-2), 103-138 (1990)

D12 C. Hauptmann, A. Stroebel, M. Williams, N. Patel, H. Wurzer, T. von Stackelberg, U. Brinkmann, B. Langguth, P. A. Tass: Acoustic Coordinated Reset Neuromodulation in a Real Life Patient Population with Chronic Tonal Tinnitus. BioMed Res. Int. Article ID 569052 (2015)

D13 C. Hauptmann, A. Wegener, H. Poppe, M. Williams, G. Popelka, P. A. Tass: Validation of a Mobile Device for Acoustic Coordinated Reset Neuromodulation Tinnitus Therapy. J. Am. Acad. Audiol. (in print)

D14 IEC 61260: Electroacoustics—Octave-band and Fractional-Octave-Band Filters, Geneva, Switzerland: International Electrotechnical Commission (1995)

D15 B. Langguth: Tinnitus: the end of therapeutic nihilism. Lancet, 379, 1926-1928 (2012)

D16 B. Lysyansky, O. P. Popovych, P. A. Tass: Desynchronizing anti-resonance effect of the m:n ON-OFF coordinated reset stimulation. Journal of Neural Engineering, 8, 036019 (2011)

D17 B. C. J. Moore, B. R. Glasberg: Suggested formulae for calculating auditory filter bandwidths and excitation patterns. Journal of the Acoustical Society of America, 74, 750-753 (1983)

D18 B. C. J. Moore, D. A. Vickers, C. J. Plack, A. J. Oxenham: Inter-relationship between different psychoacoustic measures assumed to be related to the cochlear active mechanism. J. Acoust. Soc. Am., 106, 2761-2777 (1999)

D19 R. D. Patterson: Auditory filter shapes derived with noise stimuli. J. Acoust. Soc. Am., 59, 640-654 (1976)

D20 A. N. Silchenko, I. Adamchic, C. Hauptmann, P. A. Tass: Impact of acoustic coordinated reset neuromodulation on effective connectivity in a neural network of phantom sound. Neuroimage, 77, 133-147 (2013)

D21 P. A. Tass: A model of desynchronizing deep brain stimulation with a demand-controlled coordinated reset of neural subpopulations. Biol. Cybern., 89, 81-88 (2003)

D22 P. A. Tass, I. Adamchic, H.-J. Freund, T. von Stackelberg, C. Hauptmann: Counteracting tinnitus by acoustic coordinated reset neuromodulation. Restorative Neurology and Neuroscience, 30, 137-159 {2012)

D23 P. A. Tass, L. Qin, C. Hauptmann, S. Doveros, E. Bezard, T. Boraud, W. G. Meissner: Coordinated reset neuromodulation has sustained after-effects in parkinsonian monkeys. Annals of Neurology, 72, 816-820 (2012)

D24 H. Traunmuller: Analytical expressions for the tonotopic sensory scale. J. Acoust. Soc. Am., 88, 97-100 (1990)

D25 N. Weisz, S. Moratti, M. Meinzer, K. Dohrmann, T. Elbert: Tinnitus perception and distress is related to abnormal spontaneous brain activity as measured by magnetoencephalography. PLoS Med, 2(6), 546-553 (2005)

D26 J. Wang, S. Nebeck, A. Muralidharan, M. D. Johnson, J. L. Vitek, K. B. Baker: Coordinated reset deep brain stimulation of subthalamic nucleus produces long-lasting, dose-dependent motor improvements in the 1-Methyl-4-phenyl-1,2,3,6-tetrahydropyridine non-human primate model of parkinsonism. (published online, 2016)

D27 M. Williams, C. Hauptmann, N. Patel: Acoustic CR neuromodulation therapy for subjective tonal tinnitus: a review of clinical outcomes in an independent audiology practice setting. Front. Neural., 6, 54 (2015)

D28 E. Zwicker, G. Flottorp and S. S. Stevens: Critical bandwidth in loudness summation. J. Acoust. Soc. Am., 29, 548-557 (1957)

D29 P. A. Tass: Transmission of stimulus-locked responses in two coupled phase oscillators. Phys. Rev. E 69, 051909-1-24 (2004)

D30 N. E. Huang et al.: The empirical mode decomposition and the Hilbert spectrum for nonlinear and non-stationary time series analysis. Proc. R. Soc. A: Math. Phys. Eng. Sci., 454, 903-995 (1998)

D31 N. E. Huang et al.: A confidence limit for the empirical mode decomposition and Hilbert spectral analysis. Proceedings of the Royal Society of London Series A, 459, 2317-2345 (2003)

D32 W. Huang, Z. Shen, N. E. Huang, Y. C. Fung: Engineering analysis of biological variables: an example of blood pressure over 1 day. Proc. Nat. Acad. Sci. USA, 95, 4816-4821 (1998)

D33 R. D. Pascual-Marqui: Standardized low-resolution brain electromagnetic tomography (sLORETA): technical details. Methods Find. Exp. Clin. Pharmacol. 24 Suppl. D, 5-12 (2002)

D34 M. Scherg, N. Ille, H. Bornfleth, P. Berg: Advanced tools for digital EEG review: virtual source montages, whole-head mapping, correlation, and phase analysis. J. Clin. Neurophysiol., 19(2), 91-112 (2002)

EXAMPLE EMBODIMENTS

Embodiment 1

A device (10) for stimulation of a patient with acoustic stimulation signals, comprising:
a stimulation unit (12) configured to generate acoustic stimulation signals, and
a control unit (11) connected to the stimulation unit (12) and configured to control the stimulation unit (12), wherein the control unit (11) is configured to
determine a bandwidth of an auditory filter with a frequency of a predetermined tone as a center frequency, wherein the bandwidth represents a reference bandwidth,
determine a frequency of a first acoustic therapy signal, such that a measure of coverage between the reference bandwidth around the frequency of the predetermined tone and a first bandwidth of an auditory filter with the frequency of the first acoustic therapy signal as a center frequency assumes a predetermined first value, and
control the stimulation unit (12) such that the stimulation unit (12) generates the first acoustic therapy signal.

Embodiment 2

The device (10) according to Embodiment 1, wherein:
the reference bandwidth of the auditory filter about the frequency of the predetermined tone and the first bandwidth of the auditory filter about the first acoustic therapy signal each have an upper edge and a lower edge, and
the measure of coverage between the reference bandwidth and the first bandwidth is a function of a difference between the upper edge of the bandwidth of a lower acoustic signal of the predetermined tone and the first acoustic therapy signal and the lower edge of the bandwidth of the other acoustic signal.

Embodiment 3

The device (10) according to Embodiment 1 or 2, wherein the control unit (11) is configured to:
determine a frequency of a second acoustic therapy signal, such that a measure of coverage between the reference bandwidth about the frequency of the predetermined tone and a second bandwidth of an auditory filter with the frequency of the second acoustic therapy signal as a center frequency assumes a predetermined second value, and control the stimulation unit (12) such that the stimulation unit (12) generates the second acoustic therapy signal.

Embodiment 4

The device (10) according to Embodiment 3, wherein one of the first acoustic therapy signal and the second acoustic therapy signal has a lower frequency than the predetermined tone, and the other acoustic therapy signal has a higher frequency than the predetermined tone.

Embodiment 5

The device (10) according to Embodiment 3 or 4, wherein:
- the control unit (11) is configured to determine the frequency of the first acoustic therapy signal by varying the frequency of the first acoustic therapy signal until the measure of coverage between the reference bandwidth about the frequency of the predetermined tone and the first bandwidth of the auditory filter with the frequency of the first acoustic therapy signal as the center frequency assumes the predetermined first value, and
- the control unit (11) is configured to determine the frequency of the second acoustic therapy signal by varying the frequency of the second acoustic therapy signal until the measure of coverage between the reference bandwidth about the frequency of the predetermined tone and the second bandwidth of the auditory filter with the frequency of the second acoustic therapy signal as the center frequency assumes the predetermined second value.

Embodiment 6

The device (10) according to any one of Embodiments 3 to 5, wherein the control unit (11) is configured to:
- determine a frequency of a third acoustic therapy signal, such that a measure of coverage between the reference bandwidth about the frequency of the predetermined tone and a third bandwidth of an auditory filter with the frequency of the third acoustic therapy signal as a center frequency assumes a predetermined third value, and control the stimulation unit (12) such that the stimulation unit (12) generates the third acoustic therapy signal.

Embodiment 7

The device (10) according to any one of Embodiments 3 to 5, wherein the control unit (11) is configured to:
- determine a frequency of a third acoustic therapy signal, such that a measure of coverage between the first or second bandwidth of the auditory filter with the frequency of the first or second acoustic therapy signal as the center frequency and a third bandwidth of an auditory filter with the frequency of the third acoustic therapy signal as a center frequency assumes a predetermined third value,
- control the stimulation unit (12) such that the stimulation unit (12) generates the third acoustic therapy signal.

Embodiment 8

The device (10) according to any one of the preceding Embodiments 1 to 7, wherein at least one of the following applies:
- the reference bandwidth depends on a hearing threshold of the patient at the frequency of the predetermined tone,
- the first bandwidth depends on the hearing threshold of the patient at the frequency of the first acoustic therapy signal,
- the second bandwidth depends on the hearing threshold of the patient at the frequency of the second acoustic therapy signal, and
- the third bandwidth depends on the hearing threshold of the patient at the frequency of the third acoustic therapy signal.

Embodiment 9

The device (10) according to any one of the preceding Embodiments 1 to 8, wherein at least one of the following applies:
- the reference bandwidth is an equivalent rectangular bandwidth of the auditory filter at the frequency of the predetermined tone,
- the first bandwidth is an equivalent rectangular bandwidth of the auditory filter at the frequency of the first acoustic therapy signal,
- the second bandwidth is an equivalent rectangular bandwidth of the auditory filter at the frequency of the second acoustic therapy signal, and
- the third bandwidth is an equivalent rectangular bandwidth of the auditory filter at the frequency of the third acoustic therapy signal.

Embodiment 10

The device (10) according to any one of the preceding Embodiments 1 to 9, wherein the frequency of the predetermined tone is a frequency of the patient's tinnitus tone estimated by pitch matching.

Embodiment 11

The device (10) according to any one of the preceding Embodiments 1 to 10, wherein at least one of the following applies:
- the first acoustic therapy signal is a first therapy tone or a first therapy tone mixture, the second acoustic therapy signal is a second therapy tone or a second therapy tone mixture, and
- the third acoustic therapy signal is a third therapy tone or a third therapy tone mixture.

Embodiment 12

The device (10) according to any one of the preceding Embodiments 1 to 11, wherein each measure of coverage is an overlap or a gap.

Embodiment 13

The device (10) according to Embodiment 6 or 7, wherein the control unit (11) is configured to control the stimulation unit (12), such that the stimulation unit (12) generates the first acoustic therapy signal, the second acoustic therapy signal and the third acoustic therapy signal with a time lag relative to one another, wherein amplitudes of the acoustic therapy signals are each adjusted, so that the acoustic therapy signals trigger a phase reset of a neural activity of respective stimulated neurons in the patient's brain.

Embodiment 14

A method for stimulation of a patient with acoustic stimulation signals, comprising:
  determining a bandwidth of an auditory filter with a frequency of a predetermined tone as a center frequency, wherein the bandwidth is a reference bandwidth,
  determining a frequency of a first acoustic therapy signal such that a measure of coverage between the reference bandwidth about the frequency of the predetermined tone and a first bandwidth of an auditory filter with the frequency of the first acoustic therapy signal as a center frequency assumes a predetermined first value, and
  generating the first acoustic therapy signal.

Embodiment 15

A non-transitory computer-readable medium comprising computer code for execution in a data processing system to:
  determine a bandwidth of an auditory filter with a frequency of a predetermined tone as a center frequency, wherein the bandwidth is a reference bandwidth,
  determine a frequency of a first acoustic therapy signal, such that a measure of coverage between the reference bandwidth about the frequency of the predetermined tone and a first bandwidth of an auditory filter with the frequency of the first acoustic therapy signal as a center frequency assumes a predetermined first value, and
  generate control signals for controlling a stimulation unit (12) to generate the first acoustic therapy signal.

Embodiment 16

A device (10) for stimulation of a patient with acoustic stimulation signals, comprising:
  a stimulation unit (12) configured to generate acoustic stimulation signals, and
  a control unit (11) connected to the stimulation unit (12) and configured to control the stimulation unit (12), wherein the control unit (11) is configured to
  determine a frequency of a first acoustic therapy signal and a frequency of a second acoustic therapy signal, such that a measure of coverage between a first bandwidth of an auditory filter with the frequency of the first acoustic therapy signal as a center frequency and a second bandwidth of an auditory filter with the frequency of the second acoustic therapy signal as a center frequency assumes a predetermined first value, and
  control the stimulation unit (12) such that the stimulation unit (12) generates the first acoustic therapy signal and the second acoustic therapy signal.

Embodiment 17

The device (10) according to Embodiment 16, wherein the device (10) comprises an evaluation unit (13) configured to evaluate a success of a treatment.

Embodiment 18

The device (10) according to Embodiment 17, wherein the control unit (11) is configured to:
  determine a frequency of a third acoustic therapy signal such that a measure of coverage between the first bandwidth of the auditory filter with the frequency of the first acoustic therapy signal as the center frequency and a third bandwidth of an auditory filter with the frequency of the third acoustic therapy signal as a center frequency assumes a predetermined second value,
  control the stimulation unit (12) such that the stimulation unit (12) generates the first, second and third acoustic therapy signals and
  discard the third acoustic therapy signal if the evaluation unit (13) does not identify a sufficient therapeutic success in stimulation with the first, second and third acoustic therapy signals.

Embodiment 19

The device (10) according to Embodiment 18, wherein the control unit (11) is configured to, if the evaluation unit (13) identifies a sufficient therapeutic success in stimulation with the first, second and third acoustic therapy signals:
  determine a frequency of a fourth acoustic therapy signal such that a measure of overlap between the second bandwidth of the auditory filter with the frequency of the second acoustic therapy signal as the center frequency and a fourth bandwidth of an auditory filter with the frequency of the fourth acoustic therapy signal as a center frequency assumes a predetermined third value,
  control the stimulation unit (12) such that the stimulation unit (12) generates the first, the second, the third and the fourth acoustic therapy signals and
  discard the fourth acoustic therapy signal if the evaluation unit (13) does not identify a sufficient therapeutic success in stimulation with the first, second, third and fourth acoustic therapy signals.

Embodiment 20

The device (10) according to Embodiment 18, wherein the control unit (11) is configured to, if the evaluation unit (13) identifies a sufficient therapeutic success in stimulation with the first, second and third acoustic therapy signals:
  determine a frequency of a fourth acoustic therapy signal such that a measure of coverage between the third bandwidth of the auditory filter with the frequency of the third acoustic therapy signal as the center frequency and a fourth bandwidth of an auditory filter with the frequency of the fourth acoustic therapy signal as a center frequency assumes a predetermined third value,
  control the stimulation unit (12) such that the stimulation unit (12) generates the first, second, third and fourth acoustic therapy signals and
  discard the fourth acoustic therapy signal if the evaluation unit (13) does not identify a sufficient therapeutic success in stimulation with the first, second, third and fourth acoustic therapy signals.

Embodiment 21

The device (10) according to any one of Embodiments 16 to 20, wherein the control unit (11) is configured to:
  determine the frequency of the first acoustic therapy signal and the frequency of the second acoustic therapy signal for multiple values for the measure of coverage between the first bandwidth of the auditory filter with the frequency of the first acoustic therapy signal as the center frequency and the second bandwidth of the auditory filter with the frequency of the second acoustic therapy signal as the center frequency,
  control the stimulation unit (12) such that the stimulation unit (12) generates a respective pair from the first acoustic therapy signal and the second acoustic therapy signal for each of the multiple values for the measure of coverage, and
  select the pair in which the evaluation unit (13) identifies a greatest therapeutic success.

Embodiment 22

The device (10) according to any one of Embodiments 16 to 21, wherein a frequency of a tinnitus tone perceived by the patient is between the frequency of the first acoustic therapy signal and the frequency of the second acoustic therapy signal.

Embodiment 23

The device (10) according to any one of Embodiments 16 to 22, wherein at least one of the following applies:
  the first bandwidth is a function of the patient's hearing threshold at the frequency of the first acoustic therapy signal,
  the second bandwidth is a function of the patient's hearing threshold at the frequency of the second acoustic therapy signal,
  the third bandwidth is a function of the patient's hearing threshold at the frequency of the third acoustic therapy signal, and
  the fourth bandwidth is a function of the patient's hearing threshold at the frequency of the fourth acoustic therapy signal.

Embodiment 24

The device (10) according to any one of Embodiments 16 to 23, wherein at least one of the following applies:
  the first bandwidth is an equivalent rectangular bandwidth of the auditory filter at the frequency of the first acoustic therapy signal,
  the second bandwidth is an equivalent rectangular bandwidth of the auditory filter at the frequency of the second acoustic therapy signal,
  the third bandwidth is an equivalent rectangular bandwidth of the auditory filter at the frequency of the third acoustic therapy signal, and
  the fourth bandwidth is an equivalent rectangular bandwidth of the auditory filter at the frequency of the fourth acoustic therapy signal.

Embodiment 25

The device (10) according to any one of Embodiments 16 to 24, wherein at least one of the following applies:
  the first acoustic therapy signal is a first therapy tone or a first therapy tone mixture,
  the second acoustic therapy signal is a second therapy tone or a second therapy tone mixture,
  the third acoustic therapy signal is a third therapy tone or a third therapy tone mixture, and
  the fourth acoustic therapy signal is a fourth therapy tone or a fourth therapy tone mixture.

Embodiment 26

The device (10) according to any one of Embodiments 16 to 25, wherein each measure of coverage is an overlap or a gap.

Embodiment 27

The device (10) according to Embodiment 19 or 20, wherein the control unit (11) is configured to control the stimulation unit (12) such that the stimulation unit (12) generates the first acoustic therapy signal, the second acoustic therapy signal, the third acoustic therapy signal and the fourth acoustic therapy signal with a time lag between one another, wherein amplitudes of the acoustic therapy signals are each adjusted so that the acoustic therapy signals trigger a phase reset of a neural activity of respective neurons stimulated in the patient's brain.

Embodiment 28

A method for stimulation of a patient with acoustic stimulation signals, comprising:
  determining a frequency of a first acoustic therapy signal and a frequency of a second acoustic therapy signal such that a measure of coverage between a first bandwidth of an auditory filter with the frequency of the first acoustic therapy signal as a center frequency and a second bandwidth of an auditory filter with the frequency of the second acoustic therapy signal as a center frequency assumes a predetermined first value, and
  generating the first acoustic therapy signal and the second acoustic therapy signal.

Embodiment 29

A non-transitory computer-readable medium comprising computer code for execution in a data processing system to:
  determine a frequency of a first acoustic therapy signal and a frequency of a second acoustic therapy signal such that a measure of coverage between a first bandwidth of an auditory filter with the frequency of the first acoustic therapy signal as a center frequency and a second bandwidth of an auditory filter with the frequency of the second acoustic therapy signal as a center frequency assumes a predetermined first value, and
  generate control signals for controlling a stimulation unit (12) to generate the first acoustic therapy signal and the second acoustic therapy signal.

As used herein, the singular terms "a," "an," and "the" may include plural referents unless the context clearly dictates otherwise. Thus, for example, reference to an object may include multiple objects unless the context clearly dictates otherwise.

As used herein, the terms "approximately," "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can encompass a range of variation of less than or equal to ±10% of that numerical value, such as less than or equal to ±5%, less than or equal to ±4%, less than or equal to ±3%, less than or equal to ±2%, less than or equal to +1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Some embodiments of this disclosure relate to a non-transitory computer-readable storage medium having computer code or instructions thereon for performing various computer-implemented operations. The term "computer-readable storage medium" is used to include any medium that is capable of storing or encoding a sequence of instructions or computer code for performing the operations, methodologies, and techniques described herein. The media and computer code may be those specially designed and constructed for the purposes of the embodiments of this disclosure, or may be of the kind available to those having skill in the computer software arts. Examples of computer-readable storage media include, but are not limited to: magnetic media such as hard disks, floppy disks, and magnetic tape; optical media such as CD-ROMs and holographic devices; magneto-optical media such as optical disks; and hardware devices that are specially configured to store and execute program code, such as application-specific integrated circuits (ASICs), programmable logic devices (PLDs), and ready-only memory (ROM) and random-access memory (RAM) devices. Examples of computer code include machine code, such as produced by a compiler, and files containing higher-level code that are executed by a processor using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computing device) to a requesting computer (e.g., a client computing device or a different server computing device) via a transmission channel. Another embodiment of the disclosure may be implemented in hardwired circuitry in place of, or in combination with, processor-executable software instructions.

While this disclosure has been described with reference to the specific embodiments thereof, it should be understood by those skilled in the art that various changes may be made and equivalents may be substituted without departing from the true spirit and scope of this disclosure as defined by the appended claims. In addition, many modifications may be made to adapt a particular situation, material, composition of matter, method, operation or operations, to the objective, spirit and scope of this disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of this disclosure. Accordingly, unless specifically indicated herein, the order and grouping of the operations are not a limitation of this disclosure.

The invention claimed is:

1. A device (10) for stimulation of a patient with acoustic stimulation signals, comprising:
   a stimulation unit (12) configured to generate acoustic stimulation signals, and
   a control unit (11) connected to the stimulation unit (12) and configured to control the stimulation unit (12), wherein the control unit (11) is configured to
      determine a bandwidth of an auditory filter with a frequency of a predetermined tone as a center frequency, wherein the bandwidth represents a reference bandwidth, determine a frequency of a first acoustic therapy signal, such that a measure of coverage between the reference bandwidth around the frequency of the predetermined tone and a first bandwidth of an auditory filter with the frequency of the first acoustic therapy signal as a center frequency assumes a predetermined first value, and
      control the stimulation unit (12) such that the stimulation unit (12) generates the first acoustic therapy signal.

2. The device (10) according to claim 1, wherein:
   the reference bandwidth of the auditory filter about the frequency of the predetermined tone and the first bandwidth of the auditory filter about the first acoustic therapy signal each have an upper edge and a lower edge, and
   the measure of coverage between the reference bandwidth and the first bandwidth is a function of a difference between the upper edge of the bandwidth of a lower acoustic signal of the predetermined tone and the first acoustic therapy signal and the lower edge of the bandwidth of the other acoustic signal.

3. The device (10) according to claim 1, wherein the control unit (11) is configured to:
   determine a frequency of a second acoustic therapy signal, such that a measure of coverage between the reference bandwidth about the frequency of the predetermined tone and a second bandwidth of an auditory filter with the frequency of the second acoustic therapy signal as a center frequency assumes a predetermined second value, and
   control the stimulation unit (12) such that the stimulation unit (12) generates the second acoustic therapy signal.

4. The device (10) according to claim 3, wherein one of the first acoustic therapy signal and the second acoustic therapy signal has a lower frequency than the predetermined tone, and the other acoustic therapy signal has a higher frequency than the predetermined tone.

5. The device (10) according to claim 3, wherein:
   the control unit (11) is configured to determine the frequency of the first acoustic therapy signal by varying the frequency of the first acoustic therapy signal until the measure of coverage between the reference bandwidth about the frequency of the predetermined tone and the first bandwidth of the auditory filter with the frequency of the first acoustic therapy signal as the center frequency assumes the predetermined first value, and the control unit (11) is configured to determine the frequency of the second acoustic therapy signal by varying the frequency of the second acoustic therapy signal until the measure of coverage between the reference bandwidth about the frequency of the predetermined tone and the second bandwidth of the auditory filter with the frequency of the second acoustic therapy signal as the center frequency assumes the predetermined second value.

6. The device (10) according to claim 3, wherein the control unit (11) is configured to:

determine a frequency of a third acoustic therapy signal, such that a measure of coverage between the reference bandwidth about the frequency of the predetermined tone and a third bandwidth of an auditory filter with the frequency of the third acoustic therapy signal as a center frequency assumes a predetermined third value, and control the stimulation unit (12) such that the stimulation unit (12) generates the third acoustic therapy signal.

7. The device (10) according to claim 3, wherein the control unit (11) is configured to:

determine a frequency of a third acoustic therapy signal, such that a measure of coverage between the first or second bandwidth of the auditory filter with the frequency of the first or second acoustic therapy signal as the center frequency and a third bandwidth of an auditory filter with the frequency of the third acoustic therapy signal as a center frequency assumes a predetermined third value, and control the stimulation unit (12) such that the stimulation unit (12) generates the third acoustic therapy signal.

8. The device (10) according to claim 1, wherein at least one of the following applies:

the reference bandwidth depends on a hearing threshold of the patient at the frequency of the predetermined tone, the first bandwidth depends on the hearing threshold of the patient at the frequency of the first acoustic therapy signal, the second bandwidth depends on the hearing threshold of the patient at the frequency of the second acoustic therapy signal, and the third bandwidth depends on the hearing threshold of the patient at the frequency of the third acoustic therapy signal.

9. The device (10) according to claim 1, wherein at least one of the following applies:

the reference bandwidth is an equivalent rectangular bandwidth of the auditory filter at the frequency of the predetermined tone, the first bandwidth is an equivalent rectangular bandwidth of the auditory filter at the frequency of the first acoustic therapy signal, the second bandwidth is an equivalent rectangular bandwidth of the auditory filter at the frequency of the second acoustic therapy signal, and the third bandwidth is an equivalent rectangular bandwidth of the auditory filter at the frequency of the third acoustic therapy signal.

10. The device (10) according to claim 1, wherein the frequency of the predetermined tone is a frequency of the patient's tinnitus tone estimated by pitch matching.

11. The device (10) according to claim 1, wherein at least one of the following applies:

the first acoustic therapy signal is a first therapy tone or a first therapy tone mixture, the second acoustic therapy signal is a second therapy tone or a second therapy tone mixture, and the third acoustic therapy signal is a third therapy tone or a third therapy tone mixture.

12. The device (10) according to claim 1, wherein each measure of coverage is an overlap or a gap.

13. The device (10) according to claim 6, wherein the control unit (11) is configured to control the stimulation unit (12), such that the stimulation unit (12) generates the first acoustic therapy signal, the second acoustic therapy signal and the third acoustic therapy signal with a time lag relative to one another, wherein amplitudes of the acoustic therapy signals are each adjusted, so that the acoustic therapy signals trigger a phase reset of a neural activity of respective stimulated neurons in the patient's brain.

14. A method for stimulation of a patient with acoustic stimulation signals, comprising:

determining a bandwidth of an auditory filter with a frequency of a predetermined tone as a center frequency, wherein the bandwidth is a reference bandwidth, determining a frequency of a first acoustic therapy signal such that a measure of coverage between the reference bandwidth about the frequency of the predetermined tone and a first bandwidth of an auditory filter with the frequency of the first acoustic therapy signal as a center frequency assumes a predetermined first value, and generating the first acoustic therapy signal.

15. A non-transitory computer-readable medium comprising computer code for execution in a data processing system to:

determine a bandwidth of an auditory filter with a frequency of a predetermined tone as a center frequency, wherein the bandwidth is a reference bandwidth, determine a frequency of a first acoustic therapy signal, such that a measure of coverage between the reference bandwidth about the frequency of the predetermined tone and a first bandwidth of an auditory filter with the frequency of the first acoustic therapy signal as a center frequency assumes a predetermined first value, and generate control signals for controlling a stimulation unit (12) to generate the first acoustic therapy signal.

16. A device (10) for stimulation of a patient with acoustic stimulation signals, comprising:

a stimulation unit (12) configured to generate acoustic stimulation signals, and a control unit (11) connected to the stimulation unit (12) and configured to control the stimulation unit (12), wherein the control unit (11) is configured to determine a frequency of a first acoustic therapy signal and a frequency of a second acoustic therapy signal, such that a measure of coverage between a first bandwidth of an auditory filter with the frequency of the first acoustic therapy signal as a center frequency and a second bandwidth of an auditory filter with the frequency of the second acoustic therapy signal as a center frequency assumes a predetermined first value, and control the stimulation unit (12) such that the stimulation unit (12) generates the first acoustic therapy signal and the second acoustic therapy signal.

17. The device (10) according to claim 16, wherein the device (10) comprises an evaluation unit (13) configured to evaluate a success of a treatment.

18. The device (10) according to claim 17, wherein the control unit (11) is configured to:
determine a frequency of a third acoustic therapy signal such that a measure of coverage between the first bandwidth of the auditory filter with the frequency of the first acoustic therapy signal as the center frequency and a third bandwidth of an auditory filter with the frequency of the third acoustic therapy signal as a center frequency assumes a predetermined second value,
control the stimulation unit (12) such that the stimulation unit (12) generates the first, second and third acoustic therapy signals and
discard the third acoustic therapy signal if the evaluation unit (13) does not identify a sufficient therapeutic success in stimulation with the first, second and third acoustic therapy signals.

19. The device (10) according to claim 18, wherein the control unit (11) is configured to, if the evaluation unit (13) identifies a sufficient therapeutic success in stimulation with the first, second and third acoustic therapy signals:
determine a frequency of a fourth acoustic therapy signal such that a measure of overlap between the second bandwidth of the auditory filter with the frequency of the second acoustic therapy signal as the center frequency and a fourth bandwidth of an auditory filter with the frequency of the fourth acoustic therapy signal as a center frequency assumes a predetermined third value,
control the stimulation unit (12) such that the stimulation unit (12) generates the first, the second, the third and the fourth acoustic therapy signals and
discard the fourth acoustic therapy signal if the evaluation unit (13) does not identify a sufficient therapeutic success in stimulation with the first, second, third and fourth acoustic therapy signals.

20. The device (10) according to claim 18, wherein the control unit (11) is configured to, if the evaluation unit (13) identifies a sufficient therapeutic success in stimulation with the first, second and third acoustic therapy signals:
determine a frequency of a fourth acoustic therapy signal such that a measure of coverage between the third bandwidth of the auditory filter with the frequency of the third acoustic therapy signal as the center frequency and a fourth bandwidth of an auditory filter with the frequency of the fourth acoustic therapy signal as a center frequency assumes a predetermined third value,
control the stimulation unit (12) such that the stimulation unit (12) generates the first, second, third and fourth acoustic therapy signals and
discard the fourth acoustic therapy signal if the evaluation unit (13) does not identify a sufficient therapeutic success in stimulation with the first, second, third and fourth acoustic therapy signals.

21. The device (10) according to claim 16, wherein the control unit (11) is configured to:
determine the frequency of the first acoustic therapy signal and the frequency of the second acoustic therapy signal for multiple values for the measure of coverage between the first bandwidth of the auditory filter with the frequency of the first acoustic therapy signal as the center frequency and the second bandwidth of the auditory filter with the frequency of the second acoustic therapy signal as the center frequency,
control the stimulation unit (12) such that the stimulation unit (12) generates a respective pair from the first acoustic therapy signal and the second acoustic therapy signal for each of the multiple values for the measure of coverage, and
select the pair in which the evaluation unit (13) identifies a greatest therapeutic success.

22. The device (10) according to claim 16, wherein a frequency of a tinnitus tone perceived by the patient is between the frequency of the first acoustic therapy signal and the frequency of the second acoustic therapy signal.

23. The device (10) according to claim 16, wherein at least one of the following applies:
the first bandwidth is a function of the patient's hearing threshold at the frequency of the first acoustic therapy signal,
the second bandwidth is a function of the patient's hearing threshold at the frequency of the second acoustic therapy signal,
the third bandwidth is a function of the patient's hearing threshold at the frequency of the third acoustic therapy signal, and
the fourth bandwidth is a function of the patient's hearing threshold at the frequency of the fourth acoustic therapy signal.

24. The device (10) according to claim 16, wherein at least one of the following applies:
the first bandwidth is an equivalent rectangular bandwidth of the auditory filter at the frequency of the first acoustic therapy signal,
the second bandwidth is an equivalent rectangular bandwidth of the auditory filter at the frequency of the second acoustic therapy signal,
the third bandwidth is an equivalent rectangular bandwidth of the auditory filter at the frequency of the third acoustic therapy signal, and
the fourth bandwidth is an equivalent rectangular bandwidth of the auditory filter at the frequency of the fourth acoustic therapy signal.

25. The device (10) according to claim 16, wherein at least one of the following applies:
the first acoustic therapy signal is a first therapy tone or a first therapy tone mixture,
the second acoustic therapy signal is a second therapy tone or a second therapy tone mixture,
the third acoustic therapy signal is a third therapy tone or a third therapy tone mixture, and
the fourth acoustic therapy signal is a fourth therapy tone or a fourth therapy tone mixture.

26. The device (10) according to claim 16, wherein each measure of coverage is an overlap or a gap.

27. The device (10) according to claim 19, wherein the control unit (11) is configured to control the stimulation unit (12) such that the stimulation unit (12) generates the first acoustic therapy signal, the second acoustic therapy signal, the third acoustic therapy signal and the fourth acoustic therapy signal with a time lag between one another, wherein amplitudes of the acoustic therapy signals are each adjusted so that the acoustic therapy signals trigger a phase reset of a neural activity of respective neurons stimulated in the patient's brain.

28. A method for stimulation of a patient with acoustic stimulation signals, comprising:
- determining a frequency of a first acoustic therapy signal and a frequency of a second acoustic therapy signal such that a measure of coverage between a first bandwidth of an auditory filter with the frequency of the first acoustic therapy signal as a center frequency and a second bandwidth of an auditory filter with the frequency of the second acoustic therapy signal as a center frequency assumes a predetermined first value, and
- generating the first acoustic therapy signal and the second acoustic therapy signal.

29. A non-transitory computer-readable medium comprising computer code for execution in a data processing system to:
- determine a frequency of a first acoustic therapy signal and a frequency of a second acoustic therapy signal such that a measure of coverage between a first bandwidth of an auditory filter with the frequency of the first acoustic therapy signal as a center frequency and a second bandwidth of an auditory filter with the frequency of the second acoustic therapy signal as a center frequency assumes a predetermined first value, and
- generate control signals for controlling a stimulation unit (12) to generate the first acoustic therapy signal and the second acoustic therapy signal.

\* \* \* \* \*